US012637517B2

(12) United States Patent
Shao

(10) Patent No.: US 12,637,517 B2
(45) Date of Patent: May 26, 2026

(54) ENZYME AND PATHWAY MODULATION WITH SULFHYDRYL COMPOUNDS AND THEIR DERIVATIVES

(71) Applicant: HOFFMANN-LA ROCHE INC., Little Falls, NJ (US)

(72) Inventor: Zhixin Shao, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 710 days.

(21) Appl. No.: 17/996,807

(22) PCT Filed: Apr. 23, 2021

(86) PCT No.: PCT/EP2021/060637
§ 371 (c)(1),
(2) Date: Oct. 21, 2022

(87) PCT Pub. No.: WO2021/214277
PCT Pub. Date: Oct. 28, 2021

(65) Prior Publication Data
US 2023/0265204 A1     Aug. 24, 2023

(30) Foreign Application Priority Data
Apr. 24, 2020     (EP) .................................... 20171356

(51) Int. Cl.
*C07K 16/28*        (2006.01)
*C07K 16/18*        (2006.01)

(52) U.S. Cl.
CPC .......... *C07K 16/2887* (2013.01); *C07K 16/18* (2013.01); *C07K 16/2809* (2013.01); *C07K 2317/14* (2013.01); *C07K 2317/31* (2013.01); *C07K 2317/40* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,047,355 A | 9/1991 | Huber et al. | |
| 5,096,816 A | 3/1992 | Maiorella | |
| 5,510,261 A | 4/1996 | Goochee et al. | |
| 11,142,570 B2 | 10/2021 | Ahlijanian et al. | |
| 11,191,832 B2 | 12/2021 | Kinney et al. | |
| 2015/0056134 A1 | 2/2015 | Sawada | |
| 2020/0172627 A1 | 6/2020 | Bacac et al. | |
| 2020/0237905 A1 | 7/2020 | Demario et al. | |
| 2022/0018851 A1 | 1/2022 | Czech et al. | |
| 2024/0327890 A1 | 10/2024 | Popp et al. | |

FOREIGN PATENT DOCUMENTS

| | | |
|---|---|---|
| EP | 3252078 A1 | 12/2017 |
| JP | 2017501848 A | 1/2017 |
| JP | 2020054351 A | 4/2020 |
| RU | 2577226 C2 | 3/2016 |
| WO | 03056914 A1 | 7/2003 |
| WO | 2015128314 A1 | 9/2015 |
| WO | 2018114748 A1 | 6/2018 |
| WO | 2018151821 A1 | 8/2018 |
| WO | 2018/220099 A1 | 12/2018 |
| WO | 2019/020606 A1 | 1/2019 |
| WO | 2019064053 A1 | 4/2019 |
| WO | 2020/033756 A1 | 2/2020 |

OTHER PUBLICATIONS

Raju (mAbs4(3): 385-391 (Year: 2012).*
Xiao et al., NPJ Parkinson;s Disease 11(31): 1-6 (Year: 2025).*
Jakubke H.-D et al., Aminokisloty, peptidy, belki [Aminoacids, peptides, and proteins] Translation from German, Moscow:Mir, 1985, 456 pp., pp. 356-363. English Translation Provided.
International Search Report of International Application No. PCT/EP2021/060637, mailed Jul. 21, 2021.
Raju et al., "Galactosylation variations in marketed therapeutic antibodies", mAbs, May 1, 2012, pp. 385-391, vol. 4, No. 3.
Seo et al., "Effect of glucose feeding on the glycosylation quality of antibody produced by a human cell line, F2N78, in fed-batch culture", Applied Microbiology and Biotechnology, Jan. 3, 2014, pp. 3509-3515, vol. 98, No. 8.
Routier et al., "The glycosylation pattern of a humanized IgGI antibody (D1.3) expressed in CHO cells", Glycoconjugate Journal, Jan. 1, 1997, pp. 201-207, vol. 14, No. 2.
Davies et al., "Expression of GnTIII in a recombinant anti-CD20 CHO production Cell Line: Expression of Antibodies with Altered Glycoforms Leads to an Increase in ADCC Through Higher Affinity for FCgammaRIII", Biotechnology and Bioengineering, Aug. 20, 2001, p. 288-294, vol. 74, No. 4.
Wang et al., "Antibody glycosylation: impact on antibody drug characteristics and quality control", Applied Microbiology and Biotechnology, Jan. 15, 2020, pp. 1905-1914, vol. 104, No. 5.
Goh et al., "Impact of host cell line choice on glycan profile", Critical Reviews in Biotechnology, Dec. 20, 2017, pp. 851-867, vol. 38, No. 6.

(Continued)

*Primary Examiner* — Phuong Huynh
(74) *Attorney, Agent, or Firm* — McBee Moore & Vanik IP, LLC

(57) ABSTRACT

The present invention relates to proteins, particularly antibodies such as anti-CD20/anti-CD3 bispecific antibodies and anti α-synuclein antibodies, having monogalactosylated (G1) and digalactosylated (G2) glycans. More particular, the present invention relates to galactosylation engineering to generate proteins with improved therapeutic properties, including proteins with increased titer. Further, the invention relates to a cell culture medium and a mammalian cell as well as methods using said cell culture medium and said mammalian cell for producing said proteins. Moreover, the present invention relates to the use of said antibodies as a medicament such as for the treatment of cancer, particularly cancer associated with B-cells, or Parkinson's disease.

13 Claims, 18 Drawing Sheets
Specification includes a Sequence Listing.

(56)                    References Cited

OTHER PUBLICATIONS

Hossler et al., "Optimal and consistent protein glycosylation in mammalian cell culture", Glycobiology, Jun. 3, 2009, pp. 936-949, vol. 19, No. 9.

Hearing et al., "Isolation of Chinese Hamster Ovary Cell Lines Temperature Conditional for the Cell-surface Expression of Integral Membrane Glycoproteins", The Journal of Cell Biology, Feb. 1989, pp. 339-353, vol. 108.

Borys, M.C. et al. "Ammonia affects the glycosylation patterns of recombinant mouse placental lactogen-I by chinese hamster ovary cells in a pH-dependent manner" Biotechnology & Bioengineering. 1994;43(6):505-514.

Borys, M.C. et al. "Culture pH Affects Expression Rates and Glycosylation of Recombinant Mouse Placental Lactogen Proteins by Chinese Hamster Ovary (CHO) Cells" Biotechnology (NY). 1993;11(6):720-724.

Boyd, P.N. et al. "The effect of the removal of sialic acid, galactose and total carbohydrate on the functional activity of Campath-1H" Mol. Immunol. 1995;32(17/18):1311-1318.

Chotigeat, W. et al. "Role of environmental conditions on the expression levels, glycoform pattern and levels of sialyltransferase for hFSH produced by recombinant CHO cells" Cytotechnology. 1994;15:217-221.

Cumming, D.A. "Glycosylation of recombinant protein therapeutics: control and functional implications" Glycobiology. 1991;1(2):115-130.

Fortunato, M.E. & Colina, C.M. "Effects of Galactosylation in Immunoglobulin G from All-Atom Molecular Dynamics Simulations" J. Phys. Chem. B 2014, 118, 33, 9844-9851.

Goochee, C.F., Gramer, M., Andersen, D., Bahr, J. and Rasmussen, J.R. 1991. The oligosaccharides of glycoproteins: factors affecting their synthesis and their influence on glycoprotein properties, p. 199-240. In: Frontiers in Bioprocessing II, S. K. Sikdar, M. Bier, and P. Todd, (Eds.). American Chemical Society, Washington, D.C.

Hayter, P.M. et al. "Glucose-limited chemostat culture of Chinese hamster ovary cells producing recombinant human Interferon-gamma" Biotechnol Bioeng. 1992;39(3):327-35.

Karsten, C.M. et al. "Galactosylated IgG1 links FcγRIIB and Dectin-1 to block complement-mediated inflammation" Nat Med. Author manuscript; available in PMC Mar. 1, 2013.Published in final edited form as: Nat Med. 2012;18(9):1401-1406.

Krapp, S. et al. "Structural analysis of human IgG-Fc glycoforms reveals a correlation between glycosylation and structural integrity" J Mol Biol. 2003;325(5):979-89.

Mimura, Y. et al. "The influence of glycosylation on the thermal stability and effector function expression of human IgG1-Fc: properties of a series of truncated glycoforms" Mol Immunol. 2000;37(12-13):697-706.

Werner, R.G. et al. "Mammalian cell cultures. Part I: Characterization, morphology and metabolism" Arzneimittel-Forschung. 1993;43(10):1134-9.

Werner, R.G. et al. "Mammalian cell cultures. Part II: Genetic engineering, protein glycosylation, fermentation and process control" Arzneimittel-Forschung. 1993;43(11):1242-9.

Wittwer, A.J. et al. "Glycosylation at Asn-184 inhibits the conversion of single-chain to two-chain tissue-type plasminogen activator by plasmin" Biochemistry. 1990;29(17):4175-80.

Wright, A. et al. "Effect of glycosylation on antibody function: implications for genetic engineering" Trends Biotechnol. 1997;15(1):26-32.

* cited by examiner

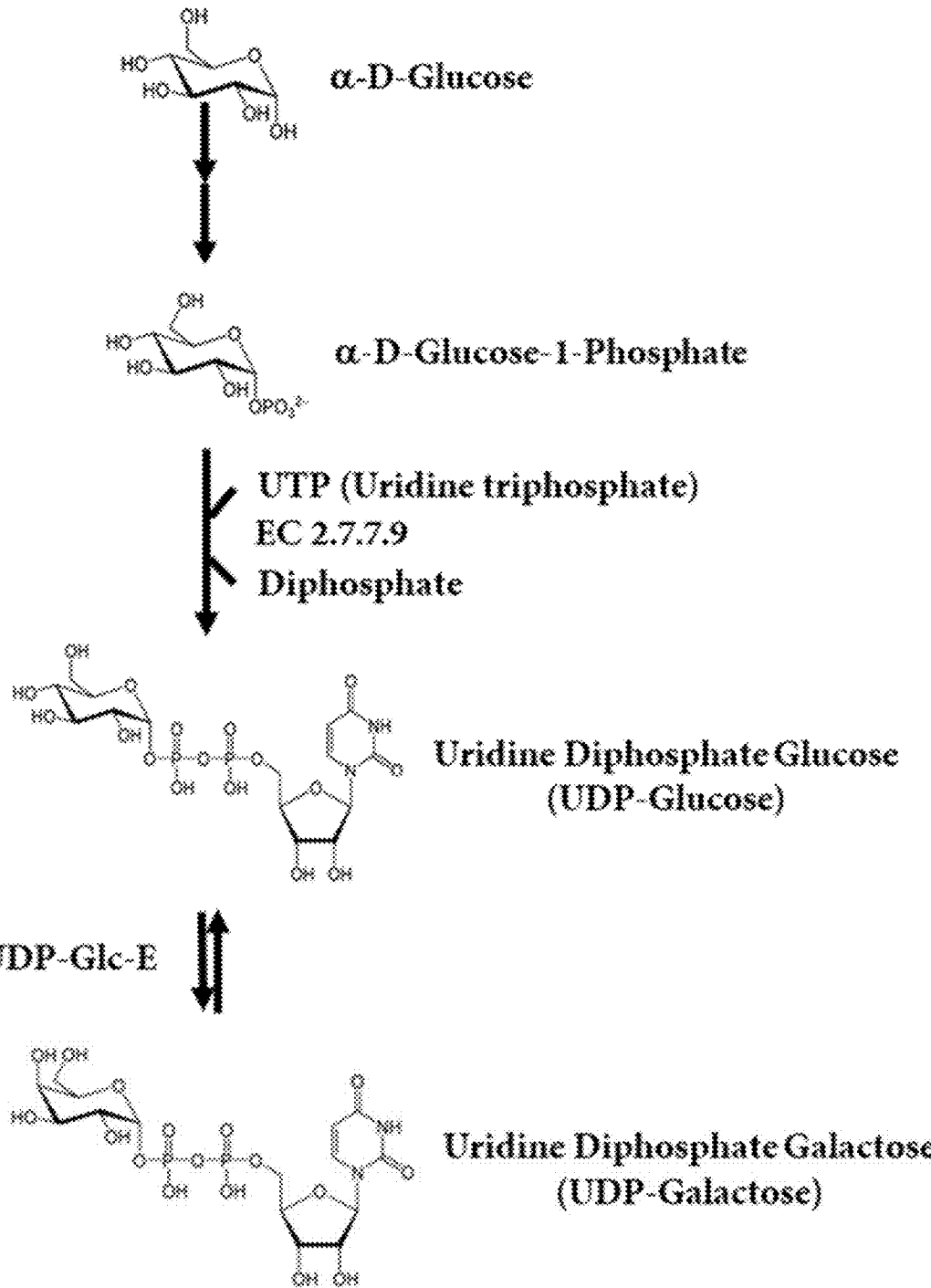
[Figure 1]

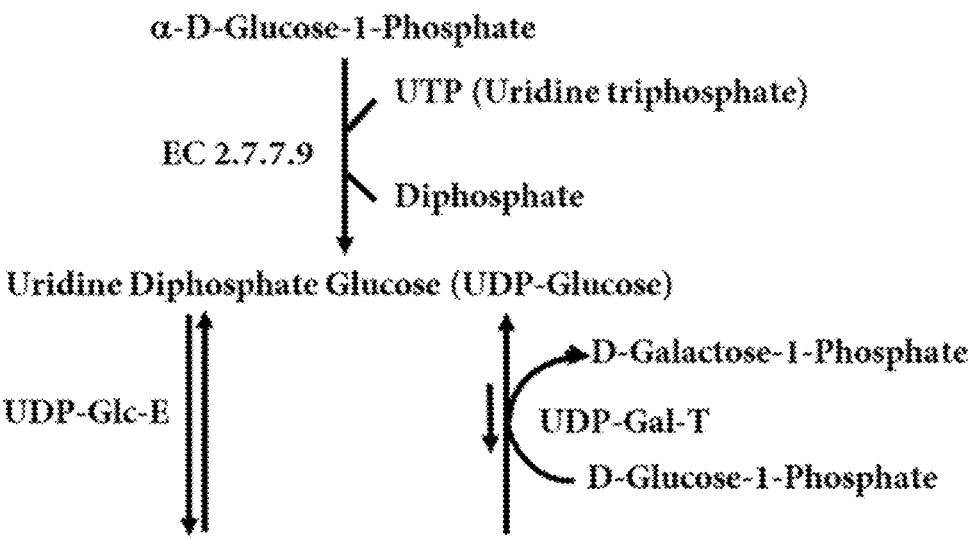
[Figure 2]
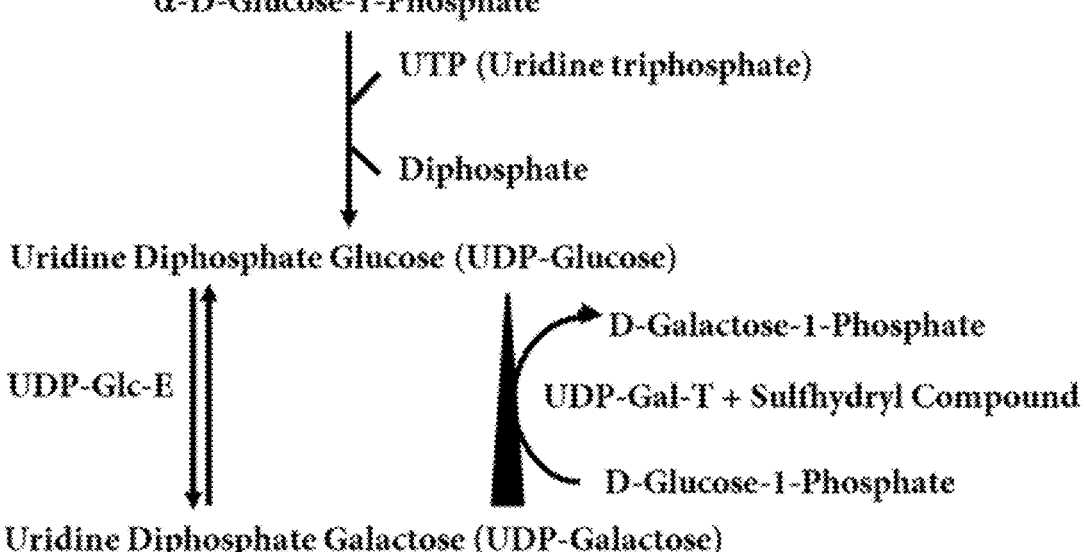
[Figure 3]

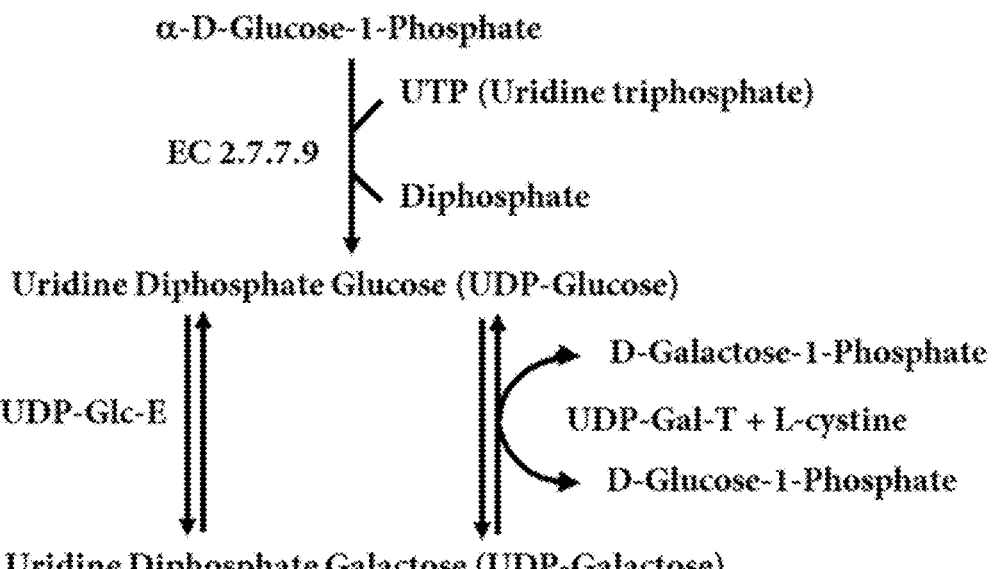
[Figure 4]
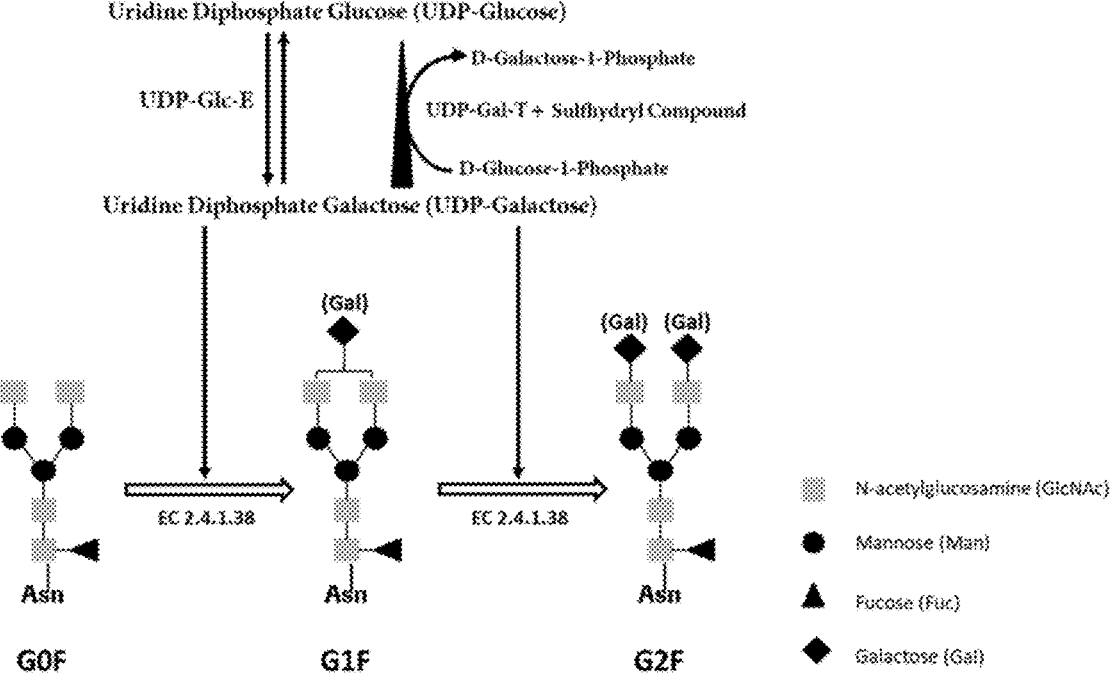
[Figure 5]

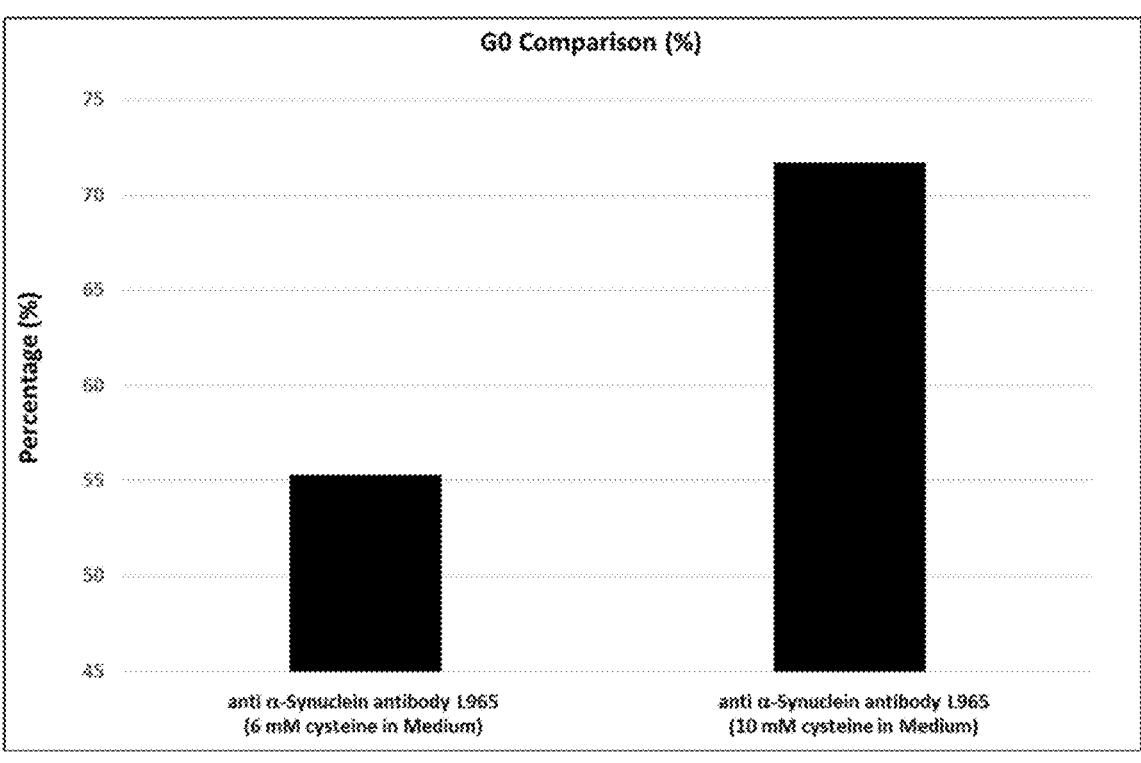
[Figure 6A]
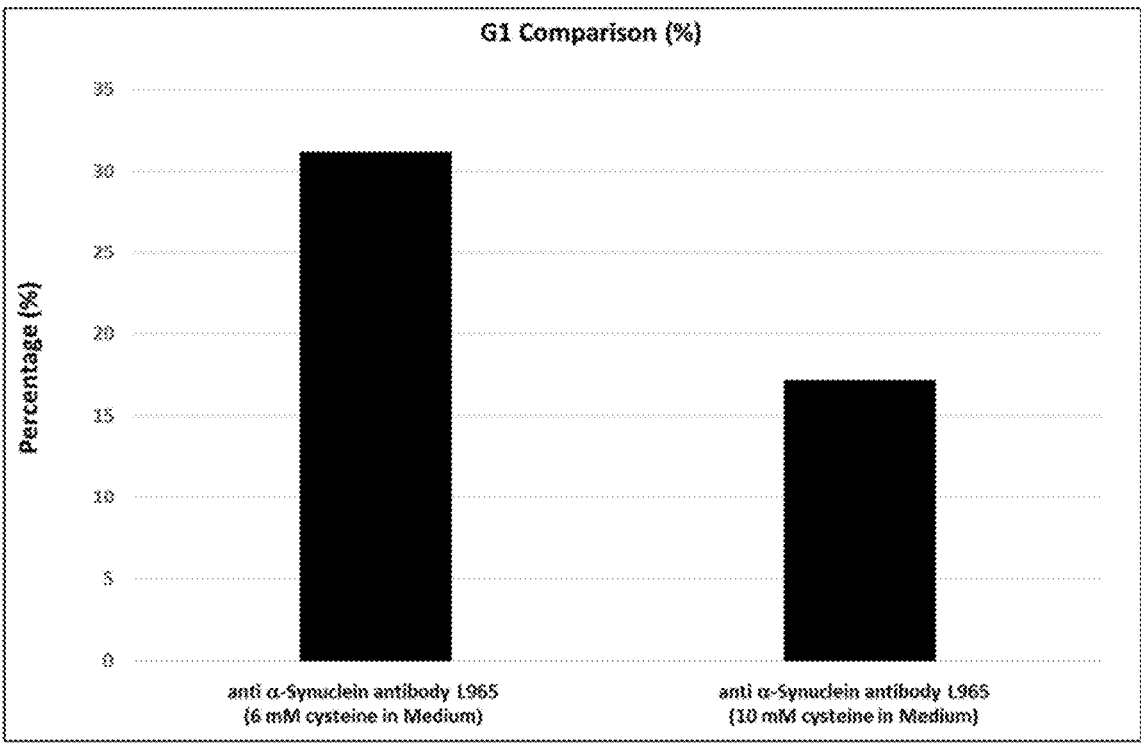
[Figure 6B]

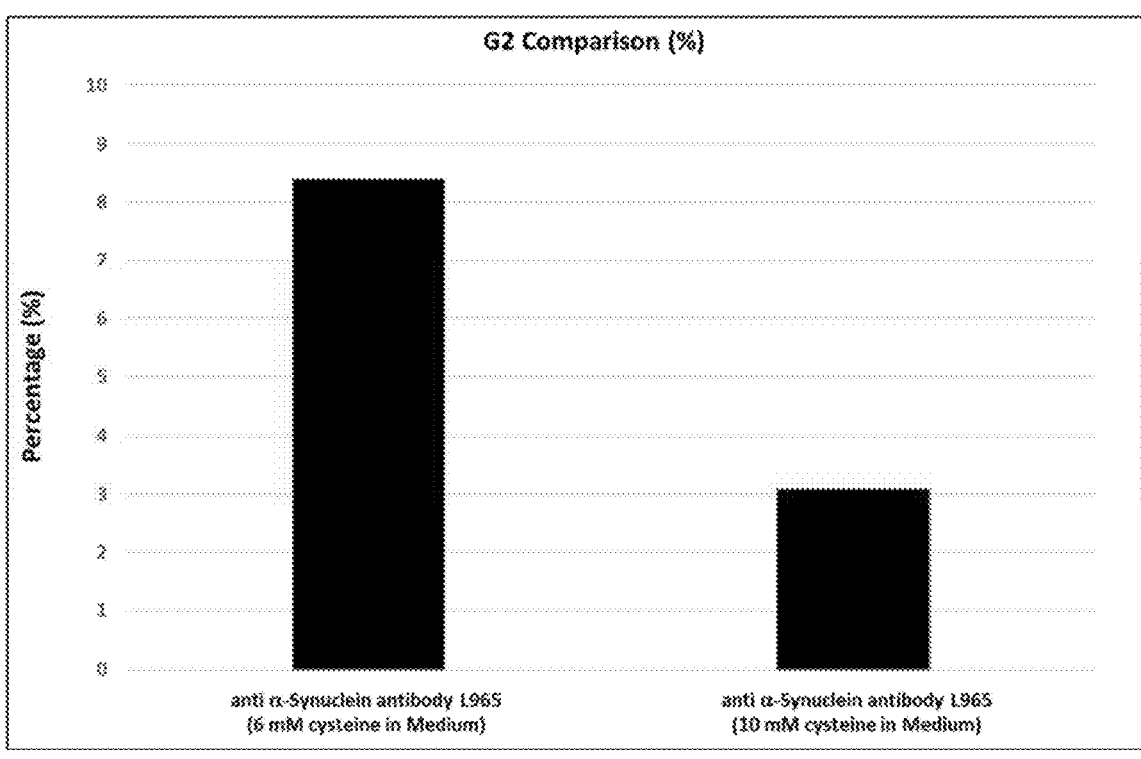
[Figure 6C]
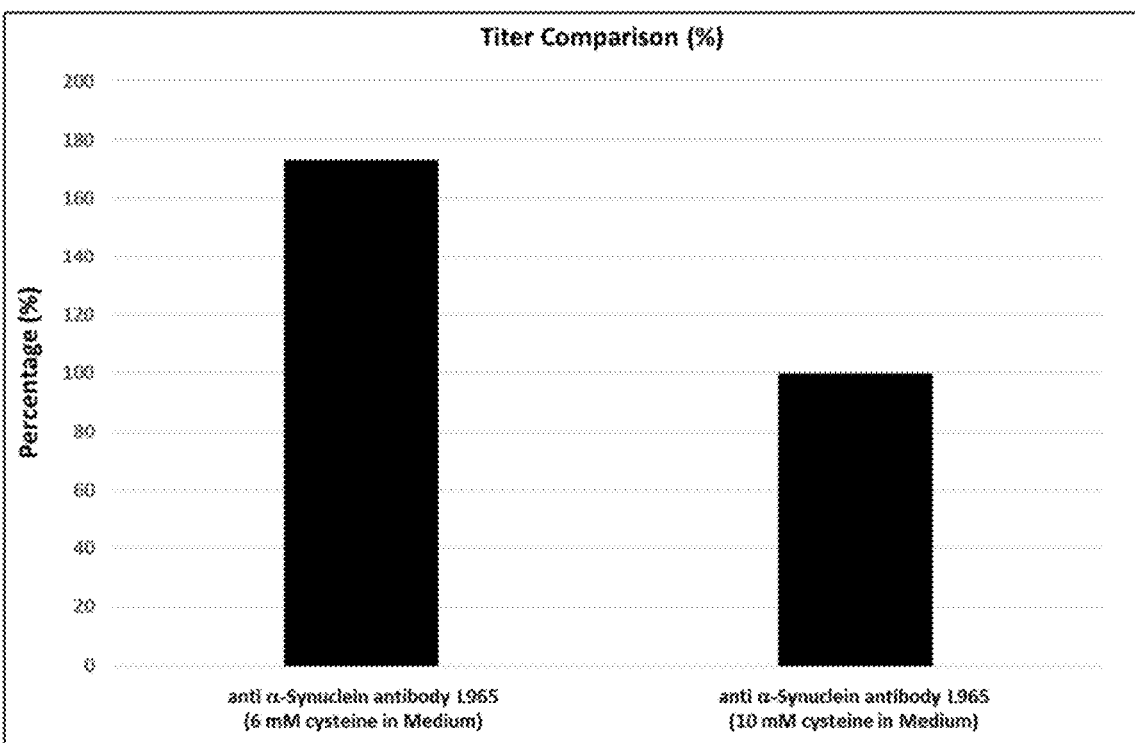
[Figure 6D]

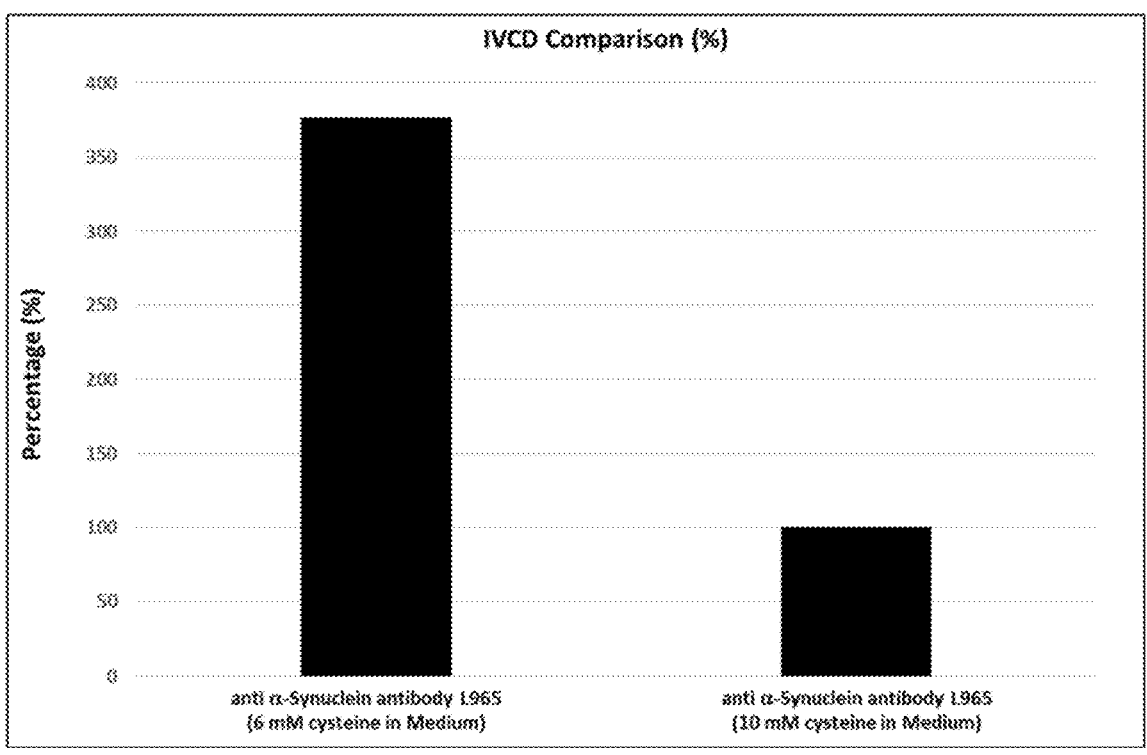
[Figure 6E]
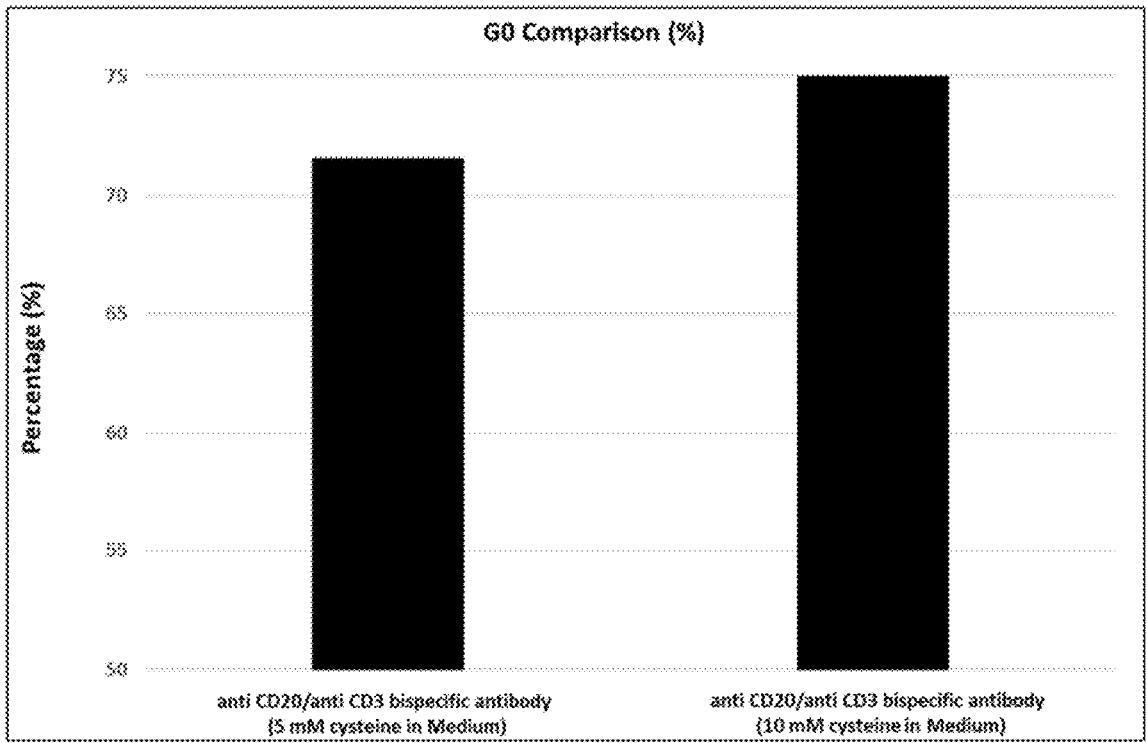
[Figure 7A]

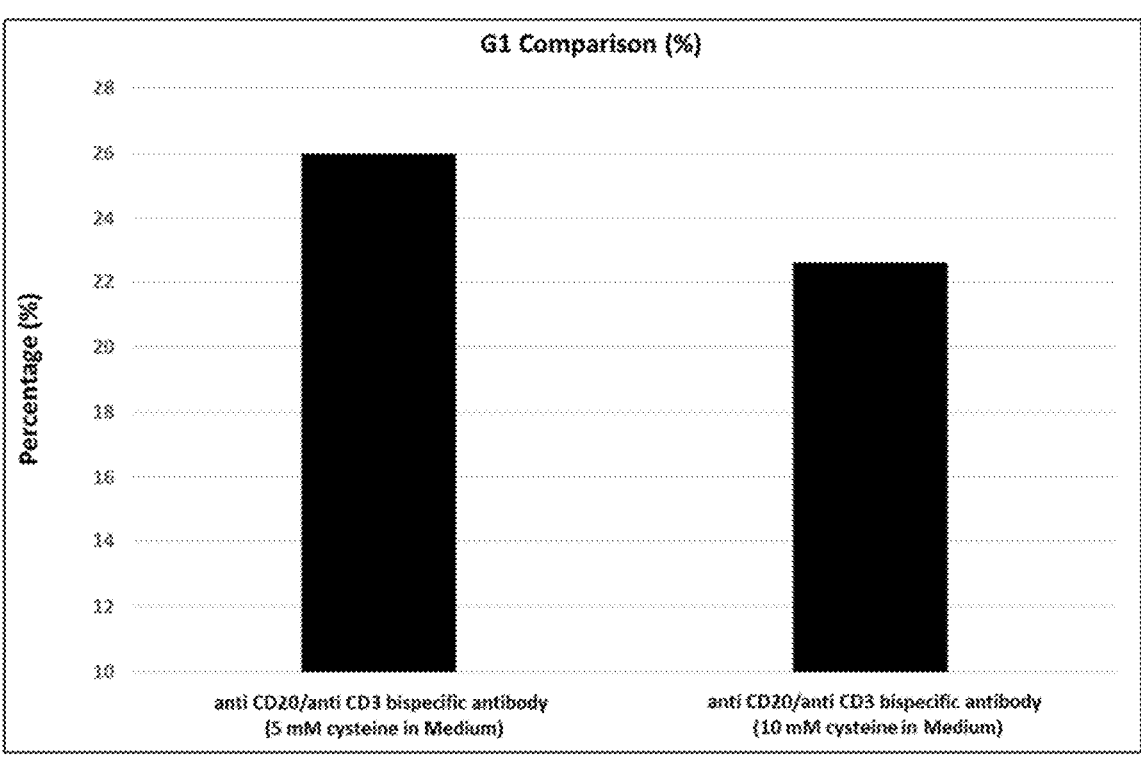
[Figure 7B]
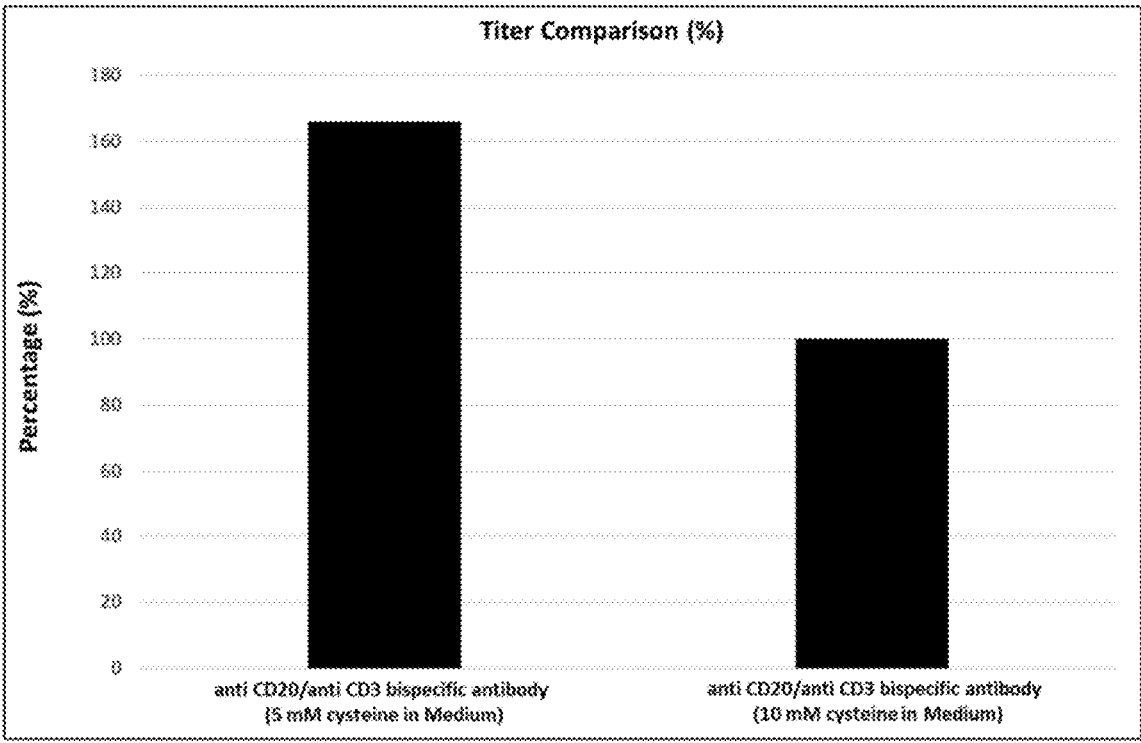
[Figure 7C]

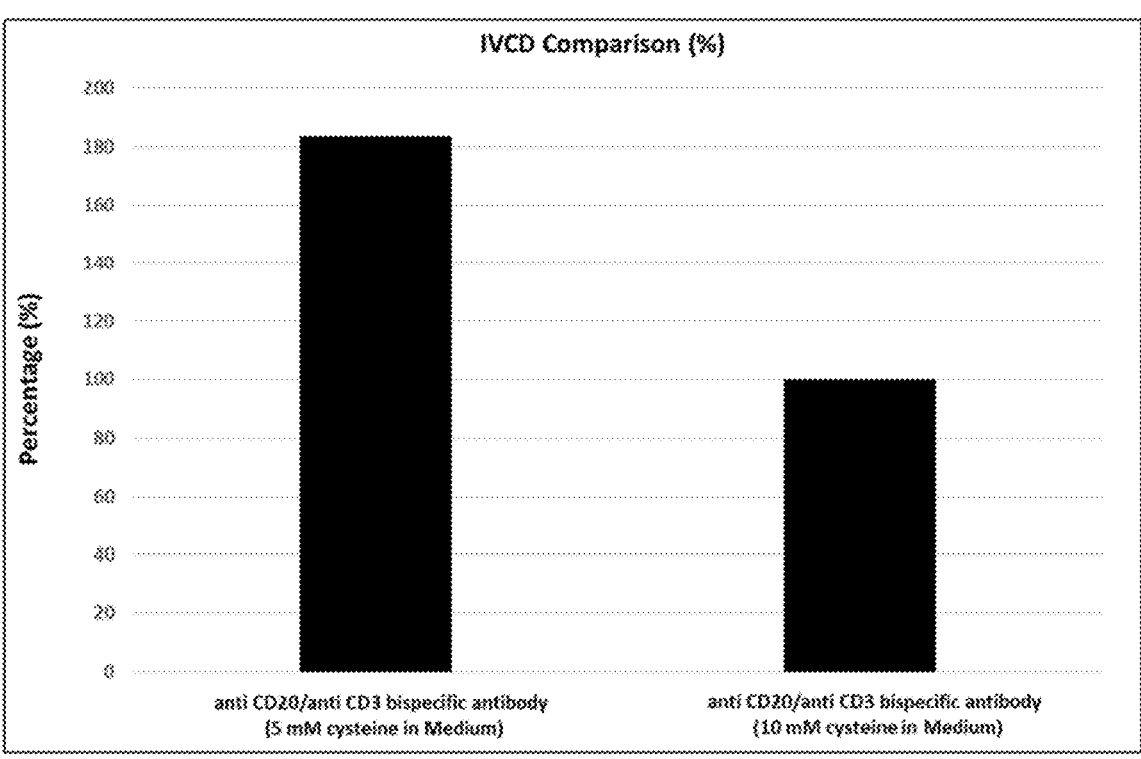
[Figure 7D]
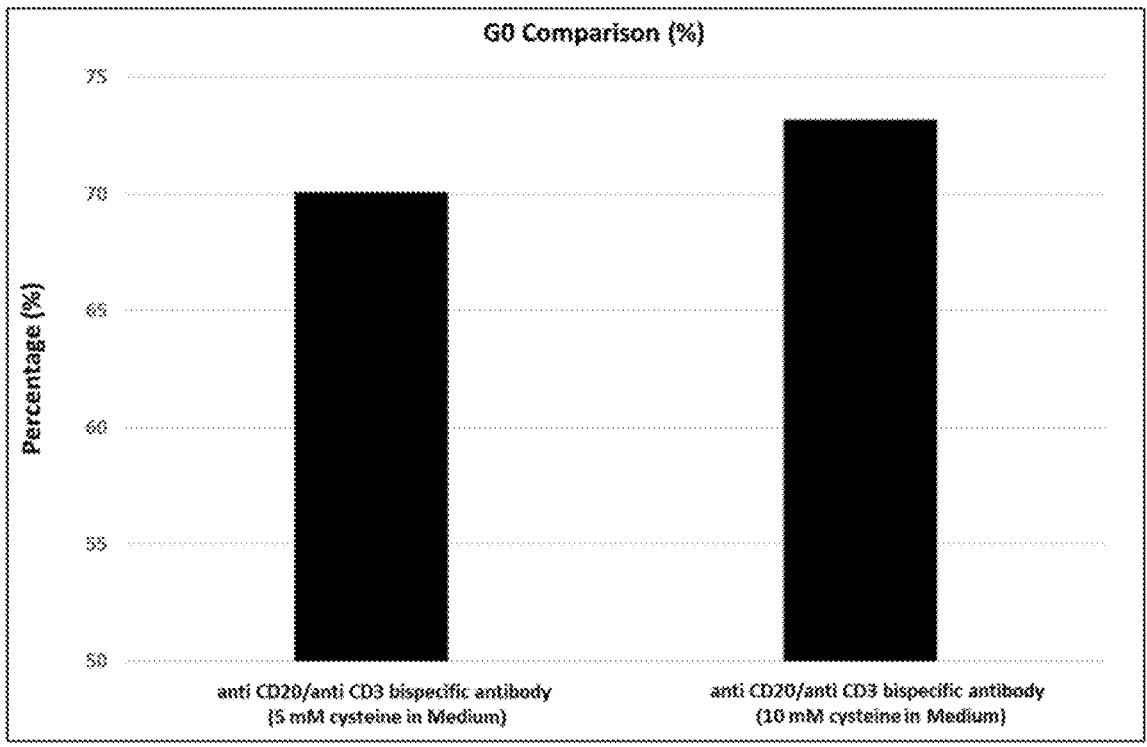
[Figure 8A]

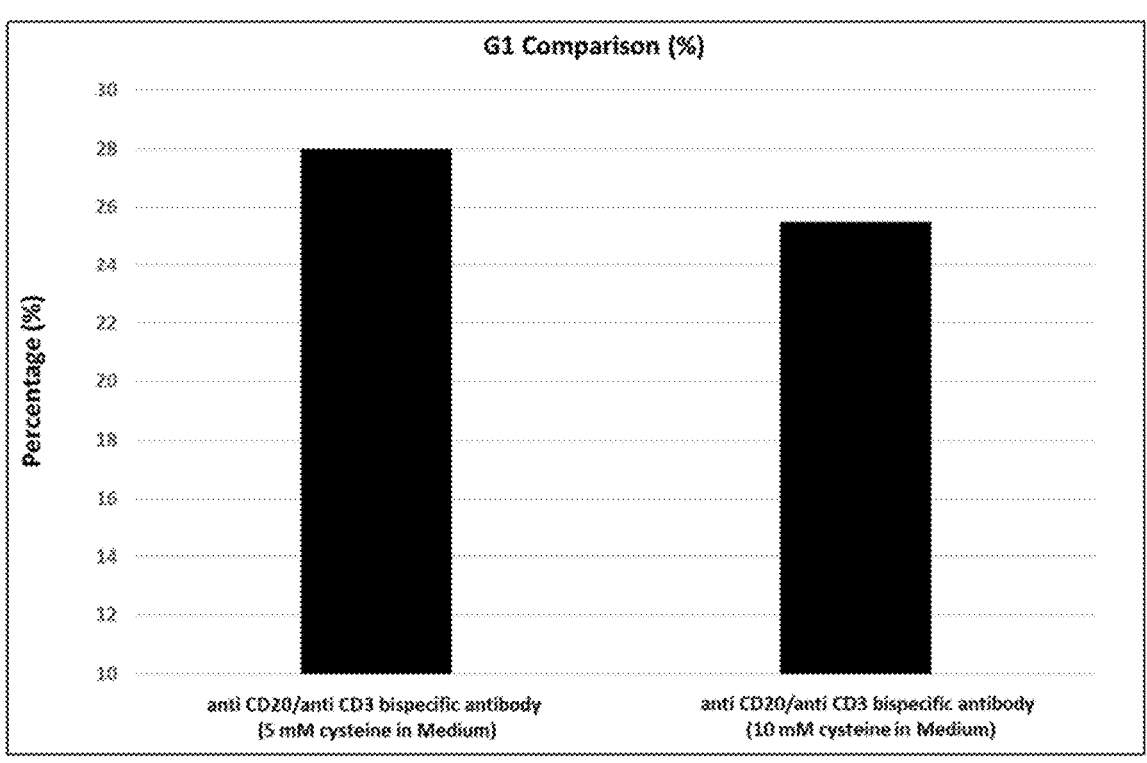
[Figure 8B]
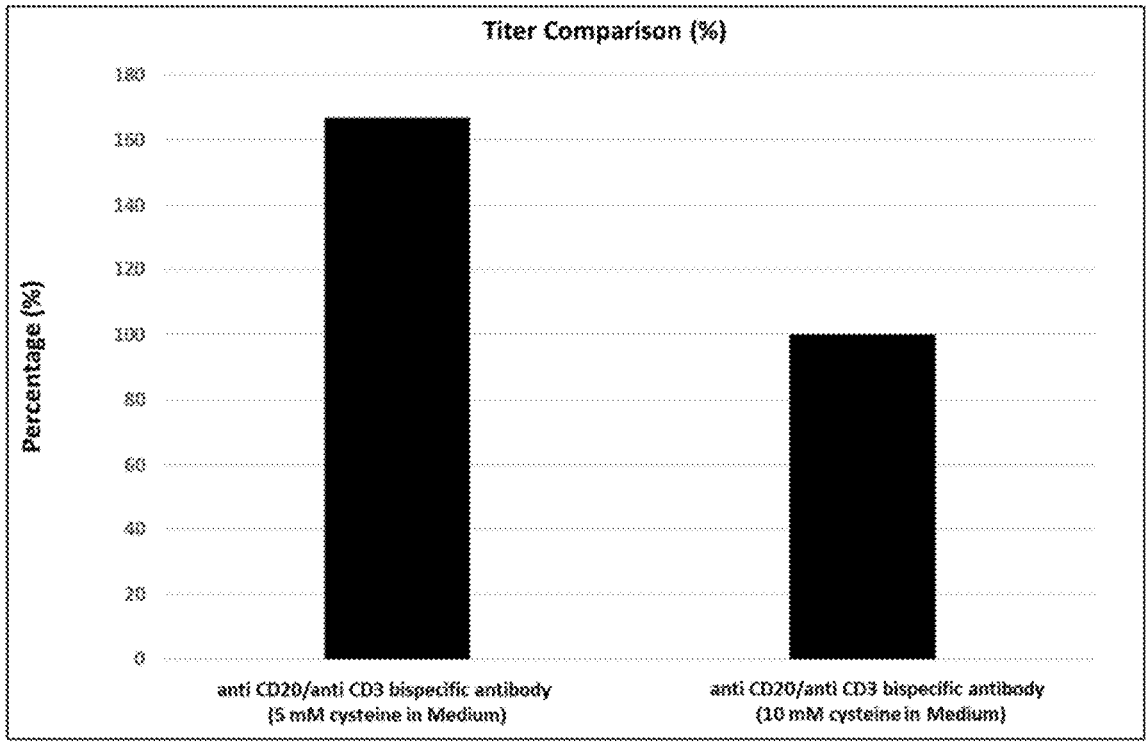
[Figure 8C]

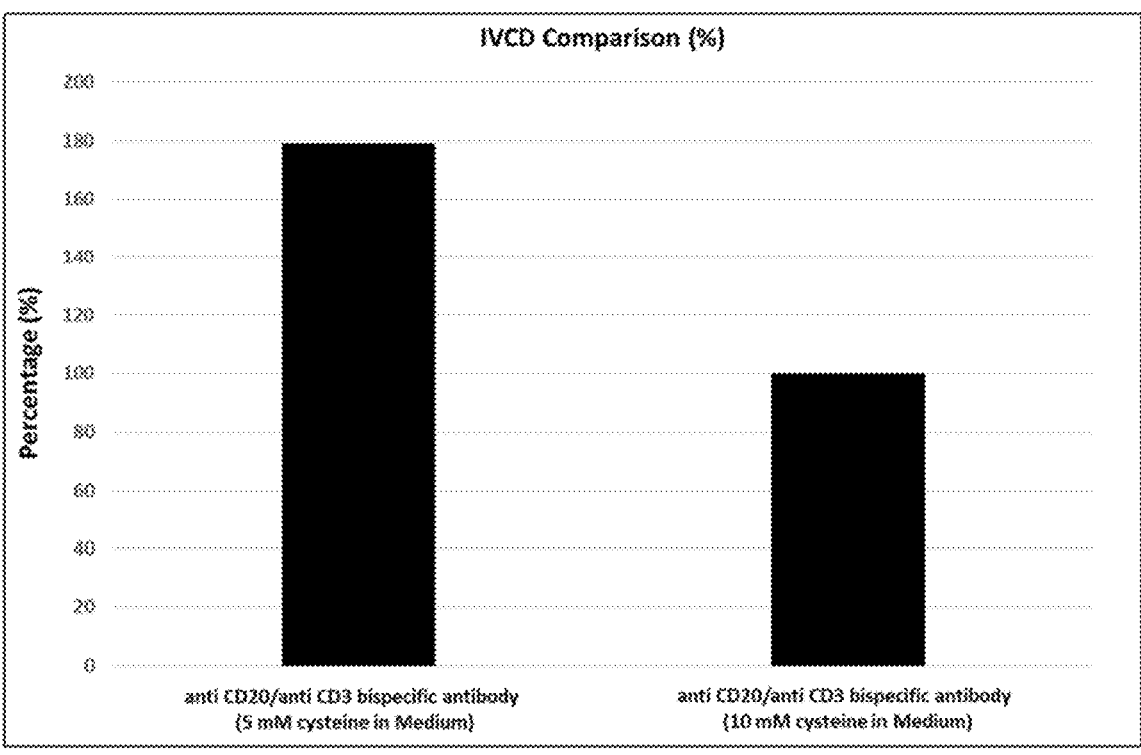
[Figure 8D]
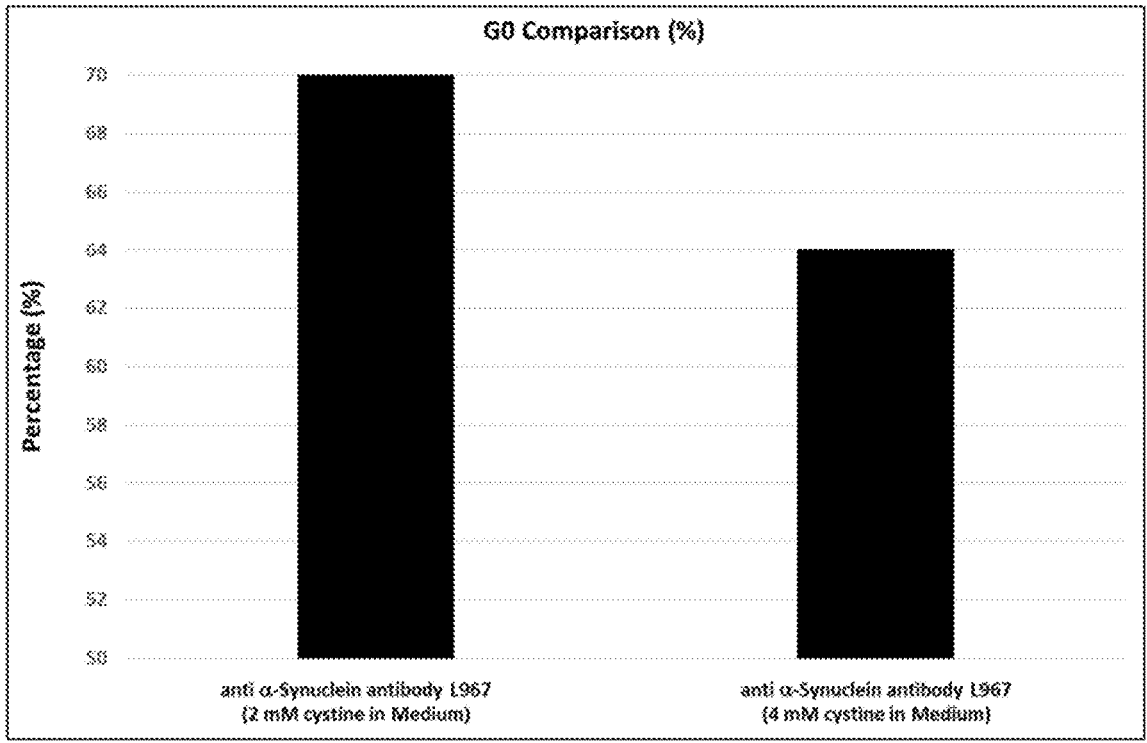
[Figure 9A]

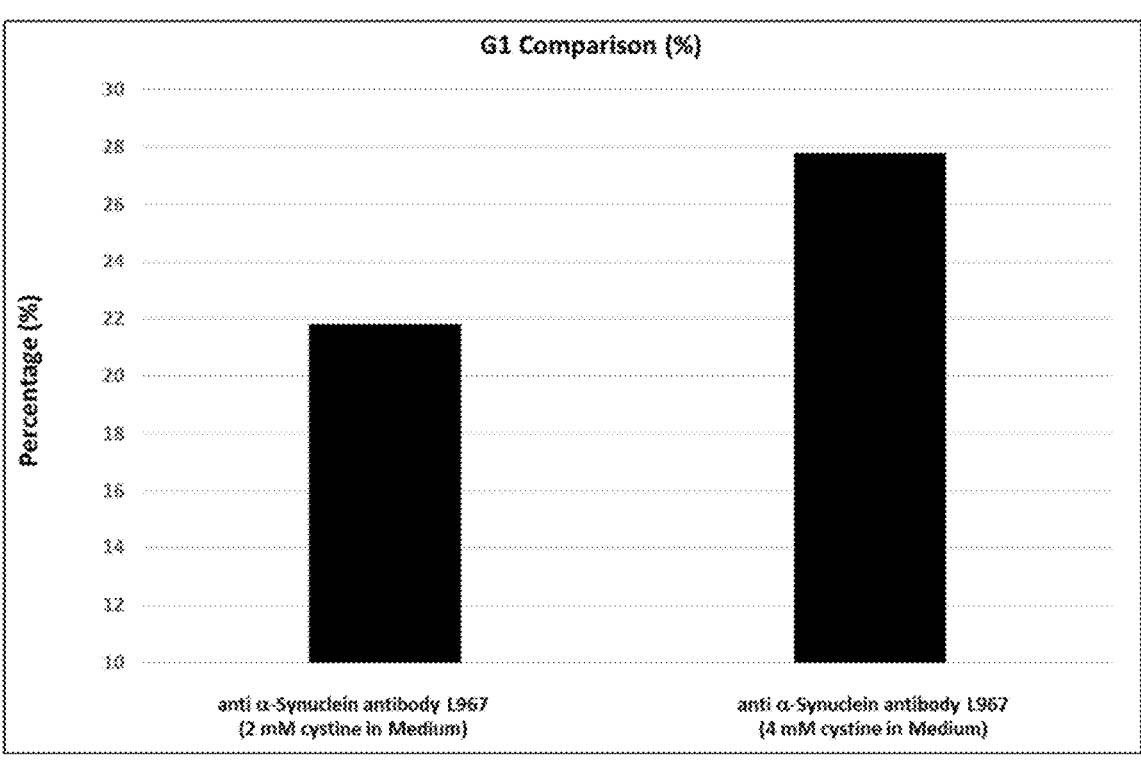
[Figure 9B]
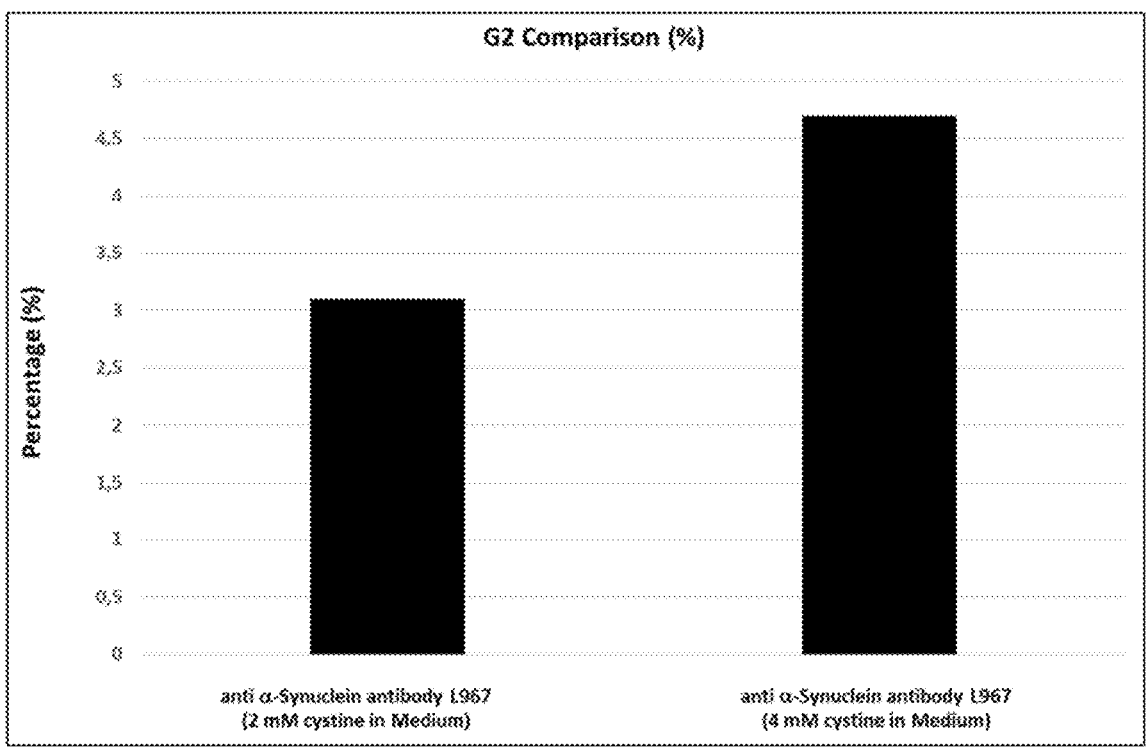
[Figure 9C]

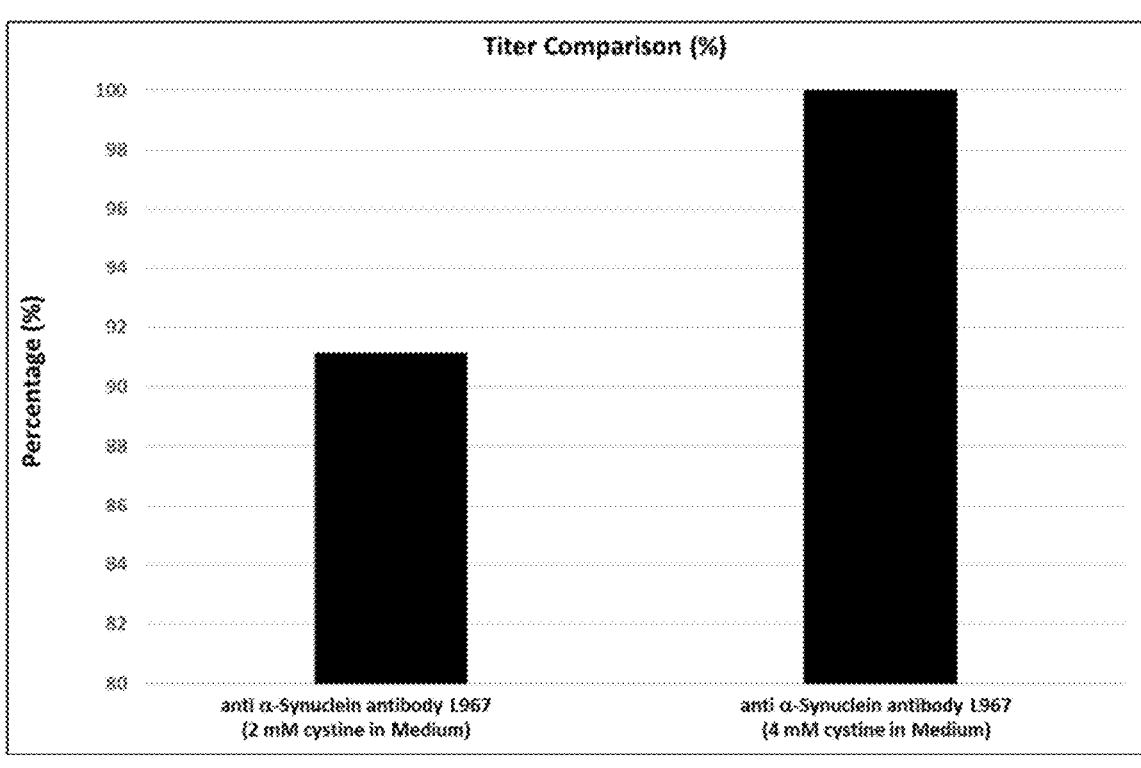
[Figure 9D]
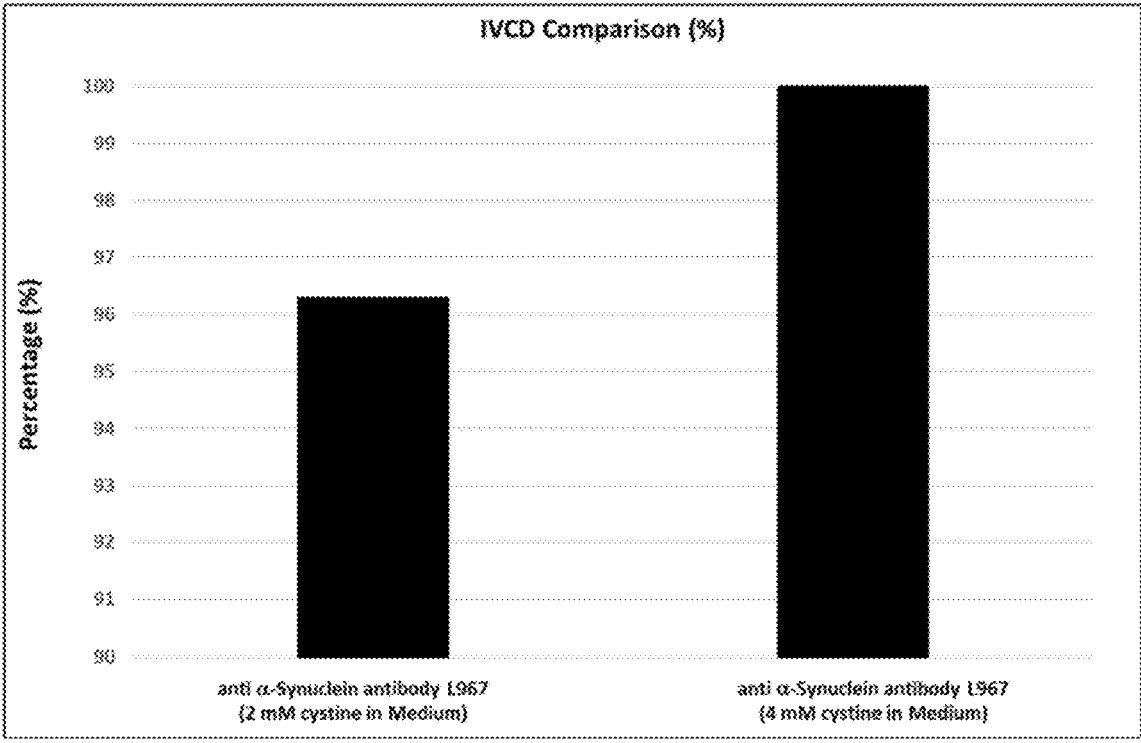
[Figure 9E]

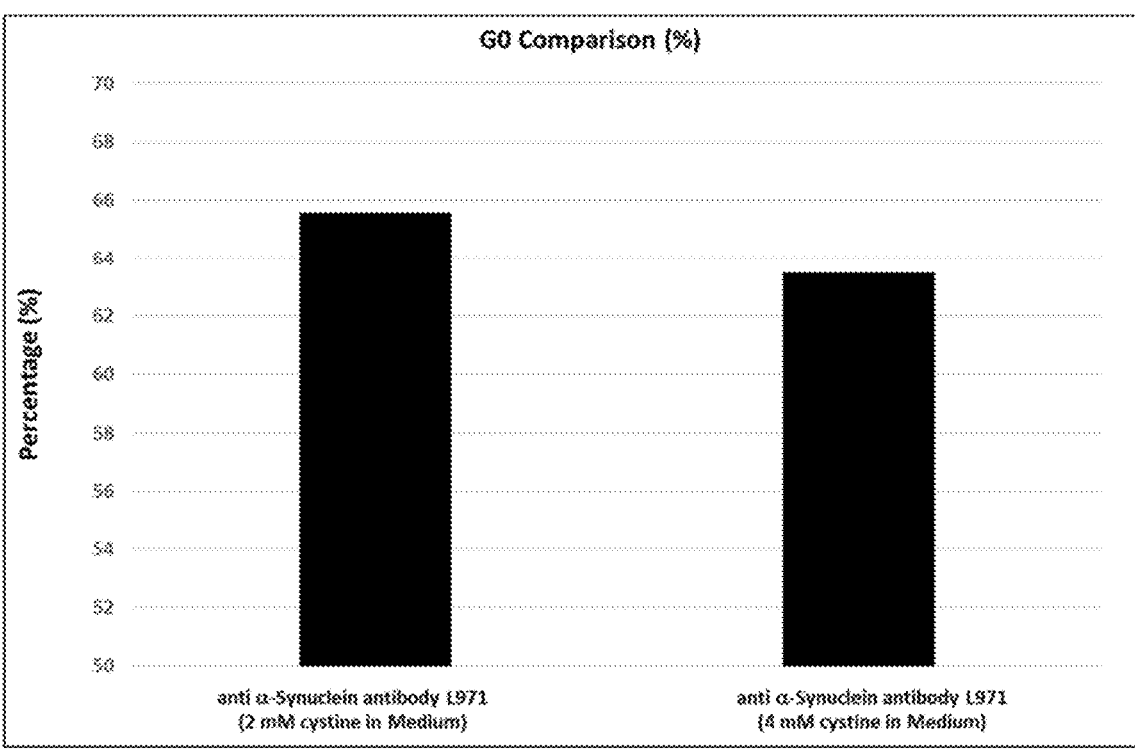
[Figure 10A]
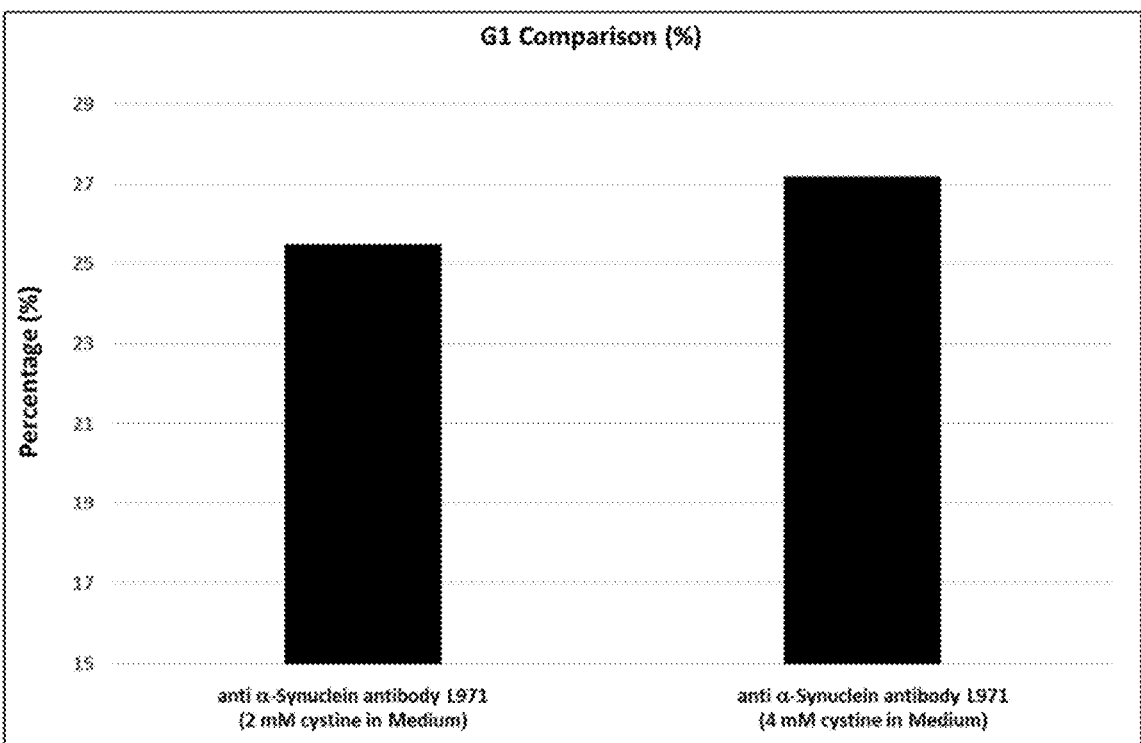
[Figure 10B]

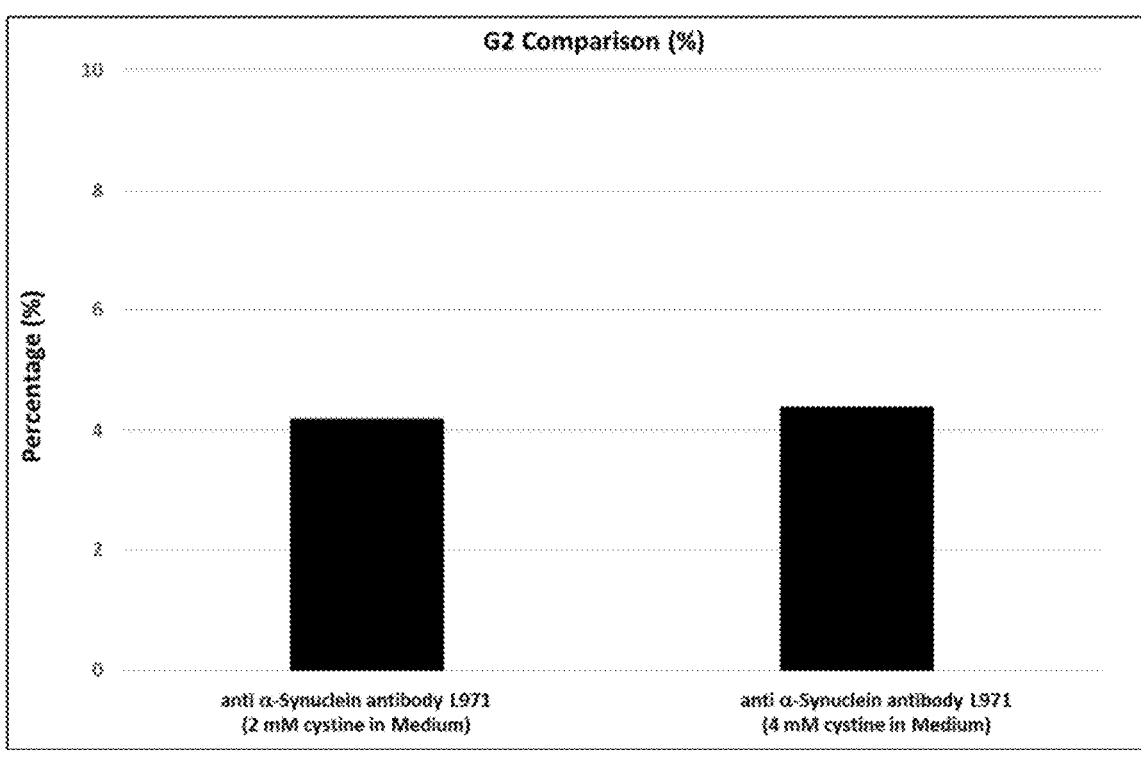
[Figure 10C]
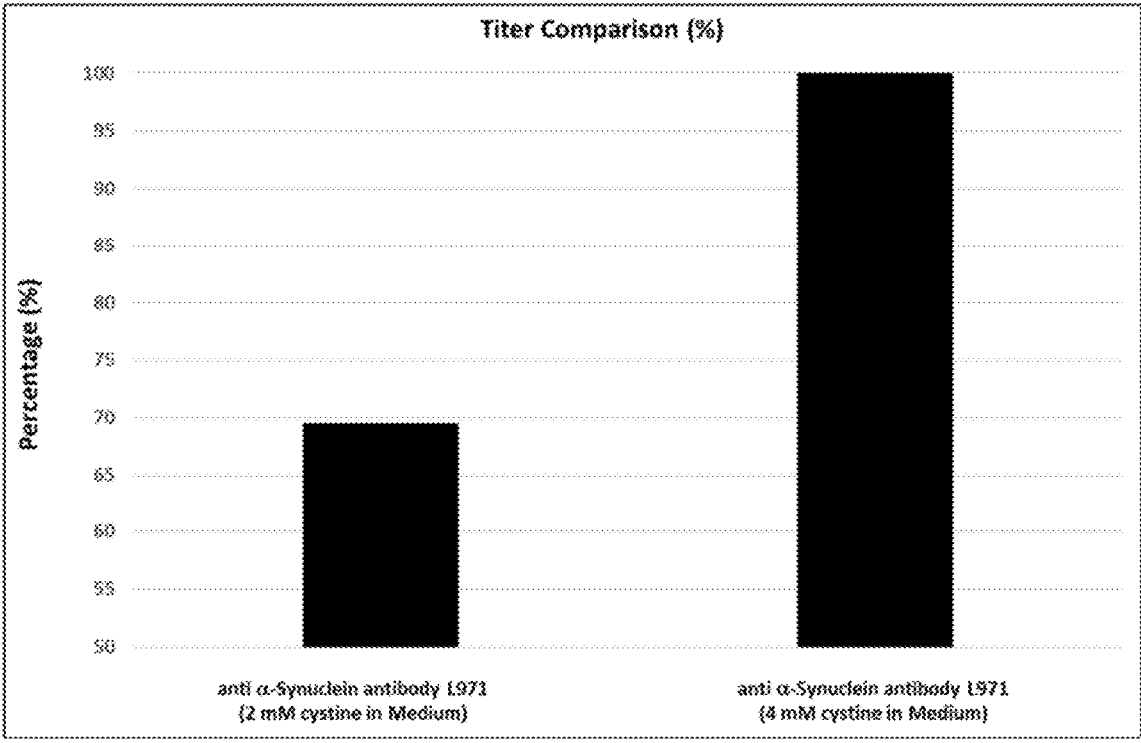
[Figure 10D]

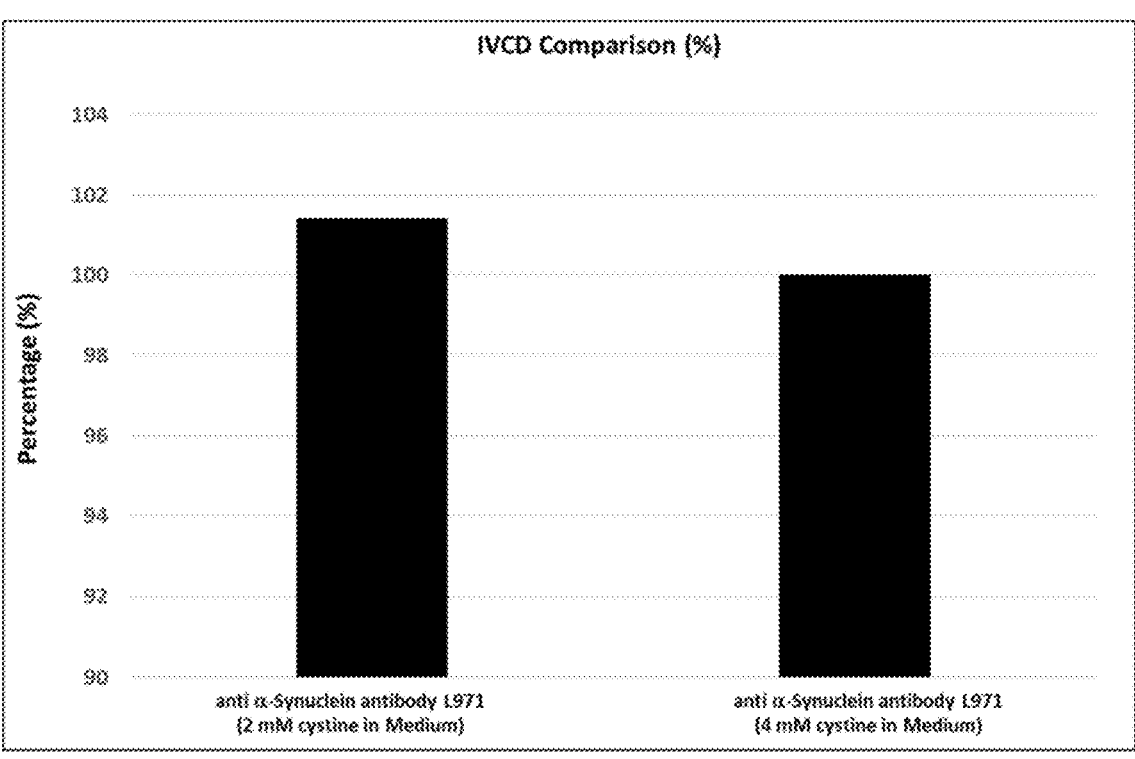
[Figure 10E]
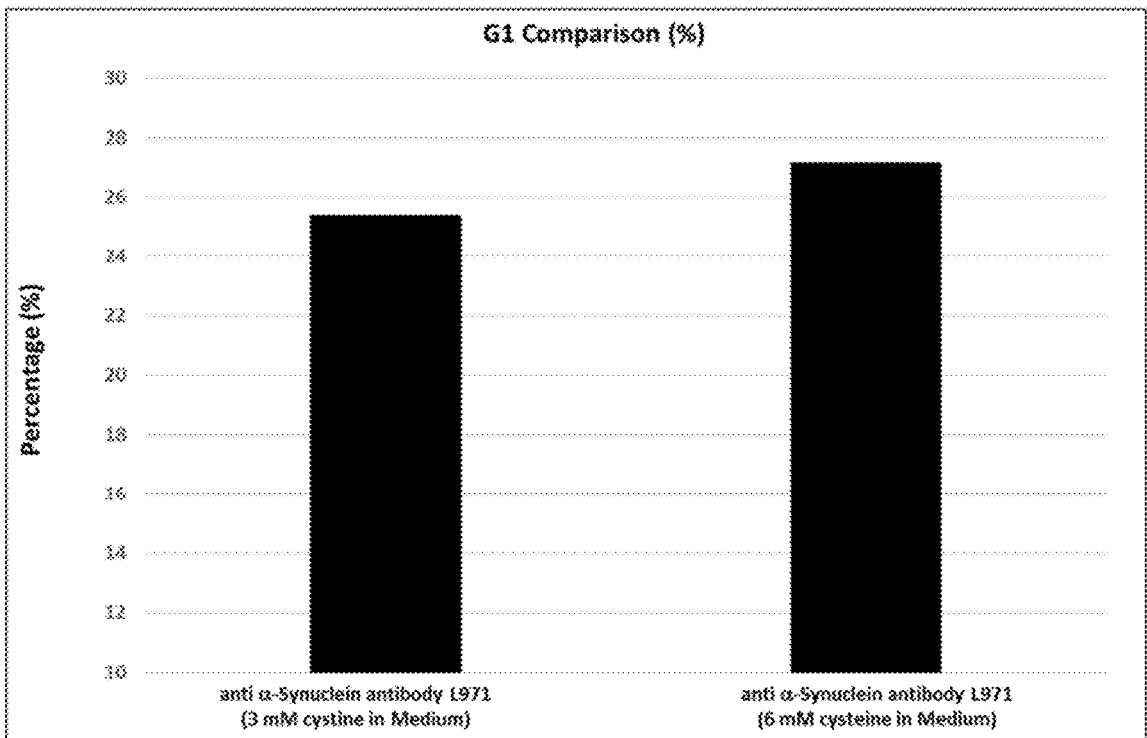
[Figure 11A]

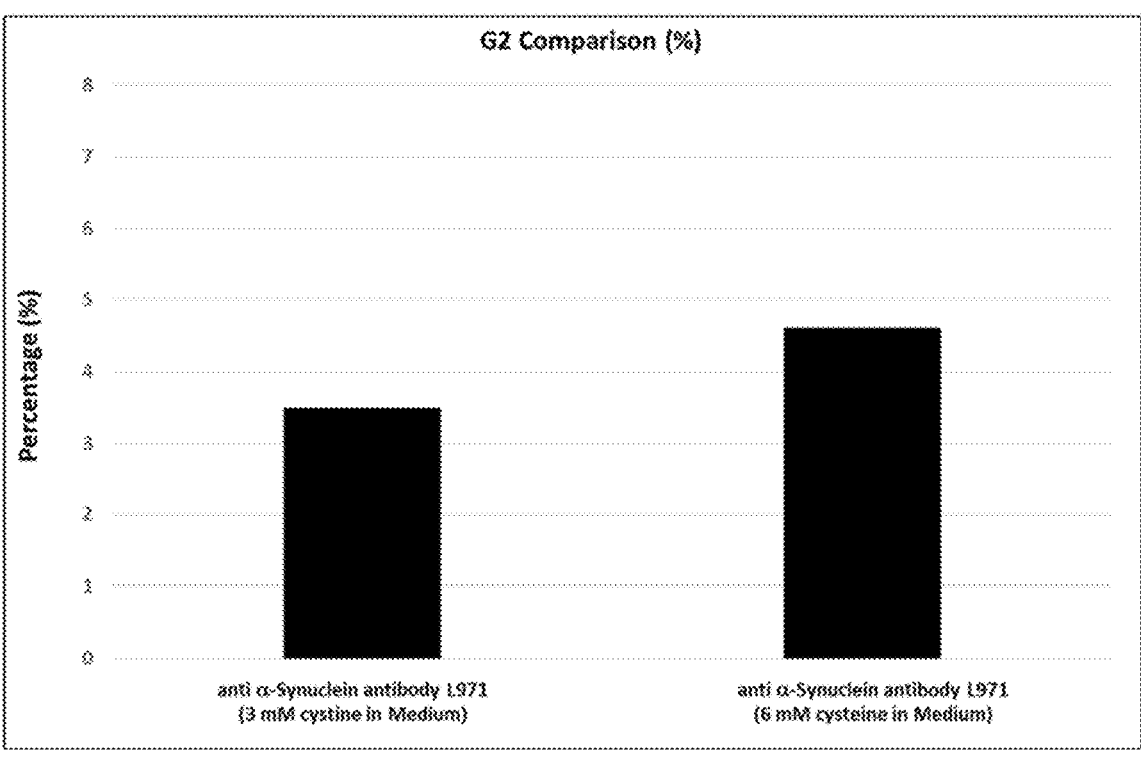
[Figure 11B]
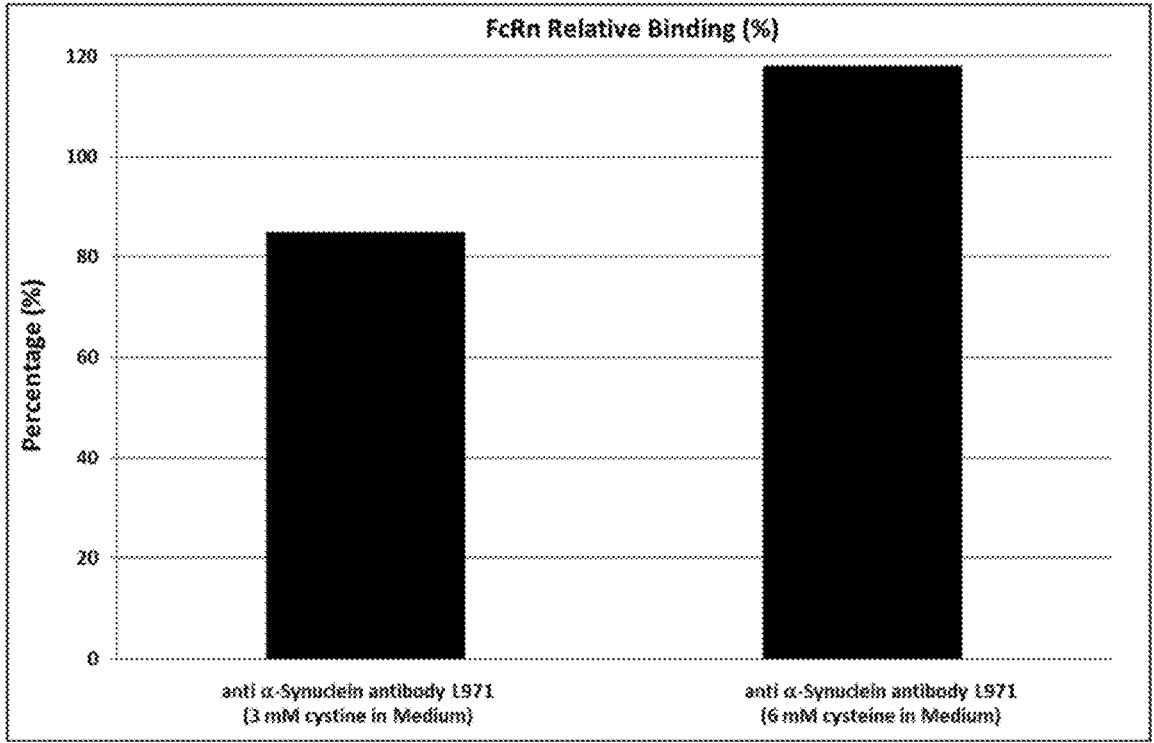
[Figure 11C]

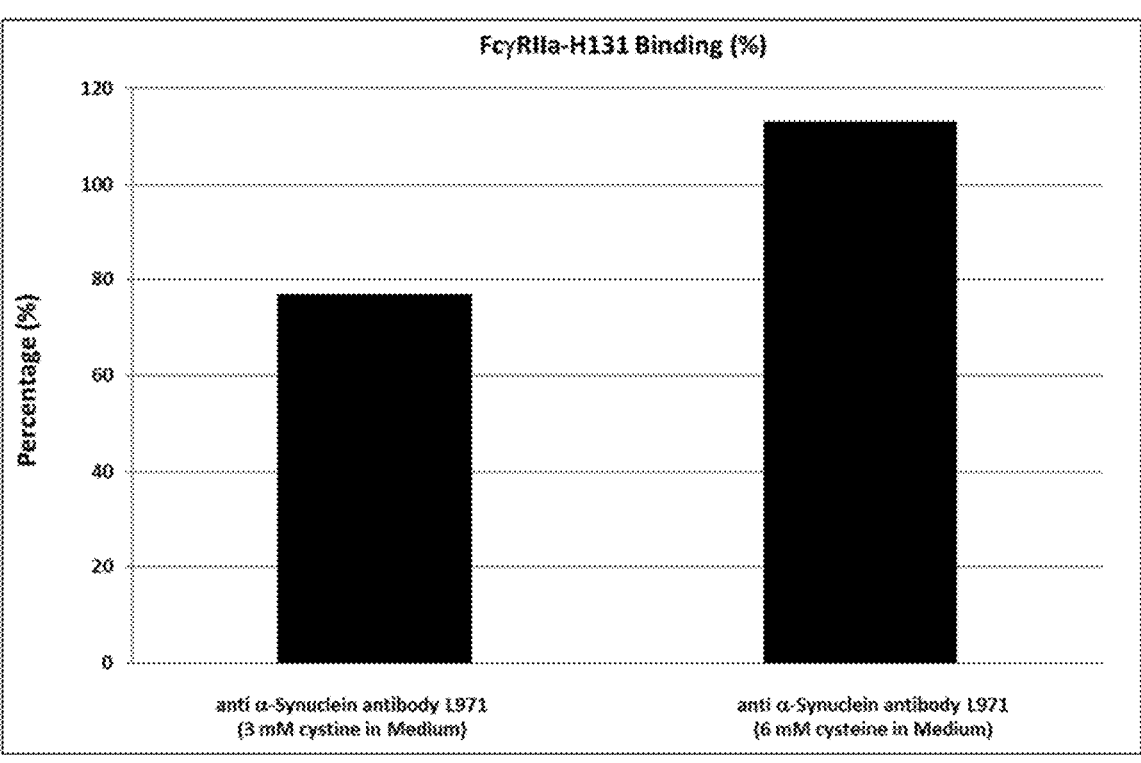
[Figure 11D]
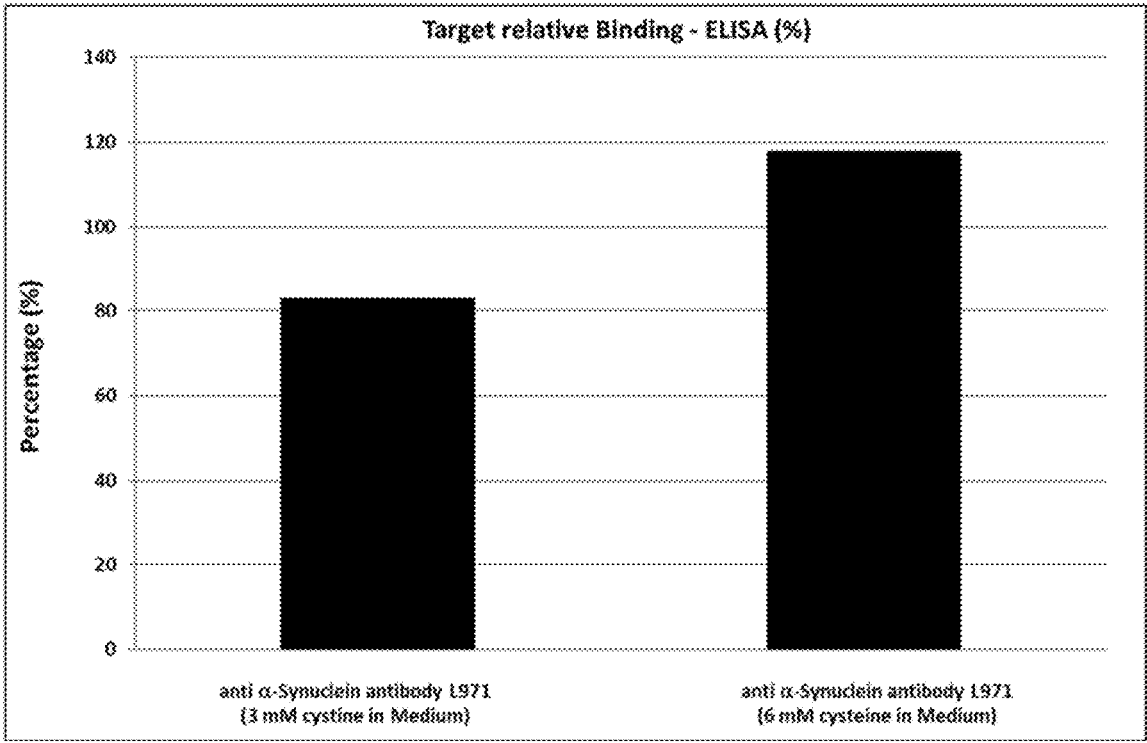
[Figure 11E]

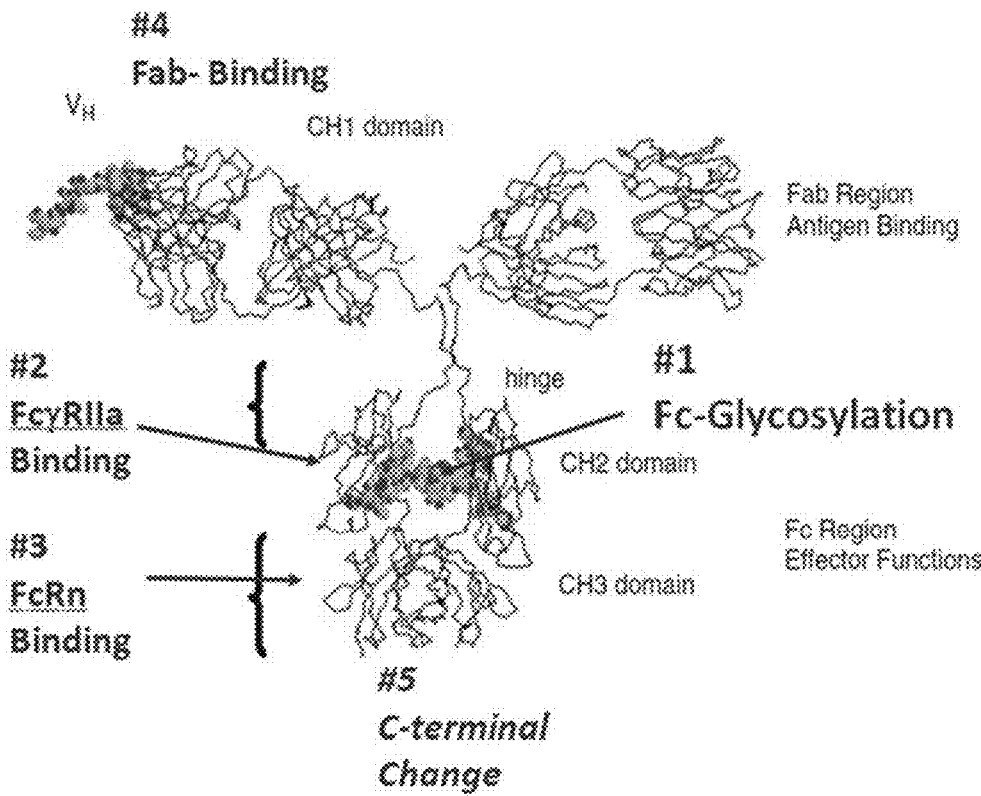
[Figure 12]

SEQUENCE LISTING

<160> NUMBER OF SEQ ID NOS: 47

<210> SEQ ID NO 1
<211> LENGTH: 1047
<212> TYPE: DNA
<213> ORGANISM: Artificial Sequence
<220> FEATURE:
<223> OTHER INFORMATION: The cDNA sequence of UDP-glucose 4-epimerase in CHO K1M

<400> SEQUENCE: 1

```
atggccgaga aggtgctggt cacaggcgga gctggctaca ttggcagcca cacggtactg      60
gagctgctgg aggcaggcta cgcccctgtg gtcatcgaca acttccataa tgccattcgt     120
ggaggggatt ccatgcctga gagcctgcgg cgggtccagg aactgacagg ccgctctgtg     180
gagtttgagg agatggacat cttggaccag gcagcgctac agcacctctt taagaagcac     240
agctttaagg ctgtcatcca ctttgctggg ctcaaggctg tgggcgagtc ggtgcagaag     300
cctctggatt attatagagt taacctaaca gggaccatcc agcttctgga gatcatgagg     360
gcccacgggt gaagaatct cgtgttcagc agctcagcca ccgtgtatgg gaatccccag     420
tacctgcctc tggatgaggc ccacccacc gggggttgta ccaacccta tggaaagtcc     480 aagttcttca tcgaggagat ggtccgggac ctgtgccggg cagattcggc ctggaacgca     540
gtgctgctac gctacttcaa tcccacgggt gcccacgcct ctggccgcat cggcgaggat     600
ccccagggcg tccccaacaa cctcatgccc tatgtctccc aggtggcaat tgggcgacga     660
gaggccctga atgtctttgg tggtgactat gatacagagg atggcacagg tgtaagggat     720
tacattcatg tggtggatct ggcgaagggc cacatcgcag ccttgaagaa gctgaaggag     780
caatgtggtt gccggatcta caacctgggc acaggcacag gctactctgt cctgcagatg     840
gtccaagcaa tggagaaggc ttcagggaag aagatcccat acaaggtggt ggcacggcgg     900
gaaggtgacg tggcagcctg ttatgccaac cccagcctgg cccatgagga gctgggctgg     960
```
acagcagcct tggggctgga caggatgtgt gaagatctat ggcgctggca gaagcagaac      1020
ccttcaggct ttggagcaca ggcctaa                                          1047

<210> SEQ ID NO 2
<211> LENGTH: 348
<212> TYPE: PRT
<213> ORGANISM: Artificial Sequence
<220> FEATURE:
<223> OTHER INFORMATION: [CDS]:1..1047 from SEQ ID NO 1

<400> SEQUENCE: 2

Met Ala Glu Lys Val Leu Val Thr Gly Gly Ala Gly Tyr Ile Gly Ser
1               5                   10                  15

His Thr Val Leu Glu Leu Leu Glu Ala Gly Tyr Ala Pro Val Val Ile
                20                  25                  30

Asp Asn Phe His Asn Ala Ile Arg Gly Gly Asp Ser Met Pro Glu Ser
            35                  40                  45

Leu Arg Arg Val Gln Glu Leu Thr Gly Arg Ser Val Glu Phe Glu Glu
        50                  55                  60

Met Asp Ile Leu Asp Gln Ala Ala Leu Gln His Leu Phe Lys Lys His
65                  70                  75                  80

Ser Phe Lys Ala Val Ile His Phe Ala Gly Leu Lys Ala Val Gly Glu
                85                  90                  95

Ser Val Gln Lys Pro Leu Asp Tyr Tyr Arg Val Asn Leu Thr Gly Thr
                100                 105                 110

Ile Gln Leu Leu Glu Ile Met Arg Ala His Gly Val Lys Asn Leu Val
            115                 120                 125

Phe Ser Ser Ser Ala Thr Val Tyr Gly Asn Pro Gln Tyr Leu Pro Leu
        130                 135                 140

Asp Glu Ala His Pro Thr Gly Gly Cys Thr Asn Pro Tyr Gly Lys Ser
145                 150                 155                 160

Lys Phe Phe Ile Glu Glu Met Val Arg Asp Leu Cys Arg Ala Asp Ser
                165                 170                 175

Ala Trp Asn Ala Val Leu Leu Arg Tyr Phe Asn Pro Thr Gly Ala His
                180                 185                 190

Ala Ser Gly Arg Ile Gly Glu Asp Pro Gln Gly Val Pro Asn Asn Leu
            195                 200                 205

Met Pro Tyr Val Ser Gln Val Ala Ile Gly Arg Arg Glu Ala Leu Asn
        210                 215                 220

Val Phe Gly Gly Asp Tyr Asp Thr Glu Asp Gly Thr Gly Val Arg Asp
225                 230                 235                 240

Tyr Ile His Val Val Asp Leu Ala Lys Gly His Ile Ala Ala Leu Lys
                245                 250                 255

Lys Leu Lys Glu Gln Cys Gly Cys Arg Ile Tyr Asn Leu Gly Thr Gly
                260                 265                 270

Thr Gly Tyr Ser Val Leu Gln Met Val Gln Ala Met Glu Lys Ala Ser
            275                 280                 285

Gly Lys Lys Ile Pro Tyr Lys Val Val Ala Arg Arg Glu Gly Asp Val
        290                 295                 300

Ala Ala Cys Tyr Ala Asn Pro Ser Leu Ala His Glu Glu Leu Gly Trp
305                 310                 315                 320

Thr Ala Ala Leu Gly Leu Asp Arg Met Cys Glu Asp Leu Trp Arg Trp
                325                 330                 335

Gln Lys Gln Asn Pro Ser Gly Phe Gly Ala Gln Ala
                340                 345

-continued

```
<210> SEQ ID NO 3
<211> LENGTH: 1140
<212> TYPE: DNA
<213> ORGANISM: Artificial Sequence
<220> FEATURE:
<223> OTHER INFORMATION: The cDNA sequence of UDP--D-glucose:
      -D-galactose-1-phosphateuridylyltransferase in CHO K1M

<400> SEQUENCE: 3
atgtcgcaaa acggagatga tcctgagcag cgccagcagg cgtcagaggc ggacgccatg      60
gcagcgacct tccgggcgag cgaacaccag catattcgct acaatccgct ccaggatgag     120
tgggtgttag tgtcggccca tcgcatgaag cggccctggc aaggacaagt ggagccccag     180
cttctgaaga cagtgccccg ctatgaccca ctcaaccctc tgtgtccggg gccacacga     240 gccaatgggg aggtgaatcc acactatgac agcaccttcc tgtttgacaa tgacttccca     300
gctctgcagc ccgatgctcc ggatccagga cccagtgacc atcctctttt tcgagcagag     360
gcggccagag gagtttgtaa ggtcatgtgc ttccatccct ggtcggatgt gacactgcca     420
ctcatgtcag tccctgagat ccgagctgtc atcgatgcct gggcttcagt caccgaggat     480
ctgggtgccc agtatccttg ggtgcagatc tttgaaaaca aaggagccat gatgggctgt     540
tctaaccccc accccactg ccaggtttgg gccagcagtt tcctgccaga tattgcccag     600
cgtgaagtgc gatcccagca gaactatcac agccagcatg gagaacctct gttactggaa     660
tatggccgcc aagaactcct caggaaggaa cgtctggtct tatctagtga gcactggcta     720
gtcctggttc ccttctgggc agtgtgggct ttccagacac tactgctgcc ccgccggcat     780
gtacgtcggc tacctgagct gacccctgct gaacgtgatg atctagcctc catcatgaag     840
aagctattga ccaagtatga caacctattt gagacatctt ttccctactc catgggctgg     900 catgggctc ccacgggatt aaagactgga gccgcctatg accactggca gctacatgct     960
cattactatc ccccactcct gcgctctgct actgtccgga aattcatggt tggctatgaa    1020
atgcttgccc atgggcaccg ggacctcact cctgaacagg ctgcagagag actaagggcg    1080
cttcctgagg tacattattg cctggcaaag aaagacaagg aaacagcagc tgttgcttga    1140
```

```
<210> SEQ ID NO 4
<211> LENGTH: 379
<212> TYPE: PRT
<213> ORGANISM: Artificial Sequence
<220> FEATURE:
<223> OTHER INFORMATION: [CDS]:1..1140 from SEQ ID NO 3

<400> SEQUENCE: 4

Met Ser Gln Asn Gly Asp Asp Pro Glu Gln Arg Gln Gln Ala Ser Glu
1               5                   10                  15

Ala Asp Ala Met Ala Ala Thr Phe Arg Ala Ser Glu His Gln His Ile
            20                  25                  30

Arg Tyr Asn Pro Leu Gln Asp Glu Trp Val Leu Val Ser Ala His Arg
        35                  40                  45

Met Lys Arg Pro Trp Gln Gly Gln Val Glu Pro Gln Leu Leu Lys Thr
    50                  55                  60

Val Pro Arg Tyr Asp Pro Leu Asn Pro Leu Cys Pro Gly Ala Thr Arg
65                  70                  75                  80

Ala Asn Gly Glu Val Asn Pro His Tyr Asp Ser Thr Phe Leu Phe Asp
                85                  90                  95

Asn Asp Phe Pro Ala Leu Gln Pro Asp Ala Pro Asp Pro Gly Pro Ser
```

-continued

```
              100              105              110

Asp His Pro Leu Phe Arg Ala Glu Ala Ala Arg Gly Val Cys Lys Val
        115              120              125

Met Cys Phe His Pro Trp Ser Asp Val Thr Leu Pro Leu Met Ser Val
    130              135              140

Pro Glu Ile Arg Ala Val Ile Asp Ala Trp Ala Ser Val Thr Glu Asp
145              150              155              160

Leu Gly Ala Gln Tyr Pro Trp Val Gln Ile Phe Glu Asn Lys Gly Ala
                165              170              175

Met Met Gly Cys Ser Asn Pro His Pro His Cys Gln Val Trp Ala Ser
                180              185              190

Ser Phe Leu Pro Asp Ile Ala Gln Arg Glu Val Arg Ser Gln Gln Asn
            195              200              205

Tyr His Ser Gln His Gly Glu Pro Leu Leu Leu Glu Tyr Gly Arg Gln
    210              215              220

Glu Leu Leu Arg Lys Glu Arg Leu Val Leu Ser Ser Glu His Trp Leu
225              230              235              240

Val Leu Val Pro Phe Trp Ala Val Trp Ala Phe Gln Thr Leu Leu Leu
                245              250              255

Pro Arg Arg His Val Arg Arg Leu Pro Glu Leu Thr Pro Ala Glu Arg
                260              265              270

Asp Asp Leu Ala Ser Ile Met Lys Lys Leu Leu Thr Lys Tyr Asp Asn
            275              280              285

Leu Phe Glu Thr Ser Phe Pro Tyr Ser Met Gly Trp His Gly Ala Pro
    290              295              300

Thr Gly Leu Lys Thr Gly Ala Ala Tyr Asp His Trp Gln Leu His Ala
305              310              315              320

His Tyr Tyr Pro Pro Leu Leu Arg Ser Ala Thr Val Arg Lys Phe Met
                325              330              335

Val Gly Tyr Glu Met Leu Ala His Gly His Arg Asp Leu Thr Pro Glu
                340              345              350

Gln Ala Ala Glu Arg Leu Arg Ala Leu Pro Glu Val His Tyr Cys Leu
            355              360              365

Ala Lys Lys Asp Lys Glu Thr Ala Ala Val Ala
    370              375
```

```
<210> SEQ ID NO 5
<211> LENGTH: 21
<212> TYPE: DNA
<213> ORGANISM: Artificial Sequence
<220> FEATURE:
<223> OTHER INFORMATION: forward primer UDP_GlcE-F2-21

<400> SEQUENCE: 5
atggccgaga aggtgctggt c                                          21

<210> SEQ ID NO 6
<211> LENGTH: 21
<212> TYPE: DNA
<213> ORGANISM: Artificial Sequence
<220> FEATURE:
<223> OTHER INFORMATION: reverse primer UDP_GlcE-R21

<400> SEQUENCE: 6
ttaggcctgt gctccaaagc c                                          21

<210> SEQ ID NO 7
```

-continued

```
<211> LENGTH: 21
<212> TYPE: DNA
<213> ORGANISM: Artificial Sequence
<220> FEATURE:
<223> OTHER INFORMATION: forward primer UDP-Gal-T-F2-21

<400> SEQUENCE: 7
atgtcgcaaa acggagatga t                                              21

<210> SEQ ID NO 8
<211> LENGTH: 18
<212> TYPE: DNA
<213> ORGANISM: Artificial Sequence
<220> FEATURE:
<223> OTHER INFORMATION: reverse primer UDP-Gal-T-R18

<400> SEQUENCE: 8
tcaagcaaca gctgctgt                                                  18

<210> SEQ ID NO 9
<211> LENGTH: 140
<212> TYPE: PRT
<213> ORGANISM: Artificial Sequence
<220> FEATURE:
<223> OTHER INFORMATION: Synthesized

<400> SEQUENCE: 9

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 10
<211> LENGTH: 5
<212> TYPE: PRT
<213> ORGANISM: Artificial Sequence
<220> FEATURE:
<223> OTHER INFORMATION: synuclein; CDR1 of heavy chain (CDR-H1)

<400> SEQUENCE: 10

Asn Tyr Gly Met Ser
1               5

<210> SEQ ID NO 11
<211> LENGTH: 17
<212> TYPE: PRT
<213> ORGANISM: Artificial Sequence
<220> FEATURE:
<223> OTHER INFORMATION: synuclein; CDR2 of heavy chain (CDR-H2)
```

<400> SEQUENCE: 11

Ser Ile Ser Ser Gly Gly Gly Ser Thr Tyr Tyr Pro Asp Asn Val Lys
1               5                   10                  15

Gly

<210> SEQ ID NO 12
<211> LENGTH: 7
<212> TYPE: PRT
<213> ORGANISM: Artificial Sequence
<220> FEATURE:
<223> OTHER INFORMATION: synuclein; CDR3 of heavy chain (CDR-H3)

<400> SEQUENCE: 12

Gly Gly Ala Gly Ile Asp Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: synuclein; CDR1 of light chain (CDR-L1)

<400> SEQUENCE: 13

Lys Ser Ile Gln Thr Leu Leu Tyr Ser Ser Asn Gln Lys Asn Tyr Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: synuclein; CDR2 of light chain (CDR-L2)

<400> SEQUENCE: 14

Trp Ala Ser Ile Arg Lys Ser
1               5

<210> SEQ ID NO 15
<211> LENGTH: 9
<212> TYPE: PRT
<213> ORGANISM: Artificial Sequence
<220> FEATURE:
<223> OTHER INFORMATION: synuclein; CDR3 of light chain (CDR-L3)

<400> SEQUENCE: 15

Gln Gln Tyr Tyr Ser Tyr Pro Leu Thr
1               5

<210> SEQ ID NO 16
<211> LENGTH: 116
<212> TYPE: PRT
<213> ORGANISM: Artificial Sequence
<220> FEATURE:
<223> OTHER INFORMATION: synuclein; heavy chain variable domain (VH)

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val

```
              35                    40                    45
Ala Ser Ile Ser Ser Gly Gly Gly Ser Thr Tyr Tyr Pro Asp Asn Val
     50                    55                    60

Lys Gly Arg Phe Thr Ile Ser Arg Asp Asp Ala Lys Asn Ser Leu Tyr
65                    70                    75                    80

Leu Gln Met Asn Ser Leu Arg Ala Glu Asp Thr Ala Val Tyr Tyr Cys
               85                    90                    95

Ala Arg Gly Gly Ala Gly Ile Asp Tyr Trp Gly Gln Gly Thr Leu Val
               100                   105                   110

Thr Val Ser Ser
         115
```

<210> SEQ ID NO 17
<211> LENGTH: 113
<212> TYPE: PRT
<213> ORGANISM: Artificial Sequence
<220> FEATURE:
<223> OTHER INFORMATION: synuclein; light chain variable domain (VL)

<400> SEQUENCE: 17

```
Asp Ile Gln Met Thr Gln Ser Pro Ser Ser Leu Ser Ala Ser Val Gly
1                 5                    10                   15

Asp Arg Val Thr Ile Thr Cys Lys Ser Ile Gln Thr Leu Leu Tyr Ser
               20                    25                    30

Ser Asn Gln Lys Asn Tyr Leu Ala Trp Phe Gln Gln Lys Pro Gly Lys
          35                    40                    45

Ala Pro Lys Leu Leu Ile Tyr Trp Ala Ser Ile Arg Lys Ser Gly Val
     50                    55                    60

Pro Ser Arg Phe Ser Gly Ser Gly Ser Gly Thr Asp Phe Thr Leu Thr
65                    70                    75                    80

Ile Ser Ser Leu Gln Pro Glu Asp Leu Ala Thr Tyr Tyr Cys Gln Gln
               85                    90                    95

Tyr Tyr Ser Tyr Pro Leu Thr Phe Gly Gly Gly Thr Lys Leu Glu Ile
               100                   105                   110

Lys
```

<210> SEQ ID NO 18
<211> LENGTH: 328
<212> TYPE: PRT
<213> ORGANISM: Artificial Sequence
<220> FEATURE:
<223> OTHER INFORMATION: synuclein; heavy chain constant domain (CH)

<400> SEQUENCE: 18

```
Ala Ser Thr Lys Gly Pro Ser Val Phe Pro Leu Ala Pro Ser Ser Lys
1                 5                    10                   15

Ser Thr Ser Gly Gly Thr Ala Ala Leu Gly Cys Leu Val Lys Asp Tyr
               20                    25                    30

Phe Pro Glu Pro Val Thr Val Ser Trp Asn Ser Gly Ala Leu Thr Ser
          35                    40                    45

Gly Val His Thr Phe Pro Ala Val Leu Gln Ser Ser Gly Leu Tyr Ser
     50                    55                    60

Leu Ser Ser Val Val Thr Val Pro Ser Ser Ser Leu Gly Thr Gln Thr
65                    70                    75                    80

Tyr Ile Cys Asn Val Asn His Lys Pro Ser Asn Thr Lys Val Asp Lys
               85                    90                    95

Arg Val Glu Pro Lys Ser Cys Asp Lys Thr His Thr Cys Pro Pro Cys
```

-continued

```
                100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

```
<210> SEQ ID NO 19
<211> LENGTH: 107
<212> TYPE: PRT
<213> ORGANISM: Artificial Sequence
<220> FEATURE:
<223> OTHER INFORMATION: synuclein; light chain constant domain (CL)

<400> SEQUENCE: 19
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 20
<211> LENGTH: 444
<212> TYPE: PRT
```

<213> ORGANISM: Artificial Sequence
<220> FEATURE:
<223> OTHER INFORMATION: synuclein; heavy chain (H)

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
```

-continued

```
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro
            435                 440

<210> SEQ ID NO 21
<211> LENGTH: 220
<212> TYPE: PRT
<213> ORGANISM: Artificial Sequence
<220> FEATURE:
<223> OTHER INFORMATION: synuclein; light chain (L)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
            85                  90                  95

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 22
<211> LENGTH: 5
<212> TYPE: PRT
<213> ORGANISM: Artificial Sequence
<220> FEATURE:
<223> OTHER INFORMATION: CD3; CDR1 of heavy chain (CDR-H1)

<400> SEQUENCE: 22

Thr Tyr Ala Met Asn
1               5

<210> SEQ ID NO 23
<211> LENGTH: 19
```

```
<212> TYPE: PRT
<213> ORGANISM: Artificial Sequence
<220> FEATURE:
<223> OTHER INFORMATION: CD3; CDR2 of heavy chain (CDR-H2)

<400> SEQUENCE: 23

Arg Ile Arg Ser Lys Tyr Asn Asn Tyr Ala Thr Tyr Tyr Ala Asp Ser
1               5                   10                  15

Val Lys Gly

<210> SEQ ID NO 24
<211> LENGTH: 14
<212> TYPE: PRT
<213> ORGANISM: Artificial Sequence
<220> FEATURE:
<223> OTHER INFORMATION: CD3; CDR3 of heavy chain (CDR-H3)

<400> SEQUENCE: 24

His Gly Asn Phe Gly Asn Ser Tyr Val Ser Trp Phe Ala Tyr
1               5                   10

<210> SEQ ID NO 25
<211> LENGTH: 14
<212> TYPE: PRT
<213> ORGANISM: Artificial Sequence
<220> FEATURE:
<223> OTHER INFORMATION: CD3; CDR1 of light chain (CDR-L1)

<400> SEQUENCE: 25

Gly Ser Ser Thr Gly Ala Val Thr Thr Ser Asn Tyr Ala Asn
1               5                   10

<210> SEQ ID NO 26
<211> LENGTH: 7
<212> TYPE: PRT
<213> ORGANISM: Artificial Sequence
<220> FEATURE:
<223> OTHER INFORMATION: CD3; CDR2 of light chain (CDR-L2)

<400> SEQUENCE: 26

Gly Thr Asn Lys Arg Ala Pro
1               5

<210> SEQ ID NO 27
<211> LENGTH: 9
<212> TYPE: PRT
<213> ORGANISM: Artificial Sequence
<220> FEATURE:
<223> OTHER INFORMATION: CD3; CDR3 of light chain (CDR-L3)

<400> SEQUENCE: 27

Ala Leu Trp Tyr Ser Asn Leu Trp Val
1               5

<210> SEQ ID NO 28
<211> LENGTH: 125
<212> TYPE: PRT
<213> ORGANISM: Artificial Sequence
<220> FEATURE:
<223> OTHER INFORMATION: CD3; heavy chain variable domain (VH)

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

-continued

```
Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 29
<211> LENGTH: 109
<212> TYPE: PRT
<213> ORGANISM: Artificial Sequence
<220> FEATURE:
<223> OTHER INFORMATION: CD3; light chain variable domain (VL)

<400> SEQUENCE: 29

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 30
<211> LENGTH: 101
<212> TYPE: PRT
<213> ORGANISM: Artificial Sequence
<220> FEATURE:
<223> OTHER INFORMATION: CD3; heavy chain constant domain (CH)

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
```

-continued

100

<210> SEQ ID NO 31
<211> LENGTH: 107
<212> TYPE: PRT
<213> ORGANISM: Artificial Sequence
<220> FEATURE:
<223> OTHER INFORMATION: CD3; light chain constant domain (CL)

<400> SEQUENCE: 31

Ala Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 101
<212> TYPE: PRT
<213> ORGANISM: Artificial Sequence
<220> FEATURE:
<223> OTHER INFORMATION: CD3 heavy chain constant domain (CD3 CH)

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys
            100

<210> SEQ ID NO 33
<211> LENGTH: 232
<212> TYPE: PRT
<213> ORGANISM: Artificial Sequence
<220> FEATURE:
<223> OTHER INFORMATION: CD3; light chain (L)

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

```
Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

```
<210> SEQ ID NO 34
<211> LENGTH: 5
<212> TYPE: PRT
<213> ORGANISM: Artificial Sequence
<220> FEATURE:
<223> OTHER INFORMATION: CD20; CDR1 of heavy chain (CDR-H1)

<400> SEQUENCE: 34

Tyr Ser Trp Ile Asn
1               5
```

```
<210> SEQ ID NO 35
<211> LENGTH: 17
<212> TYPE: PRT
<213> ORGANISM: Artificial Sequence
<220> FEATURE:
<223> OTHER INFORMATION: CD20; CDR2 of heavy chain (CDR-H2)

<400> SEQUENCE: 35

Arg Ile Phe Pro Gly Asp Gly Asp Thr Asp Tyr Asn Gly Lys Phe Lys
1               5                   10                  15

Gly
```

```
<210> SEQ ID NO 36
<211> LENGTH: 10
<212> TYPE: PRT
<213> ORGANISM: Artificial Sequence
<220> FEATURE:
<223> OTHER INFORMATION: CD20; CDR3 of heavy chain (CDR-H3)

<400> SEQUENCE: 36

Asn Val Phe Asp Gly Tyr Trp Leu Val Tyr
```

-continued

```
1               5                   10
```

<210> SEQ ID NO 37
<211> LENGTH: 16
<212> TYPE: PRT
<213> ORGANISM: Artificial Sequence
<220> FEATURE:
<223> OTHER INFORMATION: CD20; CDR1 of light chain (CDR-L1)

<400> SEQUENCE: 37

```
Arg Ser Ser Lys Ser Leu Leu His Ser Asn Gly Ile Thr Tyr Leu Tyr
1               5                   10                  15
```

<210> SEQ ID NO 38
<211> LENGTH: 7
<212> TYPE: PRT
<213> ORGANISM: Artificial Sequence
<220> FEATURE:
<223> OTHER INFORMATION: CD20; CDR2 of light chain (CDR-L2)

<400> SEQUENCE: 38

```
Gln Met Ser Asn Leu Val Ser
1               5
```

<210> SEQ ID NO 39
<211> LENGTH: 9
<212> TYPE: PRT
<213> ORGANISM: Artificial Sequence
<220> FEATURE:
<223> OTHER INFORMATION: CD20; CDR3 of light chain (CDR-L3)

<400> SEQUENCE: 39

```
Ala Gln Asn Leu Glu Leu Pro Tyr Thr
1               5
```

<210> SEQ ID NO 40
<211> LENGTH: 119
<212> TYPE: PRT
<213> ORGANISM: Artificial Sequence
<220> FEATURE:
<223> OTHER INFORMATION: CD20; heavy chain variable domain (VH)

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115
```

<210> SEQ ID NO 41
<211> LENGTH: 115
<212> TYPE: PRT

-continued

```
<213> ORGANISM: Artificial Sequence
<220> FEATURE:
<223> OTHER INFORMATION: CD20; light chain variable domain (VL)

<400> SEQUENCE: 41

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115

<210> SEQ ID NO 42
<211> LENGTH: 101
<212> TYPE: PRT
<213> ORGANISM: Artificial Sequence
<220> FEATURE:
<223> OTHER INFORMATION: CD20; heavy chain constant domain (CH)

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys
            100

<210> SEQ ID NO 43
<211> LENGTH: 104
<212> TYPE: PRT
<213> ORGANISM: Artificial Sequence
<220> FEATURE:
<223> OTHER INFORMATION: CD20; light chain constant domain (CL)

<400> SEQUENCE: 43

Ala Ala Pro Ser Val Phe Ile Phe Pro Pro Ser Asp Arg Lys Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
            35                  40                  45
```

Ser Gln Glu Ser Val Thr Glu Gln Asp Ser Lys Asp Ser Thr Tyr Ser
    50              55              60

Leu Ser Ser Thr Leu Thr Leu Ser Lys Ala Asp Tyr Glu Lys His Lys
65              70              75              80

Val Tyr Ala Cys Glu Val Thr His Gln Gly Leu Ser Ser Pro Val Thr
                85              90              95

Lys Ser Phe Asn Arg Gly Glu Cys
            100

<210> SEQ ID NO 44
<211> LENGTH: 219
<212> TYPE: PRT
<213> ORGANISM: Artificial Sequence
<220> FEATURE:
<223> OTHER INFORMATION: CD20 light chain (CD20 VL-CL)

<400> SEQUENCE: 44

Asp Ile Val Met Thr Gln Thr Pro Leu Ser Leu Pro Val Thr Pro Gly
1               5               10              15

Glu Pro Ala Ser Ile Ser Cys Arg Ser Ser Lys Ser Leu Leu His Ser
            20              25              30

Asn Gly Ile Thr Tyr Leu Tyr Trp Tyr Leu Gln Lys Pro Gly Gln Ser
        35              40              45

Pro Gln Leu Leu Ile Tyr Gln Met Ser Asn Leu Val Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Ala Gln Asn
                85              90              95

Leu Glu Leu Pro Tyr Thr Phe Gly Gly Gly Thr Lys Val Glu Ile Lys
            100             105             110

Arg Thr Val Ala Ala Pro Ser Val Phe Ile Phe Pro Pro Ser Asp Arg
            115             120             125

Lys Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
        195             200             205

Pro Val Thr Lys Ser Phe Asn Arg Gly Glu Cys
    210             215

<210> SEQ ID NO 45
<211> LENGTH: 447
<212> TYPE: PRT
<213> ORGANISM: Artificial Sequence
<220> FEATURE:
<223> OTHER INFORMATION: CD20 heavy chain [CD20 VH-CH1(EE)-Fc (hole,
    P329G LALA)]

<400> SEQUENCE: 45

Gln Val Gln Leu Val Gln Ser Gly Ala Glu Val Lys Lys Pro Gly Ser
1               5               10              15

-continued

Ser Val Lys Val Ser Cys Lys Ala Ser Gly Tyr Ala Phe Ser Tyr Ser
        20                      25                      30

Trp Ile Asn Trp Val Arg Gln Ala Pro Gly Gln Gly Leu Glu Trp Met
        35                      40                      45

Gly Arg Ile Phe Pro Gly Asp Gly Asp Thr Asp Tyr Asn Gly Lys Phe
        50                      55                      60

Lys Gly Arg Val Thr Ile Thr Ala Asp Lys Ser Thr Ser Thr Ala Tyr
65                      70                      75                      80

Met Glu Leu Ser Ser Leu Arg Ser Glu Asp Thr Ala Val Tyr Tyr Cys
                85                      90                      95

Ala Arg Asn Val Phe Asp Gly Tyr Trp Leu Val Tyr Trp Gly Gln Gly
                100                     105                     110

Thr Leu Val Thr Val Ser Ser Ala Ser Thr Lys Gly Pro Ser Val Phe
        115                     120                     125

Pro Leu Ala Pro Ser Ser Lys Ser Thr Ser Gly Gly Thr Ala Ala Leu
        130                     135                     140

Gly Cys Leu Val Glu Asp Tyr Phe Pro Glu Pro Val Thr Val Ser Trp
145                     150                     155                     160

Asn Ser Gly Ala Leu Thr Ser Gly Val His Thr Phe Pro Ala Val Leu
                165                     170                     175

Gln Ser Ser Gly Leu Tyr Ser Leu Ser Ser Val Val Thr Val Pro Ser
                180                     185                     190

Ser Ser Leu Gly Thr Gln Thr Tyr Ile Cys Asn Val Asn His Lys Pro
        195                     200                     205

Ser Asn Thr Lys Val Asp Glu Lys Val Glu Pro Lys Ser Cys Asp Lys
        210                     215                     220

Thr His Thr Cys Pro Pro Cys Pro Ala Pro Glu Ala Ala Gly Gly Pro
225                     230                     235                     240

Ser Val Phe Leu Phe Pro Pro Lys Pro Lys Asp Thr Leu Met Ile Ser
                245                     250                     255

Arg Thr Pro Glu Val Thr Cys Val Val Val Asp Val Ser His Glu Asp
                260                     265                     270

Pro Glu Val Lys Phe Asn Trp Tyr Val Asp Gly Val Glu Val His Asn
        275                     280                     285

Ala Lys Thr Lys Pro Arg Glu Glu Gln Tyr Asn Ser Thr Tyr Arg Val
        290                     295                     300

Val Ser Val Leu Thr Val Leu His Gln Asp Trp Leu Asn Gly Lys Glu
305                     310                     315                     320

Tyr Lys Cys Lys Val Ser Asn Lys Ala Leu Gly Ala Pro Ile Glu Lys
                325                     330                     335

Thr Ile Ser Lys Ala Lys Gly Gln Pro Arg Glu Pro Gln Val Cys Thr
                340                     345                     350

Leu Pro Pro Ser Arg Asp Glu Leu Thr Lys Asn Gln Val Ser Leu Ser
        355                     360                     365

Cys Ala Val Lys Gly Phe Tyr Pro Ser Asp Ile Ala Val Glu Trp Glu
        370                     375                     380

Ser Asn Gly Gln Pro Glu Asn Asn Tyr Lys Thr Thr Pro Pro Val Leu
385                     390                     395                     400

Asp Ser Asp Gly Ser Phe Phe Leu Val Ser Lys Leu Thr Val Asp Lys
                405                     410                     415

Ser Arg Trp Gln Gln Gly Asn Val Phe Ser Cys Ser Val Met His Glu
                420                     425                     430

Ala Leu His Asn His Tyr Thr Gln Lys Ser Leu Ser Leu Ser Pro

```
                435                 440                 445

<210> SEQ ID NO 46
<211> LENGTH: 439
<212> TYPE: PRT
<213> ORGANISM: Artificial Sequence
<220> FEATURE:
<223> OTHER INFORMATION: CD20-CD3 heavy chain [CD3 VL-CH1-Fc (knob,
      P329G LALA)]

<400> SEQUENCE: 46

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys Asp Lys Thr His Thr Cys Pro Pro Cys Pro
    210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
                340                 345                 350
```

```
Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
        370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro
        435
```

```
<210> SEQ ID NO 47
<211> LENGTH: 673
<212> TYPE: PRT
<213> ORGANISM: Artificial Sequence
<220> FEATURE:
<223> OTHER INFORMATION: CD20 heavy chain [CD20 VH-CH1(EE)-CD3 VL-CH1-Fc
      (knob, P329GLALA)]

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Glu Lys Val Glu Pro Lys Ser Cys Asp Gly
        210                 215                 220

Gly Gly Gly Gly Ser Gly Gly Gly Ser Gln Ala Val Val Thr Gln
225                 230                 235                 240

Glu Pro Ser Leu Thr Val Ser Pro Gly Gly Thr Val Thr Leu Thr Cys
                245                 250                 255

Gly Ser Ser Thr Gly Ala Val Thr Thr Ser Asn Tyr Ala Asn Trp Val
            260                 265                 270
```

```
Gln Glu Lys Pro Gly Gln Ala Phe Arg Gly Leu Ile Gly Gly Thr Asn
        275                 280                 285

Lys Arg Ala Pro Gly Thr Pro Ala Arg Phe Ser Gly Ser Leu Leu Gly
        290                 295                 300

Gly Lys Ala Ala Leu Thr Leu Ser Gly Ala Gln Pro Glu Asp Glu Ala
305                 310                 315                 320

Glu Tyr Tyr Cys Ala Leu Trp Tyr Ser Asn Leu Trp Val Phe Gly Gly
                325                 330                 335

Gly Thr Lys Leu Thr Val Leu Ser Ser Ala Ser Thr Lys Gly Pro Ser
                340                 345                 350

Val Phe Pro Leu Ala Pro Ser Ser Lys Ser Thr Ser Gly Gly Thr Ala
        355                 360                 365

Ala Leu Gly Cys Leu Val Lys Asp Tyr Phe Pro Glu Pro Val Thr Val
        370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
                420                 425                 430

Lys Pro Ser Asn Thr Lys Val Asp Lys Lys Val Glu Pro Lys Ser Cys
        435                 440                 445

Asp Lys Thr His Thr Cys Pro Pro Cys Pro Ala Pro Glu Ala Ala Gly
        450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
                500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
        530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Cys Arg Asp Glu Leu Thr Lys Asn Gln Val Ser
                580                 585                 590

Leu Trp Cys Leu Val Lys Gly Phe Tyr Pro Ser Asp Ile Ala Val Glu
                595                 600                 605

Trp Glu Ser Asn Gly Gln Pro Glu Asn Asn Tyr Lys Thr Thr Pro Pro
        610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
                660                 665                 670

Pro
```

ENZYME AND PATHWAY MODULATION WITH SULFHYDRYL COMPOUNDS AND THEIR DERIVATIVES

CROSS-REFERENCE TO RELATED APPLICATIONS

This application is the National Stage entry of International Application No. PCT/EP2021/060637, filed 23 Apr. 2021, which claims priority to European Patent Application No. 20171356.7, filed 24 Apr. 2020.

REFERENCE TO SEQUENCE LISTING SUBMITTED AS A COMPLIANT ASCII TEXT FILE (.xml)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2905193-034000.xml" created on 21 Oct. 2022, and 68,452 bytes in size) is submitted concurrently with the instant application, and the entire contents of the Sequence Listing are incorporated herein by reference.

BACKGROUND

Field

The present invention relates to proteins, particularly antibodies such as anti-CD20/anti-CD3 bispecific antibodies and anti-α-synuclein antibodies, having monogalactosylated (G1) and digalactosylated (G2) glycans. More particularly, the present invention relates to galactosylation engineering to generate proteins with improved therapeutic properties, including proteins with increased titer. Further, the invention relates to a cell culture medium and a mammalian cell as well as methods using said cell culture medium and said mammalian cell for producing said proteins. Moreover, the present invention relates to the use of said antibodies as a medicament such as for the treatment of cancer, particularly cancer associated with B-cells, or Parkinson's disease.

Description of Related Art

Many glycoproteins have been a major product of the biotechnology industry and have been exploited particularly for therapeutic purposes. Examples include erythropoietin (EPO), therapeutic monoclonal antibodies (therapeutic mAbs), tissue plasminogen activator (tPA), interferon-α, granulocyte-macrophage colony stimulating factor (GM-CSF), and human chorionic gonadotrophin (hCG) (Cumming et al., Glycobiology 1: 115-130 (1991)). Thereby, the oligosaccharide component of glycoproteins can affect their properties related to efficacy of therapeutic glycoproteins, including but not limited to physical stability, resistance to protease attack, interactions with the immune system, pharmacokinetics, and specific biological activity. Such properties may depend not only on the presence or absence, but also on the specific structures, of oligosaccharides.

Generally, immunoglobulins or antibodies in their native form are usually tetrameric glycoproteins composed of two light and two heavy chains. Such immunoglobulins commonly contain oligosaccharides at conserved positions in the heavy chain constant regions, which can variably affect protein assembly, secretion or functional activity (Boyd et al., (1995) Mol. Immunol. 32:1311-1318; Wittwer A., and Howard, S. C. (1990) Biochem. 29:4175-4180; Wright, A., and Morrison, S. L., Trends Biotech. 15:26-32 (1997)).

For example, increased galactosylation of antibodies might be functionally more anti-inflammatory as, e.g., described by a report by Karsten et al. (Nature Medicine 18.9 (2012) 1401-1406) showing in mice that high galactosylation of IgG immune complexes promotes the association of Fcγ RIIB and dectin-1, which blocks the pro-inflammatory effector functions of C5aR and CXCR226. Other reported effects of galactosylation on IgG molecules include modification of physicochemical properties such as conformation and surface accessibility (Krapp et al., J. Mol. Biol. 325 (2003) 979-89: Mimura et al., Mol. Immunol. 37 (2000) 697-706). Fortunato and Colina (J. Phys. Chem. 118 (2014) 9844-9851) used explicit water atomistic molecular dynamics simulations to study the effects of galactosylation in the Fc domain of immunoglobulin G1. They suggested glycosylation may be used as a route to improve the aggregation resistance of monoclonal antibodies for therapeutic treatments.

In view of the effect of different glycosylation level and/or glycosylation pattern of glycoproteins on their properties, in particular those related to therapeutic efficacy, it is important to ensure that the glycosylation pattern of glycoproteins produced in particular for clinical use is uniform and thus that the favorable properties of the antibodies are at least retained.

However, typically, expression of recombinant glycoproteins in host cells results in variations of the oligosaccharide structures attached at a particular glycosylation site such that the produced glycoproteins exist as multiple glycoforms. Thus, until now, it has been technically very challenging to precisely regulate and control glycosylation level and/or glycosylation pattern within production cells in vivo in a given therapeutic protein production process.

During the last decades, various methods have been proposed and several process parameters have been investigated that may alter the glycosylation pattern of glycoproteins in host cells including introducing or overexpressing certain enzymes in host cells which are involved in oligosaccharide production (U.S. Pat. Nos. 5,047,355, 5,510, 261), changes in oxygenation level, pH, purification schemes and the like (Werner, R. and Noe, W. (1993), Drug Res. 43:1134-1139; Werner, R. and Noe, W. (1993), Drug Res. 43:1242-1249; Hayter et al, (1992) Biotech, and Bioeng. 39:327-335; Borys et al., (1994) Biotech and Bioeng. 43:505-514; Borys et al., (1993) Bio/technology 11:720-724; Hearing et al., (1989) J. Cell Biol. 108:339-353; Goochee et al., in Frontiers in Bioprocessing II, Todd et al., eds (1992) American Chemical Society pp. 199-240; U.S. Pat. No. 5,096,816; Chotigeat, W, (1994) Cytotech. 15:217-221).

As outlined above, the production of glycoproteins with a desirable glycosylation level and/or glycosylation pattern is important for at least retaining and, optionally, optimizing favorable properties of said antibodies, particularly properties related to their therapeutic efficacy.

The technical problem is solved by provision of the embodiments provided herein below and characterized in the appended claims.

SUMMARY

During the past years, many efforts have been made to fundamentally understand and technically control protein galactosylation process in mammalian cells, such as CHO cells. Until now there are several general strategies which can be used to influence the extent of protein glycosylation, where the effects are often cell-type and product specific (Hossler et al., Glycobiology 19(9) (2009) 936-949; Hossler, Genomics and Systems Biology of Mammalian Cell Culture 127 (2012) 187-219): 1) improving activity of glycosyltransferases, 2) improving availability and activity of nucleotide sugar transporters for nucleotide sugar transfer, 3) increasing availability of nucleotide sugar substrates; and 4) reducing glycosidases on extracellular glycan degradation. Crowell et al. (Biotechnol Bioeng 96(3) (2007) 538-549) showed that supplementation of CHO cell cultures with manganese, the preferred co-factor of both the oligosaccharyltransferase complex and ß1,4-galactosyltransferase, increased site occupancy and ß1,4-galactosylation of rhEPO N-glycans in late-stage culture. Gramer et al., (Biotechnol Bioeng. 108(7) (2011) 1591-602)) reported that a synergistic combination of uridine, MnCl$_2$, and galactose significantly increased mAb galactosylation quantitatively with respect to the total UMG concentration supplied. Some approaches using over-expression and/or knockdown of glycosyltransferases and nucleotide sugar transporters (Jeong et al., J Microbiol Biotechnol 18(12) (2008) 1945-1952; Weikert et al., Nat Biotechnol 17(11) (1999) 1116-1121) have also been reported. Nucleotide sugar precursor feeding has been reported as a possible strategy to control glycosylation of recombinant proteins (Wong et al., Biotechnology and Bioengineering 107.2 (2010) 321-336). Specifically, the addition of galactose, glucosamine, and N-acetylmannosamine to cell culture media has been proven to increase intracellular nucleotide sugar levels. However, the effects of increased intracellular nucleotide sugar levels on glycosylation gene expression have not been well characterized. Moreover, the increase in intracellular nucleotide sugar levels did not necessarily lead to an improvement in glycosylation of the recombinant proteins. Some studies employed the strategy of knocking down cellular glycosidases (Ngantung et al., Biotechnol Bioeng. 95(1) (2006) 106-19) with the aim to improve protein glycosylation. However, this approach worked only from case to case. In summary, there is still a need for fundamental studies to investigate how various external factors influence intracellular galactosylation process.

As described herein, antibody galactosylation depends on the concentration of UDP-galactose present in cells as these sugar molecules act as substrates required for galactosylation. By this means, increase in UDP-galactose content has been found to be associated to higher galactosylation and sialylation of the antibody expressed in CHO cells. Varying UDP-galactose levels in the cells can have significant implications on glycan heterogeneity.

In this context, the UDP-glucose and UDP-galactose conversion pathway comprising two identified enzymes, uridine diphosphate α-D-glucose epimerase (UDP-Glc-E) and UDP-α-D-glucose: α-D-galactose-1-phosphate uridylyltransferase (UDP-Gal-T), was found to play a crucial role within the UDP-glucose and UDP-galactose conversion pathway in mammalian cells, such as CHO cells.

In this regard, UDP-Gal-T (EC 2.7.7.12) is a very special class of enzymes which can be regulated with several simple sulfhydryl molecules, such as L-cysteine, glutathione, 2-mercaptoethanol and DTT. In as early as 1966, Mayes and Hansen (Methods Enzymol. 9 (1966) 708-713) found out that L-cysteine can be used to activate and stimulate the enzymatic activity of partially purified UDP-Gal-T from calf liver. In the following years, Mayes (Arch. Biochem. Biophys. 172 (1976) 715-720) carried out extensive studies with completely purified UDP-Gal-T from calf liver and further confirmed this activation function of L-cysteine. Similar studies have also been carried out on UDP-Gal-T from other organisms. Saito et al. (J. Biol. Chem. 242 (1967) 2362-2368) demonstrated that L-cysteine stimulates the purified E. coli UDP-Gal-T to reach its maximum activity. Chowdhury (Indian J. Biochem. Biophys. 16 (1979) 273-277) also confirmed this observation with purified UDP-GAL-T from E. coli.

Thereby, it has been found by the present invention that it is possible to regulate and control intracellular UDP-galactose content and galactosylation of recombinant proteins, such as antibodies, during manufacturing process with sulfhydryl compounds or their derivatives. For example, it has been found by the present invention that it is possible to regulate and control N-glycan processing of recombinant monoclonal antibody during manufacturing process with sulfhydryl compounds or their derivatives to successfully and specifically manipulate the cell culture process for fine tuning of antibody galactosylation.

One peculiarity of the present invention is the use of the simple sulfhydryl molecules or compounds, such as L-cysteine, to modulate UDP-Gal-T in vivo activity in mammalian cell lines, such as CHO K1 and its derivative cell lines for producing a recombinant protein having monogalactosylated (G1) or digalactosylated (G2) glycans. In other words, the present invention provides new approaches to regulate gluco- and galacto-configured UDP-sugars in vivo, particularly through modulating the newly identified and specified conversion pathway with two enzymes, UDP-Gal-T and UDP-Glc-E, in mammalian cells, such as in CHO K1 and its derivative cell lines, for producing a recombinant protein having monogalactosylated (G1) or digalactosylated (G2) glycans. As shown in the Examples herein, it has been demonstrated that, by adjusting the relative media concentrations of certain sulfhydryl compounds or their derivatives, galactosylation of different antibodies can be precisely controlled in a high-yield, batch or fed-batch production process, with minimal impact on other glycoforms, other product quality attributes, or cell culture performance. Moreover, these data show that it is possible to precise regulation and control of a complex, dynamic cellular process at production scale for the definition of recombinant antibody product molecular heterogeneity and bioactivity. This enables an understanding of key effector interactions underpinning the knowledge-based design of cell culture media or feed composition to achieve a specified level of antibody galactosylation, whilst maximizing cell proliferation and productivity.

In particular, the present invention relates to anti-CD20/anti-CD3 bispecific antibody having monogalactosylated (G1) and digalactosylated (G2) glycans, the anti-CD20/anti-CD3 bispecific antibody comprising a first antigen binding domain, and a second antigen binding domain, wherein the first antigen binding domain comprises a heavy chain variable domain (VH) comprising (a) CDR-H1 comprising the amino acid sequence of SEQ ID NO: 22,
(b) CDR-H2 comprising the amino acid sequence of SEQ ID NO: 23, and
(c) CDR-H3 comprising the amino acid sequence of SEQ ID NO: 24, and
a light chain variable domain (VL) comprising
(d) CDR-L1 comprising the amino acid sequence of SEQ ID NO: 25,
(e) CDR-L2 comprising the amino acid sequence of SEQ ID NO: 26, and
(f) CDR-L3 comprising the amino acid sequence of SEQ ID NO: 27;

wherein the second antigen binding domain comprises a heavy chain variable domain (VH) comprising
(a) CDR-H1 comprising the amino acid sequence of SEQ ID NO: 34,
(b) CDR-H2 comprising the amino acid sequence of SEQ ID NO: 35, and
(c) CDR-H3 comprising the amino acid sequence of SEQ ID NO: 36; and
a light chain variable domain (VL) comprising
(d) CDR-L1 comprising the amino acid sequence of SEQ ID NO: 37,
(e) CDR-L2 comprising the amino acid sequence of SEQ ID NO: 38, and
(f) CDR-L3 comprising the amino acid sequence of SEQ ID NO: 39; and
wherein the anti-CD20/anti-CD3 bispecific antibody has 19.0-29.0% (w/w) of G1 and 1.3-2.8% (w/w) of G2 per total glycan; preferably 20.0-28.0% (w/w) of G1 and 1.4-2.7% (w/w) of G2 per total glycan; more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan. Preferably, the anti-CD20/anti-CD3 bispecific antibody is an antibody, wherein
(a) the first antigen binding domain comprises a VH sequence of SEQ ID NO: 28 and the second antigen binding domain comprises a VH sequence of SEQ ID NO: 40;
(b) the first antigen binding domain comprises a VL sequence of SEQ ID NO: 29 and the second antigen binding domain comprises a VL sequence of SEQ ID NO: 41; or
(c) the first and second antigen binding domain comprises a VH sequence as defined in (a) and a VL sequence as defined in (b).
More preferably, the anti-CD20/anti-CD3 bispecific antibody is an antibody, wherein
(a) a VH sequence of the first antigen binding domain has at least 95% sequence identity to the amino acid sequence of SEQ ID NO: 28 and a VH sequence of the second antigen binding domain has at least 95% sequence identity to the amino acid sequence of SEQ ID NO: 40;
(b) a VL sequence of the first antigen binding domain has least 95% sequence identity to the amino acid sequence of SEQ ID NO: 29 and a VL sequence of the second antigen binding domain has at least 95% sequence identity to the amino acid sequence of SEQ ID NO: 41; or
(c) the anti-CD20/anti-CD3 bispecific antibody comprises the VH sequence of the first and second antigen binding domain as defined in (a) and the VL sequence of the first and second antigen binding domain as defined in (b).
Even more preferably, the anti-CD20/anti-CD3 bispecific antibody is an antibody, wherein the anti-CD20/anti-CD3 bispecific antibody comprises
(a) a first heavy chain of SEQ ID NO: 46 and a second heavy chain of SEQ ID NO: 45
(b) a first light chain of SEQ ID NO: 33 and a second light chain of SEQ ID NO: 44; or
(c) the first heavy chain and the second heavy chain as defined in (a) and the first light chain and the second light chain as defined in (b).
Most preferably, the anti-CD20/anti-CD3 bispecific antibody is an antibody, wherein the anti-CD20/anti-CD3 bispecific antibody comprises (a) a first heavy chain of SEQ ID NO: 47 and a second heavy chain of SEQ ID NO: 45
(b) a first light chain of SEQ ID NO: 33, a second light chain and a third light chain of SEQ ID NO: 44; or
(c) the first heavy chain and the second heavy chain as defined in (a) and the first light chain, the second light chain and the third light chain as defined in (b).
Equally, the present invention relates to an anti α-synuclein antibody having monogalactosylated (G1) and digalactosylated (G2) glycans, the anti α-synuclein antibody comprising a heavy chain variable domain (VH) comprising
(a) CDR-H1 comprising the amino acid sequence of SEQ ID NO: 10,
(b) CDR-H2 comprising the amino acid sequence of SEQ ID NO: 11, and
(c) CDR-H3 comprising the amino acid sequence of SEQ ID NO: 12; and
a light chain variable domain (VL) comprising
(d) CDR-L1 comprising the amino acid sequence of SEQ ID NO: 13,
(e) CDR-L2 comprising the amino acid sequence of SEQ ID NO: 14, and
(f) CDR-L3 comprising the amino acid sequence of SEQ ID NO: 15; and
wherein the anti α-synuclein antibody has 17.2-48.0% (w/w) of G1 and 3.1-15.0% (w/w) of G2 per total glycan; preferably 25.4-48.0% (w/w) of G1 and 3.5-15.0% (w/w) of G2 per total glycan: preferably 27.2-47.0% of G1 and 4.4 to 15.0% of G2 per total glycan; preferably 40.0-46.0% (w/w) of G1 and 8.4-15.0% (w/w) of G2 per total glycan; more preferably 41.0-45.0% (w/w) of G1 and 9.5-14.0% (w/w) of G2 per total glycan and most preferably 42.1-43.9% (w/w) of G1 and 10.6-13.3% (w/w) of G2 per total glycan.
Preferably, the anti α-synuclein antibody comprises
(a) a VH sequence of SEQ ID NO: 16;
(b) a VL sequence of SEQ ID NO: 17; or
(c) the VH sequence as defined in (a) and the VL sequence as defined in (b).
More preferably, the anti α-synuclein antibody comprises
(a) a VH sequence having at least 95% sequence identity to the amino acid sequence of SEQ ID NO: 16;
(b) a VL sequence having at least 95% sequence identity to the amino acid sequence of SEQ ID NO: 17; or
(c) the VH sequence as defined in (a) and the VL sequence as defined in (b).
Even more preferably, the anti α-synuclein antibody comprises a heavy chain of SEQ ID NO: 20 and a light chain of SEQ ID NO: 21.
Preferably, the monogalactosylated (G1) and digalactosylated (G2) glycans of the anti-CD20/anti-CD3 bispecific antibody or the anti α-synuclein antibody as disclosed in the context of the invention are associated with N-acetylglucosamine.
Equally, the present invention relates to a cell culture medium for producing an antibody as disclosed in the context of the invention having monogalactosylated (G1) and digalactosylated (G2) glycans in a mammalian cell, the cell culture medium comprising a concentration of more than 4.0 mM and less than 10.0 mM of sulfhydryl group(s) from one or more sulfhydryl compound(s) and a concentration of at least more than 3.0 g/L glucose.
Preferably, the cell culture medium is a chemically defined medium, preferably a serum-free, protein-free and/or oligopeptide-free cell culture medium, more preferably a chemically defined medium, more preferably a serum-free, protein-free and oligopeptide-free cell culture medium.

Equally, the present invention relates to a mammalian cell producing the anti-CD20/anti-CD3 bispecific antibody as disclosed in the context of the invention having monogalactosylated (G1) and digalactosylated (G2) glycans comprising a polynucleotide comprising a sequence having 80% identity to a polynucleotide encoding a first antigen binding domain comprising a first and a second heavy chain variable domain (VH) as disclosed in the context of the invention, or comprising a sequence having 80% identity to a polynucleotide comprising a sequence encoding a second antigen binding domain comprising a first and a second light chain variable domain (VL) as disclosed in context of the invention, or one or more vectors comprising such polynucleotides,
wherein said cell is cultivated in a cell culture medium as disclosed in the context of the invention.

Preferably, the mammalian cell further comprises a sequence having 80% identity to a polynucleotide encoding a first and a second heavy chain as disclosed in the context of the invention, or comprising a sequence having 80% identity to a polynucleotide comprising a sequence encoding a first and a second light chain as disclosed in context of the invention, or one or more vectors comprising such polynucleotides, wherein said cell is cultivated in a cell culture medium as disclosed in the context of the invention.

Equally, the present invention relates to an anti α-synuclein antibody having monogalactosylated (G1) and digalactosylated (G2) glycans comprising a polynucleotide comprising a sequence having 80% identity to a polynucleotide encoding a heavy chain variable domain (VH) as disclosed in the context of the invention, or a polynucleotide comprising a sequence having 80% identity to a polynucleotide encoding a light chain variable domain (VL) as disclosed in the context of the invention, or one or more vectors comprising such polynucleotides,
wherein said cell is cultivated in a cell culture medium as disclosed in the context of the invention.

Equally, the present invention relates to a method of producing an anti-CD20/anti-CD3 bispecific antibody as disclosed in the context of the invention having monogalactosylated (G1) and digalactosylated (G2) glycans, said method comprising:

(a) cultivating a mammalian cell as disclosed in the context of the invention in a cell culture medium as disclosed in the context of the invention, wherein a concentration of at least more than 4.0 and less than 10.0 mM of the sulfhydryl group(s) from one or more sulfhydryl compound(s) and at least more than 3.0 g/L glucose in the cell culture medium is maintained for at least 3, more preferably for at least 4 and even more preferably for at least 5 days, (b) isolating said antibody.

Preferably, maintaining the concentration is effective for the production of an anti-CD20/anti-CD3 bispecific antibody having 19.0-29.0% (w/w) of G1 and 1.3-2.8% (w/w) of G2 per total glycan; preferably 20.0-28.0% (w/w) of G1 and 1.4-2.7% (w/w) of G2 per total glycan; more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan.

Preferably, the cultivation of the mammalian cell results in an increased titer of said antibody by at least 20%, preferably at least 30%, more preferably at least 40%, more preferably at least 50%, even more preferably at least 60%, and most preferably at least 80% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium. As another example, the cultivation of the mammalian cell results in an increased titer of said antibody between 30 and 75% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium.

Equally, the present invention relates to a method of producing an anti α-synuclein antibody as disclosed in the context of the invention having monogalactosylated (G1) and digalactosylated (G2) glycans, said method comprising:

(a) cultivating a mammalian cell as disclosed in the context of the invention in a cell culture medium as disclosed in the context of the invention, wherein a concentration of at least more than 4.0 and less than 10.0 mM of the sulfhydryl group(s) from one or more sulfhydryl compound(s) and at least more than 3.0 g/L glucose in the cell culture medium is maintained for at least 3, more preferably for at least 4 and even more preferably for at least 5 days, (b) isolating said antibody.

Preferably, the concentration is effective for the production of an anti α-synuclein antibody having 17.2-48.0% (w/w) of G1 and 3.1-15.0% (w/w) of G2 per total glycan 25.4-48.0% (w/w) of G1 and 3.5-15.0% (w/w) of G2 per total glycan; preferably 27.2-47.0% of G1 and 4.4 to 15.0% of G2 per total glycan; preferably 40.0-46.0% (w/w) of G1 and 8.4-15.0% (w/w) of G2 per total glycan; more preferably 41.0-45.0% (w/w) of G1 and 9.5-14.0% (w/w) of G2 per total glycan and most preferably 42.1-43.9% (w/w) of G1 and 10.6-13.3% (w/w) of G2 per total glycan.

Preferably, the cultivation of the mammalian cell results in an increased titer of said antibody by at least 10%, preferably at least 20%, more preferably at least 30%, more preferably at least 40%, more preferably at least 50%, more preferably at least 60%, more preferably at least 70%, even more preferably at least 80% and most preferably at least 100% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium.

Preferably, the cultivation of the mammalian cell results in the anti α-synuclein antibody having monogalactosylated (G1) and digalactosylated (G2) glycans characterized by (i) increased protein target binding by at least 10%, preferably at least 20%, more preferably at least 35%, even more preferably at least 45% and most preferably at least 50%;

(ii) increased neonatal Fc receptor (FcRn) binding by at least 10%, preferably at least 20%, more preferably at least 33%, more preferably at least 40% and most preferably at least 45%; and/or;

(iii) increased FcγRIIa binding by at least 10%, preferably at least 20%, more preferably at least 36%, even more preferably 45% and most preferably 50%, relative to the non-monogalactosylated (G1) and non-digalactosylated (G2) forms of the anti α-synuclein antibody in a corresponding cultivation of the mammalian cell without maintaining the concentration of the at least more than 4.0 and less than 10.0 mM of sulfhydryl group(s) from the one or more sulfhydryl compound(s) in the cell culture medium.

The methods as disclosed in the context of the invention preferably comprise cultivation of the mammalian cell in a starting concentration of at least more than 3.0 and less than 10.0 mM of the sulfhydryl group(s) from the one or more sulfhydryl compound(s). Preferably, the methods further comprise the step of pre-cultivating of the mammalian cell in a cell culture medium prior to said cultivating. Preferably, the concentration is maintained for at least 5 days, preferably for at least 7 days, more preferably for at least 10 days, even more preferably for at least 12 days and most preferably for at least 14 days.

Preferably, the sulfhydryl group(s) from the one or more sulfhydryl compound(s) in the cell culture medium as disclosed in the context of the invention are contained in the reduced and/or oxidized form, more preferably the concentration of the reduced form of said sulfhydryl ranges between more than 4.0 mM and less than 10.0 mM and/or the concentration of the oxidized form of said sulfhydryl ranges between more than 2.0 mM and less than 5.0 mM.

Preferably, the methods as disclosed in the context of the invention further comprise harvesting the anti-CD20/anti-CD3 bispecific antibody or the anti α-synuclein antibody.

Preferably, the methods as disclosed in the context of the invention further comprise measuring a level of the mono-galactosylated (G1) and digalactosylated (G2) glycans of the anti-CD20/anti-CD3 bispecific antibody or the anti α-synuclein antibody. Preferably, the methods further comprise formulating the anti-CD20/anti-CD3 bispecific antibody or the anti α-synuclein antibody into a drug product.

Preferably, the cell culture medium as disclosed in the context of the invention comprises at least more than 4.0 mM and equal or less than 9.0 mM, preferably at least more than 4.0 mM and equal or less than 8.0 mM, more preferably at least more than 4.0 mM and equal or less than 7.0 mM and even more preferably at least more than 4.0 mM and equal or less than 6.0 mM of the sulfhydryl group(s) from the one or more sulfhydryl compound(s).

Preferably, the cell culture medium as disclosed in the context of the invention comprises a concentration of at least 5.0 mM and less than 10.0 mM, preferably at least 5.0 mM and equal or less than 9.0 mM, more preferably at least 5.0 mM and equal or less than 8.0 mM, even more preferably at least 5.0 mM and equal or less than 7.0 mM and most preferably at least 5.0 mM and equal or less than 6.0 mM of the sulfhydryl group(s) from the one or more sulfhydryl compound(s).

Preferably, the cell culture medium as disclosed in the context of the invention comprises at least more than 2.0 g/L glucose, preferably at least more than 3.0 g/L glucose and more preferably at least more than 4.0 g/L glucose.

Preferably, the cell culture medium comprises at most 13.0 g/L glucose, preferably at most 8.0 g/L, more preferably at most 7.0 g/L, even more preferably at most 6.0 g/L and most preferably at most 5.0 g/L glucose.

Preferably, the cell culture medium comprises between more than 2.0 g/L and at most 13.0 g/L glucose, preferably between more than 2.0 g/L and at most 8.0 g/L glucose, more preferably between more than 2.0 g/L and at most 7.0 g/L glucose, even more preferably between more than 2.0 g/L and at most 6.0 g/L glucose and most preferably between more than 2.0 g/L and at most 5.0 g/L glucose.

Preferably, the one or more sulfhydryl compound(s) of the cell culture medium as disclosed in the context of the invention are selected from the group consisting of cysteine, cystine, succimer, methimazole, cysteamine, azathioprine, mercaptopurine, S-methylcysteine, selenocysteine, S-phosphocysteine, 4'-phosphopantetheine, butyrylthiocholine, carbocisteine. N-sulphocysteine, alethine, acetylcysteine, dimercaprol, coenzyme M, sodium aurothiomalate, pantethine, bucillamine, methylselenocysteine, dimercaptosuccinic acid, acetylcysteine amide, thioglycolic acid, 2,3-dimercaptopropanol, O-methylmercaptoethanol, mercaptoacetic acid, fl-mercaptopropionic acid, methylmercaptan, S-methylmercaptoethanol, glutathione, glutathione derivatives, and a combination thereof. More preferably, the one or more sulfhydryl compound(s) are selected from the group consisting of cysteine, cystine, and a combination thereof. Even more preferably, the one or more sulfhydryl compound(s) is cysteine, and wherein the cysteine concentration in the cell culture medium is more than 4.0 mM and less than 10.0 mM, preferably the cysteine concentration is at least 5.0 mM and equal or less than 6.0 mM. Equally preferably, the one or more sulfhydryl compound(s) is cystine, and wherein the cystine concentration in the cell culture medium is more than 2.0 mM and less than 5.0 mM, preferably the cystine concentration is at least 3.0 mM and equal or less than 4.0 mM.

Preferably, cultivation of the mammalian cell of the method as disclosed in the context of the invention is in a large-scale format bioreactor, preferably in a 10,000 L bioreactor.

Equally, the present invention relates to an anti-CD20/anti-CD3 bispecific antibody as disclosed in the context of the invention having monogalactosylated (G1) and digalactosylated (G2) glycans obtainable by the method or the mammalian cell as disclosed in the context of the invention.

Equally, the present invention relates to an anti α-synuclein antibody as disclosed in the context of the invention having monogalactosylated (G1) and digalactosylated (G2) glycans obtainable by the method or the mammalian cell as disclosed in the context of the invention.

Preferably, the invention relates to an anti-CD20/anti-CD3 bispecific antibody as disclosed in the context of the invention having monogalactosylated (G1) and digalactosylated (G2) glycans for use as a medicament. More preferably, the anti-CD20/anti-CD3 bispecific antibody as disclosed in the context of the invention is for use in the treatment of patients with B-cell associated cancers, preferably for use in the treatment of patients with chronic leukemia and lymphoma.

Equally preferably, the invention relates to an anti α-synuclein antibody having monogalactosylated (G1) and digalactosylated (G2) glycans for use as a medicament. More preferably, the anti α-synuclein antibody as disclosed in the context of the invention is for use in the treatment of patients with Parkinson's disease.

BRIEF DESCRIPTION OF THE DRAWINGS

FIGS. 1-12 depict embodiments as described herein.

FIG. 1: Glucose conversion pathway in the formation of UDP-glucose and UDP-galactose in CHO K1M. EC 2.7.7.9: UTP: α-D-glucose-1-phosphate uridylyltransferase. UDP-Glc-E: Uridine-diphosphate glucose epimerase.

FIG. 2: Combined interconversion pathways for UDP-glucose and UDP-galactose in CHO K1M. EC 2.7.7.9: UTP: α-D-glucose-1-phosphate uridylyltransferase. UDP-Glc-E: Uridine-diphosphate glucose epimerase. UDP-Gal-T: UDP-α-D-glucose: α-D-galactose-1-phosphate uridylyltransferase.

FIG. 3: Modulating interconversion pathways for UDP-glucose and UDP-galactose in CHO K1M with sulfhydryl compounds. UDP-Glc-E: Uridine-diphosphate glucose epimerase. UDP-Gal-T: UDP-α-D-glucose: α-D-galactose-1-phosphate uridylyltransferase.

FIG. 4: Modulating interconversion pathways for UDP-glucose and UDP-galactose in CHO K1M with L-cystine in cell culture medium. UDP-Glc-E: Uridine-diphosphate glucose epimerase. UDP-Gal-T: UDP-α-D-glucose: α-D-galactose-1-phosphate uridylyltransferase.

FIG. 5: UDP-galactose is generated from UDP-glucose and used in the Golgi for the protein galactosylation. UDP-Glc-E: Uridine-diphosphate glucose epimerase. UDP-Gal-T: UDP-α-D-glucose: α-D-galactose-1-phosphate uridylyl-transferase. EC2.4.1.38: ß-N-acetyl-glucosaminylglycopeptide beta-1,4-galactosyltransferase.

FIG. 6A: Effect of different L-cysteine concentrations on G0 form of anti-α-synuclein antibody in a CHO L965 cell culture with 6 mM L-cysteine or 10 mM L-cysteine in production medium. Percentage of G0 form of anti-α-synuclein antibody is shown at the end of a 14-day production process.

FIG. 6B: Effect of different L-cysteine concentrations on G1 form of anti-α-synuclein antibody in a CHO L965 cell culture with 6 mM L-cysteine or 10 mM L-cysteine in production medium. Percentage of G1 form of anti-α-synuclein antibody is shown at the end of a 14-day production process.

FIG. 6C: Effect of different L-cysteine concentrations on G2 form of anti-α-synuclein antibody in a CHO L965 cell culture with 6 mM L-cysteine or 10 mM L-cysteine in production medium. Percentage of G2 form of anti-α-synuclein antibody is shown at the end of a 14-day production process FIG. 6D: Effect of different L-cysteine concentrations on product titer of anti-α-synuclein antibody in a CHO L %5 cell culture with 6 mM L-cysteine or 10 mM L-cysteine in production medium. Percentage of product titer of anti-α-synuclein antibody is shown at the end of a 14-day production process.

FIG. 6E: Effect of different L-cysteine concentrations on cell growth (IVCD) of anti-α-synuclein antibody producing CHO L %5 cell culture with 6 mM L-cysteine or 10 mM L-cysteine in production medium. Percentage of cell growth (IVCD) is shown at the end of a 14-day production process.

FIG. 7A: Effect of different L-cysteine concentrations on G0 form of anti CD20/anti CD3 bispecific antibody in a CHO T104 cell culture with 5 mM L-cysteine or 10 mM L-cysteine in production medium. Percentage of G0 form of anti CD20/anti CD3 bispecific antibody is shown at the end of a 14-day production process.

FIG. 7B: Effect of different L-cysteine concentrations on G1 form of anti CD20/anti CD3 bispecific antibody in a CHO T104 cell culture with 5 mM L-cysteine or 10 mM L-cysteine in production medium. Percentage of G1 form of anti CD20/anti CD3 bispecific antibody is shown at the end of a 14-day production process.

FIG. 7C: Effect of different L-cysteine concentrations on product titer of anti CD20/anti CD3 bispecific antibody in a CHO T104 cell culture with 5 mM L-cysteine or 10 mM L-cysteine in production medium. Percentage of product titer of anti CD20/anti CD3 bispecific antibody is shown at the end of a 14-day production process.

FIG. 7D: Effect of different L-cysteine concentrations on cell growth (IVCD) of anti-CD20/anti-CD3 bispecific antibody producing CHO T104 cell culture with 5 mM L-cysteine or 10 mM L-cysteine in production medium. Percentage of cell growth (IVCD) is shown at the end of a 14-day production process.

FIG. 8A: Effect of different L-cysteine concentrations on G0 form of anti-CD20/anti-CD3 bispecific antibody in a CHO T104 cell culture with 5 mM L-cysteine or 10 mM L-cysteine in production medium. Percentage of G0 form of anti-CD20/anti-CD3 bispecific antibody is shown at the end of a 14-day production process.

FIG. 8B: Effect of different L-cysteine concentrations on G1 form of anti-CD20/anti-CD3 bispecific antibody in a CHO T104 cell culture with 5 mM L-cysteine or 10 mM L-cysteine in production medium. Percentage of G1 form of anti-CD20/anti-CD3 bispecific antibody is shown at the end of a 14-day production process.

FIG. 8C: Effect of different L-cysteine concentrations on product titer of anti-CD20/anti-CD3 bispecific antibody in a CHO T104 cell culture with 5 mM L-cysteine or 10 mM L-cysteine in production medium. Percentage of product titer of anti-CD20/anti-CD3 bispecific antibody is shown at the end of a 14-day production process.

FIG. 8D: Effect of different L-cysteine concentrations on cell growth (IVCD) of anti-CD20/anti-CD3 bispecific antibody bsAB producing CHO T104 cell culture with 5 mM L-cysteine or 10 mM L-cysteine in production medium. Percentage of cell growth (IVCD) is shown at the end of a 14-day production process.

FIG. 9A: Effect of different L-cystine concentrations on G0 form of anti-α-synuclein antibody in a CHO L967 cell culture with 2 mM L-cystine or 4 mM L-cystine. Percentage of G0 form of anti-α-synuclein antibody is shown at the end of a 14-day production process.

FIG. 9B: Effect of different L-cystine concentrations on G1 form of anti-α-synuclein antibody in a CHO L967 cell culture with 2 mM L-cystine or 4 mM L-cystine in production medium. Percentage of G1 form of anti-α-synuclein antibody is shown at the end of a 14-day production process.

FIG. 9C: Effect of different L-cystine concentrations on G2 form of anti-α-synuclein antibody in a CHO L967 cell culture with 2 mM L-cystine or 4 mM L-cystine in production medium. Percentage of G2 form of anti-α-synuclein antibody is shown at the end of a 14-day production process.

FIG. 9D: Effect of different L-cystine concentrations on product titer of anti α-synuclein antibody in a CHO L967 cell culture with 2 mM L-cystine or 4 mM L-cystine in production medium. Percentage of product titer of anti-α-synuclein antibody is shown at the end of a 14-day production process.

FIG. 9E: Effect of different L-cystine concentrations on cell growth (IVCD) of anti-α-synuclein antibody producing CHO L967 cell culture with 2 mM L-cystine or 4 mM L-cystine in production medium. Percentage of cell growth (IVCD) is shown at the end of a 14-day production process.

FIG. 10A: Effect of different L-cystine concentrations on G0 form of anti α-synuclein antibody in a CHO L971 cell culture with 2 mM L-cystine or 4 mM L-cystine in production medium. Percentage of G0 form of anti α-synuclein antibody is shown at the end of a 14-day production process.

FIG. 10B: Effect of different L-cystine concentrations on G1 form of anti-α-synuclein antibody in a CHO L971 cell culture with 2 mM L-cystine or 4 mM L-cystine in production medium. Percentage of G1 form of anti-α-synuclein antibody is shown at the end of a 14-day production process.

FIG. 10C: Effect of different L-cystine concentrations on G2 form of anti α-synuclein antibody in a CHO L971 cell culture with 2 mM L-cystine or 4 mM L-cystine in production medium. Percentage of G2 form of anti α-synuclein antibody is shown at the end of a 14-day production process.

FIG. 10D: Effect of different L-cystine concentrations on product titer of anti α-synuclein antibody in a CHO L971 cell culture with 2 mM L-cystine or 4 mM L-cystine in production medium. Percentage of product titer of anti α-synuclein antibody is shown at the end of a 14-day production process.

FIG. 10E: Effect of different L-cystine concentrations on cell growth (IVCD) of anti α-synuclein antibody producing CHO L971 cell culture with 2 mM L-cystine or 4 mM L-cystine in production medium. Percentage of cell growth (IVCD) is shown at the end of a 14-day production process.

FIG. 11A: Effect of different L-cystine/L-cysteine concentration on G1 form of anti-α-synuclein antibody in a CHO L971 cell culture with 6 mM L-cysteine or 3 mM L-cystine in production medium. Percentage of G1 form of anti α-synuclein antibody is shown at the end of a 14-day production process.

FIG. 11B: Effect of different L-cystine/L-cysteine concentration on G2 form of anti α-synuclein antibody in a CHO L971 cell culture with 6 mM L-cysteine or 3 mM L-cystine in production medium. Percentage of G2 form of anti-α-synuclein antibody is shown at the end of a 14-day production process.

FIG. 11C: Effect of different L-cystine/L-cysteine concentration on FcRn relative binding level of anti α-synuclein antibody in a CHO L971 cell culture with 6 mM L-cysteine or 3 mM L-cystine in production medium. Percentage of FcRn relative binding level of anti α-synuclein antibody is shown at the end of a 14-day production process.

FIG. 11D: Effect of different L-cystine/L-cysteine concentration on Fcγ-RIIa (H131) relative binding level of anti α-synuclein antibody in a CHO L971 cell culture with 6 mM L-cysteine or 3 mM L-cystine in production medium. Percentage of Fcγ-RIIa (H131) relative binding level of anti α-synuclein antibody is shown at the end of a 14-day production process.

FIG. 11E: Effect of different L-cystine/L-cysteine concentration on relative target binding of anti α-synuclein antibody in a CHO L971 cell culture with 6 mM L-cysteine or 3 mM L-cystine in production medium. Percentage of relative target binding is shown at the end of a 14-day production process.

FIG. 12: Schematic representation of glycosylation sites in the Fc region (#1 Fc-Glycosylation), FcγIIa and FcRn effector binding sites (#2 FcγIIa Binding and FcRn Binding) antigen binding site in the Fab region (#4 Fab-Binding) and C-terminal modifications (#5 C-terminal Change) of an antibody.

DETAILED DESCRIPTION OF A PREFERRED EMBODIMENT

Recombinant proteins having different glycosylation patterns, specifically galactosylation patterns, are typically produced by a fermentative production process using mammalian expression systems. Post-translational glycosylation, in particular galactosylation, of proteins is essential to fulfill important physiochemical properties and functions, such as protein solubility, stability, clearance, immunogenicity and immune effector functions. In this regard, differences in glycosylation patterns, specifically galactosylation patterns, of recombinantly produced proteins have recently been the topic of much attention in the scientific community as recombinant proteins produced as probable prophylactics and therapeutics approach the clinic. The oligosaccharide side chains of the glycoproteins can affect the protein's function (Wittwer and Howard, Biochem. 29 (1990) 41754180) and the intramolecular interaction between portions of the glycoprotein resulting in the conformation and presented three-dimensional surface of the protein (Hart, Curr. Op. Cell Biol., 4 (1992) 1017-1023: Goochee, et al., Bio/Technology 9 (1991) 1347-1355; Parekh, Curr, Op. Struct, Biol. 1 (1991) 750-754). For example, the galactosylation status of a recombinant protein is regulated by different enzymes and differences in the function of one or more of these enzymes can have significant effects on the galactosylation status of the recombinant protein. In this context, multiple effects of enzymatic UDP-sugar pathway modulation on recombinant mammalian cells, e.g. CHO cells, have been demonstrated and include but are not limited to an effect on cell growth, on recombinant protein productivity and/or protein quality, in particular in galactosylation level. Further effects on biological functions of recombinant mAb have been demonstrated. It is therefore important to maintain the galactosylation pattern of recombinant proteins, particularly of those proteins intended for use as therapeutics.

The quality of recombinant proteins, in particular therapeutic proteins such as antibodies, has been known to depend on various parameters, such as the concentration of various nutrients that are present in the media because such nutrients, e.g. sugar molecules, act as precursors to the sugar-nucleotide pool inside cells required for glycosylation. Varying sugar nucleotide concentration levels in the cells can have significant implications on antibody heterogeneity, particularly important in batch or fed-batch processes where consistent quality of the product is necessary for achieving pre-determined clinical outcome.

Therefore, one major object of this invention is the use sulfhydryl compounds, such as cysteine or cystine, to in vivo regulate intracellular UDP-glucose and UDP-galactose concentration in mammalian cells, such as CHO K1 and its derivative cell lines, thereby improving the final product quality for pre-defined clinical applications.

In this context, the present invention relates to a glycoprotein, particularly a recombinant glycoprotein, having monogalactosylated (G1) and digalactosylated (G2) glycans as well as means and methods for producing said glycoprotein. Thereby, the glycoprotein as described herein and in the context of the invention may be, for example, a therapeutic glycoprotein, such as a recombinant glycoprotein. Thus, as disclosed herein and used in context of the invention, the glycoprotein, such as a recombinant protein, is a protein which can be associated with one or more glycans. As disclosed herein and illustrated in the appended Examples, a protein associated with one or more glycans refers to a protein having monogalactosylated (G1) or digalactosylated (G2) glycans. The protein having one or more glycans may possess several sites at which a glycan can be associated. The person skilled in the art is aware of potential sites where a glycan can be associated with the protein as disclosed herein and in context of the invention. For example, the protein may comprise at least one, more preferably at least two galactosylated glycans, and wherein the galactosylated glycans may be associated with N-acetylglucosamine. Such glycans may either be monogalactosylated (G1) or digalactosylated (G2). As described herein, the level of monogalactosylated (G1) or digalactosylated (G2) protein may be measured by means and methods known to the person skilled in the art and as illustrated in the appended examples.

As disclosed herein and in context of the invention, the recombinant protein may be a therapeutic protein. Such a therapeutic protein may be, for example, an antibody but is not limited thereto. Thus, said glycoprotein, e.g., an antibody, may be used as a medicament. Therapeutic proteins may include but are not limited to therapeutic proteins for use in the treatment of B-cell proliferative disorders such as non-Hodgkin's lymphoma and chronic lymphocytic leukemia, Parkinson's disease and related disorders. In one particular embodiment, the recombinant protein may be an antibody. For example, the antibody to be produced by the mammalian cell is an antibody to be used in therapy or an antibody used as a drug candidate to develop a drug for use in therapy. In one embodiment, the recombinant protein may be anti α-synuclein antibody or anti-CD20/anti-CD3 bispecific antibody.

Said glycoprotein, e.g., an antibody, may be produced by a mammalian cell which comprises a polynucleotide encoding said glycoprotein. For example, the mammalian cells as described herein and in context of the invention may be cultivated in a large-scale format bioreactor, such as in a 10,000 L bioreactor. Chinese Hamster Ovary (CHO) cells are the most frequently used eukaryotic host for recombinant therapeutic protein production.

As described herein and in the context of the invention, the glycoprotein may be an antibody such as a bispecific antibody, e.g., anti-CD20/anti-CD3 antibody. Said antibody may be expressed on a vector comprising one or more polynucleotides encoding said antibody. As another example, the antibody may be anti α-synuclein antibody and said antibody may be cloned into a suitable vector such as but not limited to either a LoxP.SV40.Puro.CMVi.FseI nbe or a Loxfas.puro.CMV.2L.v1 expression vector. CHO-K1M TI host cells were transfected with this polycistronic plasmid for generating stable eukaryotic cell lines. As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors. For example, the one or more vector as described herein may be a polycistronic vector. As used herein, the term "polycistronic" refers to an mRNA encoding more than one polypeptide chain. As one particular example, more than one vector may be used, wherein a first vector may express a first light chain and a second heavy chain and a second vector may express a second light chain and a first heavy chain. The person skilled in the art knows how to construct vectors suitable for expressing an antibody as described herein and in the context of the invention. Further, for the generation of recombinant cell lines, a host cell can be co-transfected with one or more vectors, wherein said vectors may comprise a selection marker such as dihydrofolate reductase (DHFR) gene. For example, expression of the murine DHFR gene is driven by the Simian Virus 40 (SV40) early promoter and terminated by the SV40 polyadenylation signal (SV40 poly A).

Further, a cell culture medium as described herein and in the context of the invention may be used for producing said glycoprotein, such as an antibody, wherein the cell culture medium comprises a concentration of more than 4.0 mM and less than 10.0 mM of sulfhydryl group(s) from one or more sulfhydryl compound(s) and a concentration of at least more than 3.0 g/L glucose. The cell culture medium may be a chemically defined medium, preferably a serum-free, protein-free and/or oligopeptide-free cell culture medium. For example, typical chemically defined cell culture media may contain up to 100 components which can be grouped into energy source, amino acids, vitamins, trace elements and inorganic salts, nucleic acid derivatives, fatty acids and lipids, and some others.

As described herein, the mammalian cell producing the glycoprotein as described herein and illustrated by the appended Examples may be cultured by a method comprising (a) cultivating the mammalian cell in the cell culture medium as described herein, wherein a concentration of the at least more than 4.0 and less than 10.0 mM of the sulfhydryl group(s) from the one or more sulfhydryl compound(s) and at least more than 3.0 g/L glucose in the cell culture medium is maintained for at least 3, more preferably for at least 4 and even more preferably for at least 5 days, (b) isolating said glycoprotein.

Said cultivation of the mammalian cell may result an increased titer of said glycoprotein relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium. Said cultivation may additionally result in a glycoprotein having monogalactosylated (G1) and digalactosylated (G2) glycans as described herein and characterized by increased protein target binding, increased neonatal Fc receptor (FcRn) binding, and/or increased FcγRIIa binding relative to the non-monogalactosylated (G1) and non-digalactosylated (G2) forms of the glycoprotein in a corresponding cultivation of the mammalian cell without maintaining the concentration of the at least more than 4.0 and less than 10.0 mM of sulfhydryl group(s) from the one or more sulfhydryl compound(s) in the cell culture medium. Particularly, the cultivation of the mammalian cell may comprise cultivation in a starting concentration of at least more than 3.0 and less than 10.0 mM of the sulfhydryl group(s) from the one or more sulfhydryl compound(s). The method may further comprise the step of pre-cultivating of the mammalian cell in a cell culture medium prior to said cultivating.

The cell culture process as disclosed herein and in context of the invention refers to a cell culture process starting from inoculating the cells in the cell culture medium and may end with harvesting the cells from the cell culture medium. Said inoculation refers to day 1 of the cell culture process and harvesting the cells from the cell culture medium may be, for example but not limited to, on day 12, 13 or 14 of the cell culture. Thereby, the person skilled in the art knows how to choose a suitable duration of a cell culture process by common general knowledge. This is also illustrated by the appended Examples. The entire cell culture process as disclosed herein and used in context of the invention may comprise a growth phase and a production phase. As described herein and used in context of the invention, the concentration of the sulfhydryl group(s) from the one or more sulfhydryl compound(s) is maintained for at least 5 days, preferably for at least 7 days, more preferably for at least 10 days, even more preferably for at least 12 days and most preferably for at least 14 days of the cell culture process.

The method as disclosed herein and in context of the invention may further comprise the step of precultivating of the mammalian cells in a cell culture medium. Said precultivation step may comprise culturing the cell in a cell culture medium comprising 4.0 mM to 10.0 mM of the sulfhydryl group(s) from the one or more sulfhydryl compound(s) as disclosed herein and in context of the invention or may not comprise said concentration of the sulfhydryl group(s) from the one or more sulfhydryl compound(s) in the cell culture medium. Particularly, the cell culture medium of the precultivation step may either comprise the medium used for inoculating of a bioreactor with a mammalian cell, or may comprise a medium that does not comprise the medium used for inoculating of a bioreactor with a mammalian cell as disclosed herein and in context of the invention.

The sulfhydryl group(s) from the one or more sulfhydryl compound(s) in the cell culture medium may be contained in oxidized form and/or a reduced form. Said oxidized form means that the sulfhydryl group(s) from the one or more sulfhydryl compound(s) are contained in the cell culture medium in the "bound form", while the reduced form means that the sulfhydryl group(s) from the one or more sulfhydryl compound(s) are contained in the "free form", which means that the sulfhydryl group(s) comprises a free —SH group. The cell culture medium as disclosed herein and used in context of the invention may comprise 4 mM to 10 mM of the sulfhydryl group(s) from one or more sulfhydryl compound(s) in its oxidized and/or reduced form. For example, the one or more sulfhydryl compound(s) may be cysteine, cystine, succimer, methimazole, cysteamine, azathioprine, mercaptopurine. S-methylcysteine, selenocysteine, S-phosphocysteine, 4'-phosphopantetheine, butyrylthiocholine, carbocisteine, N-sulphocysteine, alethine, acetylcysteine, dimercaprol, coenzyme M, sodium aurothiomalate, pantethine, bucillamine, methylselenocysteine, dimercaptosuccinic acid, acetylcysteine amide, thioglycolic acid, 2,3-dimercaptopropanol, O-methylmercaptoethanol, mercaptoacetic acid, fl-mercaptopropionic acid, methylmercaptan. S-methylmercaptoethanol, glutathione, glutathione derivatives. For example, the sulfhydryl group from one or more sulfhydryl compounds in the cell culture medium as disclosed herein and used in context of the invention may be cysteine. As another example, the one or more sulfhydryl compound(s) in the cell culture medium as disclosed herein and used in context of the invention may be cystine. As still another example, the one or more sulfhydryl compound(s) in the cell culture medium as disclosed herein and used in context of the invention may be cystine and cysteine.

The method may further comprise measuring a level of the monogalactosylated (G1) and digalactosylated (G2) glycans of the glycoprotein, such as an antibody, as described herein.

The person skilled in the art is aware of means and methods how to measure and determine said concentration of the sulfhydryl group(s) from one or more sulfhydryl compound(s) in the cell culture medium. Such concentration may be obtained by determining the amount of the sulfhydryl compound(s) by mass spectrometry and calculating the amount of the sulfhydryl group(s) present in said sulfhydryl compound(s). Further means and methods of how to measure and determine the concentration of the sulfhydryl group(s) from the one or more sulfhydryl compound(s) are within skilled person's general knowledge.

The method or the cell culture medium as described herein may comprise, for example, at least more than 4.0 mM and equal or less than 9.0 mM, preferably at least more than 4.0 mM and equal or less than 8.0 mM, more preferably at least more than 4.0 mM and equal or less than 7.0 mM and even more preferably at least more than 4.0 mM and equal or less than 6.0 mM of the sulfhydryl group(s) from the one or more sulfhydryl compound(s). As another example, the cell culture medium comprises a concentration of at least 5.0 mM and less than 10.0 mM, preferably at least 5.0 mM and equal or less than 9.0 mM, more preferably at least 5.0 mM and equal or less than 8.0 mM, even more preferably at least 5.0 mM and equal or less than 7.0 mM and most preferably at least 5.0 mM and equal or less than 6.0 mM of the sulfhydryl group(s) from the one or more sulfhydryl compound(s).

As a particular example, the one or more sulfhydryl compound(s) is cysteine, and the cysteine concentration in the cell culture medium is more than 4.0 mM and less than 10.0 mM, preferably the cysteine concentration is at least 5.0 mM and equal or less than 6.0 mM. As another particular example, the one or more sulfhydryl compound(s) is cystine, and the cystine concentration in the cell culture medium is more than 2.0 mM and less than 5.0 mM, preferably the cystine concentration is at least 3.0 mM and equal or less than 4.0 mM.

In most chemically-defined cell culture media for the cultivation of mammalian cells, glucose is the single most commonly used carbohydrate, because it can be efficiently transported into the cells (Wright et al., J Exp Biol 196 (1994) 197-212). Glucose is a simple monosaccharide.

Besides being used as an energy source, glucose can also be used as building blocks for many other molecules and structures. In order to serve these purposes, a given monosaccharide has to be "activated" first. This activation involves the addition of a nucleoside-diphosphate group to a sugar, resulting in the formation of a nucleotide sugar. For example, in CHO cells, the vast majority of nucleotide-sugars are synthesized in well-characterized reactions from glucose. As shown in FIG. 1, D-glucose is converted to D-glucose-1-phosphate. The activation of D-glucose-1-phosphate via UTP-glucose-1-phosphate uridylyltransferase (EC 2.7.7.9) yields a cytoplasmic pool of UDP-glucose (Turnquist and Hansen, The Enzymes, 3rd. Ed. (Boyer, P. D., ed.) 8 (1973) 51-71; Chang et al., Eur. J. Biochem. 236 (1996) 723-728).

Thus, the cell culture medium as described herein and used in the context of the invention may, for example, comprise at least more than 3.0 g/L glucose and more preferably at least more than 4.0 g/L glucose. In addition, or alternatively, the cell culture medium comprises, for example, at most 13.0 g/L glucose, preferably at most 8.0 g/L, more preferably at most 7.0 g/L, even more preferably at most 6.0 g/L and most preferably at most 5.0 g/L glucose. As a particular example, the cell culture medium comprises between more than 3.0 g/L and at most 13 g/L glucose, preferably between more than 3.0 g/L and at most 8.0 g/L glucose, more preferably between more than 3.0 g/L and at most 7.0 g/L glucose, even more preferably between more than 3.0 g/L and at most 6.0 g/L glucose and most preferably between more than 3.0 g/L and at most 5.0 g/L glucose.

Particularly, the cell culture medium for inoculating and culturing the cells as disclosed herein and in context of the invention may comprise 3.0 mM to 10.0 mM of sulfhydryl group(s) from one or more sulfhydryl compound(s), wherein the sulfhydryl compound(s) may be cysteine and/or cystine. For example, the cells producing a recombinant protein may be CHO cells producing anti α-synuclein antibody or anti-CD20/anti-CD3 bispecific antibody and may be cultured in a cell culture medium comprising 6 mM cysteine. As another example, the cells producing a recombinant protein may be CHO cells producing anti α-synuclein antibody or anti-CD20/anti-CD3 bispecific antibody and may be cultured in a cell culture medium comprising 5 mM cysteine. As yet still another example, the cells producing a recombinant protein may be CHO cells producing anti α-synuclein antibody or anti-CD20/anti-CD3 bispecific antibody and may be cultured in a cell culture medium comprising 4 mM cystine. As yet still another example, the cells producing a recombinant protein may be CHO cells producing anti α-synuclein antibody or anti-CD20/anti-CD3 bispecific antibody and may be cultured in a cell culture medium comprising cystine and cysteine, such as a combined cystine and cysteine concentration between 4.0 mM and 5.0 mM.

As disclosed herein and in context of the invention, the cells may be cultured in a cell culture medium comprising at least more than 3 g/L glucose. Said glucose may be present at the time when inoculating the cell with the cell culture medium as disclosed herein and in context of the invention or may be added during the cell culture process, e.g. between day 4 and 14 of the cell culture process. In one embodiment, glucose may be present during the production phase of the cell culture process.

As illustrated in the appended examples, the cells may be cultured in the presence of 6 mM cysteine and in the presence of at least more than 3 g/L, such as equal or more than 4 g/L glucose. As also illustrated in the appended examples, the cells may be cultured in the presence of 5 mM cysteine and in the presence of at least more than 3 g/L, such as equal or more than 4 g/L glucose.

As illustrated in the Examples, the glucose may be added to the cell culture medium between day 4 to 14 of the cell culture process. In other words, as illustrated in the Examples, the cell culture medium may comprise at least more than 3 g/L glucose from the time when adding glucose to the cell culture medium, such as between day 4 and 14. The glucose may be added to the cell culture medium as disclosed herein and used in context of the invention by a fed-batch process or perfusion but the process by which the glucose is added to said cell culture medium is not limited thereto. It is to be understood that the glucose concentration present in the cell culture medium refers to a concentration which does not impair cell growth and/or production of the recombinant protein by the cell. In other words, a glucose concentration is selected which is suitable for maintaining and/or increasing cell growth and/or production of the recombinant protein by the cell.

As illustrated in the appended Examples, said anti α-synuclein antibody or anti-CD20-CD3 bispecific antibody may be produced in a CHO cell line, such as CHO K1M cell line. It is to be understood that the recombinant protein as disclosed herein and in context of the invention may be produced in any mammalian cell line suitable to produce said recombinant protein. In this context, the person skilled in the art is aware of such suitable mammalian cells and knows how to select such a mammalian cell for producing the recombinant protein as disclosed herein and in context of the invention. Said cells producing a recombinant protein, such as anti α-synuclein antibody or anti-CD20-CD3 bispecific antibody, may include but are not limited to CHO cells, Vero cells, BHK cells, COS cells and HEK293/293T cells. The mammalian cells may be cultured in a chemically defined cell culture medium. Cell culture media to be used in context of the invention are disclosed herein. In this regard, the person skilled in the art is aware of suitable commercially available chemically defined cell culture media, such as but not limited to DMEM, to be used in context of the invention. As illustrated in the appended Examples, a serum-free and chemically-defined medium may be used to culture the mammalian cells. In one embodiment, the cell culture medium is a chemically defined medium, preferably a serum-free, protein-free and/or oligopeptide-free cell culture medium.

As disclosed herein and illustrated by the appended Examples, mammalian cells, such as CHO cells, may be cultured, e.g. up to 14 days, in a culture medium comprising between 4.0 mM to 10 mM of sulfhydryl group(s) from one or more sulfhydryl compound(s), such as cysteine and/or cystine, and at least more than 3 g/L glucose.

The method may further comprise harvesting the glycoprotein, such as an antibody, as described herein. It is to be understood that the cells may be harvested from the cell culture medium during or at the end of the production phase. Thereby, the skilled person is able to choose a suitable time point of harvesting the cells from the cell culture medium as this is also illustrated by the appended Examples. The method may further comprise formulating the glycoprotein, such as an antibody, as described herein into a drug product.

All aspects that are described in the following in the context of the cell culture medium used in the method of the present invention also account for the cell culture medium as used in the context of the present invention. In addition, the present invention provides recombinant proteins having a desired content of galactosylated glycans, wherein the recombinant protein may comprise at least monogalactosylated, more preferably at digalactosylated glycans. Preferably, the galactosylated glycans are associated with N-acetylglucosamine. All aspects that are described in the following in the context of the recombinant protein produced by the method of the present invention also account for the recombinant protein as provided in the context of the present invention. Also provided by the present invention are recombinant proteins obtainable by the method of the present invention and as disclosed in the following.

In this context, the present invention has discovered that sulfhydryl compound(s) and their derivatives, e.g., L-cysteine and/or cystine, may be used to activate UDP-α-D-glucose: α-D-galactose-1-phosphate uridylyltransferase (EC 2.7.7.12). Thereby, the UDP-α-D-glucose: α-D-galactose-1-phosphate uridylyltransferase may be effectively activated. Further, sulfhydryl compound(s) may be used to modulate the UDP-sugar pathway, in particular in vivo. For example, L-cystine, the oxidized dimer form of L-cysteine, may be used to modulate the UDP-sugar pathway, in particular in vivo. Specifically, the UDP-sugar pathway, in particular in vivo, may be modulated by adding sulfhydryl compound(s) and their derivatives, such as cystine and/or cysteine, to increase cell growth, recombinant protein productivity and/or protein quality, in particular increasing galactosylation level of a recombinant protein by mammalian cell culture.

The term "extent of oxidation" refers to the degree to which oxidizable sulfhydryl group(s) from one or more sulfhydryl compound(s) have undergone oxidation in the cell culture medium. For example, if the sulfhydryl compound contains a single sulfhydryl group which is oxidized by forming a disulfide bridge with a sulfhydryl group of another (same or different) sulfhydryl compound, then an increase in mass of said sulfhydryl compound indicates oxidation of the sulfhydryl group. Oxidation status can be measured by metrics known to the arts of protein and peptide chemistry including, without limitation, assay of the number of oxidized residues, mass spectral peak intensity, mass spectral integrated area, and the like. In some embodiments of any of the aspects provided herein, oxidation status is reported as a percentage, wherein 0% refers to no oxidation and 100% refers to complete oxidation of potentially oxidizable sulfhydryl group(s) from the one or more sulfhydryl compound(s) in the medium. The term "potentially oxidizable sulfhydryl group," and the like refers to total amount of sulfhydryl group(s) from one or more sulfhydryl compound(s) in the medium which can undergo oxidation, for example by formation of a disulfide bridge.

The terms "sulfhydryl group which is not oxidized," and the like refers to the amount of sulfhydryl group(s) from one or more sulfhydryl compound(s) in the medium which has not undergone oxidation. The increase in mass of a sulfhydryl compound over the mass of the same sulfhydryl compound which is not oxidized reflects the number of oxidized sulfhydryl group(s) in the sulfhydryl compound. The increase in amount of sulfhydryl compound(s) having oxidized sulfhydryl group(s) over the amount of sulfhydryl compound(s) which have no oxidized sulfhydryl group(s) reflects the extent of oxidation. Then, the oxidation status of the sulfhydryl group(s) from one or more sulfhydryl compound(s) is determined from the total amount of sulfhydryl group(s) from the one or more sulfhydryl compound(s) having one or more oxidized sulfhydryl group(s) and the total amount of sulfhydryl group(s) from one or more sulfhydryl compound(s) in the cell culture medium.

For example, the determination of the oxidation status of sulfhydryl group(s) from one or more sulfhydryl compound(s) in the cell culture medium includes the steps of a) determining the mass and amount of one or more sulfhydryl compound(s) in the cell culture medium; b) comparing the mass determined for the one or more sulfhydryl compound(s) with the mass of one or more sulfhydryl compound(s) which are not oxidized, wherein an increase in mass of one or more sulfhydryl compound(s) over the mass of the one or more sulfhydryl compound(s) which are not oxidized reflects the number of oxidized sulfhydryl group(s) in the one or more sulfhydryl compound(s); and c) determining the oxidation status of one or more sulfhydryl compound(s) from the total amount of one or more sulfhydryl compounds having at least one oxidized sulfhydryl group and thus the total amount of the sulfhydryl group(s) of the one or more sulfhydryl compound(s).

The determination of the mass of target fragments employs mass spectrometry. The terms "mass spectrometry," "MS," and the like refer to methods of filtering, detecting, and measuring ions based on their mass-to-charge (i.e., "m/z") ratio. The terms "mass" and "m/z" are used interchangeably within the context of the results of mass spectrometric analysis, and unless otherwise indicated, all m/z values assume singly ionized species. The terms "main isotope mass" and "main isotope m/z" refer to the mass reported for a molecular ion taking into account the mass of the most abundant (i.e., main) isotope of each element. In general, one or more molecules of interest are ionized, and the ions are subsequently introduced into a mass spectrometer where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 2:264-76 (1999); and Merchant and Weinberger, Electrophoresis 21:1164-67 (2000), each of which is hereby incorporated by reference in its entirety. The terms "integrated intensity," "mass spectral integrated area," "integrated mass spectral intensity," and the like refer to the area under a mass spectrometric curve corresponding to the amount of a molecular ion having a particular main isotope m/z, as is well known in the art.

For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a"mass detector" for the ions injected into the instrument.

Uridine Diphosphate (UDP)-Sugars in Mammalian Cells

Uridine diphosphate (UDP) α-D-glucose epimerase (EC 5.1.3.2) and UDP-α-D-glucose: α-D-galactose-1-phosphate uridylyltransferase (EC 2.7.7.12) are found to play a crucial role within the UDP-glucose and UDP-galactose conversion pathway in mammalian cells, for example in CHO cells.

As used herein, the term "uridine diphosphate (UDP) α-D-glucose epimerase" and "UDP-Glc-E" are used interchangeably and refer to an enzyme which is a homodimeric epimerase found in bacterial, fungal, plant, and mammalian cells, belonging to EC 5.1.3.2 class. As shown in Example 1, the cDNA of UDP-Glc-E in the cell line CHO K1M has been amplified, sequenced and further analyzed.

As used herein, the term "UDP-α-D-glucose: α-D-galactose-1-phosphate uridylyltransferase". "UDP-Gal-T" and "EC 2.7.7.12" are used interchangeably and refer to an enzyme which catalyzes the nucleotide exchange between uridine 5'-diphosphate glucose (UDP-Glucose) and galactose-1-phosphate (Gal-1-P) to produce uridine 5'-diphosphate galactose (UDP-Galactose) and glucose-1-phosphate (Glc-1-P) through reversible mechanism. As shown in Example 2, the cDNA of UDP-Gal-T in the cell line CHO K1M has been amplified, sequenced and further analyzed.

Uridine Diphosphate-Glucose Epimerase

The UDP-glucose and UDP-galactose synthesis pathway is shown in Figure-1. Thereby, UDP-sugar interconversion pathway in the formation of UDP-glucose from α-D-Glucose is shown and the subsequent formation of UDP-galactose from UDP-glucose by UDP-Glucose Epimerase (UDP-Glc-E: Uridine-diphosphate glucose epimerase. EC 5.1.3.2).

UDP-α-D-Glucose: α-D-Galactose-1-Phosphate Uridylyltransferase

The UDP-galactose and UDP-Glucose pathway has been further extended as shown in Figure-2. Thereby, UDP-sugar interconversion pathway in the formation of UDP-galactose from α-D-Glucose is shown and the subsequent conversion of UDP-galactose back to UDP-glucose by UDP-α-D-glucose: α-D-galactose-1-phosphate uridylyltransferase (UDP-Gal-T: UDP-α-D-glucose: α-D-galactose-1-phosphate uridylyltransferase EC 2.7.7.12).

Establishing UDP-Glucose/Galactose Conversion Pathway

As shown in FIG. 2, UDP-Gal-T catalyzes reversible conversion of UDP-glucose and UDP-galactose. However, Wagstaff et al. ((2015) Carbohydrate Research 404: 17-25) have found out that, under certain circumstances (e.g. in the presence of excess glucose-1-P), UDP-Gal-T runs mainly the reverse conversion, tuning most UDP-Galactose into UDP-glucose. This mechanism may lead to an intracellular change in gluco- and galacto-configured UDP-sugar pool, resulting in a decreased intracellular UDP-galactose concentration and an elevated amount of intracellular UDP-glucose. Based on these experimental results, this new UDP-glucose/UDP-galactose pathway can be furthermore precisely described, e.g. as shown in FIG. 2, for a given therapeutic protein production process using a chemically defined medium platform with excess glucose.

A Novel Approach for UDP-Glucose/UDP-Galactose Pathway Regulation in Mammalian Cells with Sulfhydryl Compounds As shown in FIG. 3, sulfhydryl compounds and their derivatives, such as L-cysteine and/or L-cystine, can be added to cell culture medium to further activate UDP-Gal-T and additionally regulate gluco- and galacto-configured UDP-sugars in mammalian cells, such as CHO K1 and its derivative cell lines. Thereby, the present inventors have discovered that by the addition of one or more sulfhydryl compound(s), recombinant proteins having monogalactosylated or digalactosylated glycans can be produced. As used herein, the term "sulfhydryl compound(s)" refers to inorganic or organic compounds that contain sulfur as an integral part of the molecule, preferably compounds containing a —SH radical; and/or compounds initially containing a —SH radical and which are covalently linked together under reducing conditions, thereby forming a disulfide bridge. The present inventors have discovered that one or more sulfhydryl compound(s) which increase the viable cell density and/or product titer during the production of a recombinant protein produced by mammalian cell culture have a directly correlating effect on the galactose content of the recombinant protein produced. In this context, the present invention provides for processes for controlling the extent of galactosylation of a recombinant protein produced by mammalian cell culture. Following the methods as provided herein, the person skilled in the art is able to determine the precise process parameters that provide for controlling the galactose content of a recombinant protein produced by mammalian cell culture. In one aspect in the context of the present invention, during the production of a recombinant protein produced by mammalian cell culture, the galactose content of the recombinant protein can be increased. In one further aspect of the present invention, the recombinant protein having monogalactosylated (G1) or digalactosylated (G2) glycans is an anti-CD20/anti-CD3 bispecific antibody, wherein the anti-CD20/anti-CD3 bispecific antibody has 19.0-29.0% (w/w) of G1 and 1.3-2.8% (w/w) of G2 per total glycan; preferably 20.0-28.0% (w/w) of G1 and 1.4-2.7% (w/w) of G2 per total glycan; more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan.

In particular, the anti-CD20/anti-CD3 bispecific antibody having monogalactosylated (G1) and digalactosylated (G2) glycans comprises a first antigen binding domain that binds to CD3, and a second antigen binding domain that binds to CD20. The anti-CD20/anti-CD3 bispecific antibody may comprise a first antigen binding domain comprising a heavy chain variable region (VH) and a light chain variable region (VL), and a second antigen binding domain comprising a heavy chain variable region (VH) and a light chain variable region (VL).

More particular, the anti-CD20/anti-CD3 bispecific antibody having monogalactosylated (G1) and digalactosylated (G2) glycans comprises a first antigen binding domain, and a second antigen binding domain, wherein the first antigen binding domain comprises a heavy chain variable domain (VH) comprising (a) CDR-H1 comprising the amino acid sequence of SEQ ID NO: 22,
(b) CDR-H2 comprising the amino acid sequence of SEQ ID NO: 23, and
(c) CDR-H3 comprising the amino acid sequence of SEQ ID NO: 24; and a light chain variable domain (VL) comprising (d) CDR-L1 comprising the amino acid sequence of SEQ ID NO: 25,
(e) CDR-L2 comprising the amino acid sequence of SEQ ID NO: 26, and
(f) CDR-L3 comprising the amino acid sequence of SEQ ID NO: 27;

wherein the second antigen binding domain comprises a heavy chain variable domain (VH) comprising (a) CDR-H1 comprising the amino acid sequence of SEQ ID NO: 34,
(b) CDR-H2 comprising the amino acid sequence of SEQ ID NO: 35, and
(c) CDR-H3 comprising the amino acid sequence of SEQ ID NO: 36; and a light chain variable domain (VL) comprising (d) CDR-L1 comprising the amino acid sequence of SEQ ID NO: 37,
(e) CDR-L2 comprising the amino acid sequence of SEQ ID NO: 38, and
(f) CDR-L3 comprising the amino acid sequence of SEQ ID NO: 39; and wherein the anti-CD20/anti-CD3 bispecific antibody has 19.0-29.0% (w/w) of G1 and 1.3-2.8% (w/w) of G2 per total glycan; preferably 20.0-28.0% (w/w) of G1 and 1.4-2.7% (w/w) of G2 per total glycan: more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan.

Preferably, the anti-CD20/anti-CD3 bispecific antibody is an antibody, wherein (a) the first antigen binding domain comprises a VH sequence of SEQ ID NO: 28 and the second antigen binding domain comprises a VH sequence of SEQ ID NO: 40;
(b) the first antigen binding domain comprises a VL sequence of SEQ ID NO: 29 and the second antigen binding domain comprises a VL sequence of SEQ ID NO: 41; or
(c) the first and second antigen binding domain comprises a VH sequence as defined in (a) and a VL sequence as defined in (b).

More preferably, the anti-CD20/anti-CD3 bispecific antibody is an antibody, wherein (a) a VH sequence of the first antigen binding domain has at least 95% sequence identity to the amino acid sequence of SEQ ID NO: 28 and a VH sequence of the second antigen binding domain has at least 95% sequence identity to the amino acid sequence of SEQ ID NO: 40;
(b) a VL sequence of the first antigen binding domain has least 95% sequence identity to the amino acid sequence of SEQ ID NO: 29 and a VL sequence of the second antigen binding domain has at least 95% sequence identity to the amino acid sequence of SEQ ID NO: 41; or
(c) the anti-CD20/anti-CD3 bispecific antibody comprises the VH sequence of the first and second antigen binding domain as defined in (a) and the VL sequence of the first and second antigen binding domain as defined in (b).

As disclosed herein and in the context of the invention, the anti-CD20/anti-CD3 bispecific antibody is an antibody, wherein the anti-CD20/anti-CD3 bispecific antibody may comprise a third antigen binding domain. For example, the anti-CD20/anti-CD3 bispecific antibody is an antibody, wherein the anti-CD20/anti-CD3 bispecific antibody comprises a third antigen binding domain that binds to CD20. Alternatively, the anti-CD20/anti-CD3 bispecific antibody is an antibody, wherein the anti-CD20/anti-CD3 bispecific antibody comprises a third antigen binding domain that binds to CD3. As used herein, the terms "first", "second", "third" etc. with respect to antigen binding domains are used for convenience of distinguishing when there is more than one of each type of domain. Use of these terms is not intended to confer a specific order or orientation unless explicitly so stated.

For example, the anti-CD20/anti-CD3 bispecific antibody may comprise a second antigen binding domain that binds to CD3, a first and a third antigen binding domain that binds to CD20. As a more particular example, the third antigen binding domain may be identical to the first antigen binding domain (i.e. the first and the third antigen binding domains may comprise the same heavy and light chain amino acid sequences). Even more particularly, the first and third Fab molecules comprising the first and third antigen binding domains may be identical and, furthermore, may have the same arrangement of domains (i.e. conventional or crossover).

As another example, the anti-CD20/anti-CD3 bispecific antibody may comprise a first antigen binding domain that binds to CD3, a second and a third antigen binding domain that binds to CD20. As a more particular example, the third antigen binding domain may be identical to the second antigen binding domain (i.e. the second and the third antigen binding domains may comprise the same heavy and light chain amino acid sequences). Even more particularly, the second and third Fab molecules comprising the second and third antigen binding domains may be identical and, furthermore, may have the same arrangement of domains (i.e. conventional or crossover).

As a more particular example described herein, the anti-CD20/anti-CD3 bispecific antibody may comprise a third antigen binding domain, wherein the third antigen binding domain comprises a heavy chain variable domain (VH) comprising
    (a) CDR-H1 comprising the amino acid sequence of SEQ ID NO: 34,
    (b) CDR-H2 comprising the amino acid sequence of SEQ ID NO: 35, and
    (c) CDR-H3 comprising the amino acid sequence of SEQ ID NO: 36; and
    a light chain variable domain (VL) comprising
    (d) CDR-L1 comprising the amino acid sequence of SEQ ID NO: 37,
    (e) CDR-L2 comprising the amino acid sequence of SEQ ID NO: 38, and
    (f) CDR-L3 comprising the amino acid sequence of SEQ ID NO: 39; and
    wherein the anti-CD20/anti-CD3 bispecific antibody has 19.0-29.0% (w/w) of G1 and 1.3-2.8% (w/w) of G2 per total glycan; preferably 20.0-28.0% (w/w) of G1 and 1.4-2.7% (w/w) of G2 per total glycan; more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan.

As an even more particular example, the anti-CD20/anti-CD3 bispecific antibody is an antibody, wherein the third antigen binding domain may comprise a VH sequence of SEQ ID NO: 40 and a VL sequence of SEQ ID NO: 41. Preferably, the anti-CD20/anti-CD3 bispecific antibody is an antibody, wherein the third antigen binding domain may comprise a VH sequence of the third antigen binding domain has at least 95% sequence identity to the amino acid sequence of SEQ ID NO: 40 and a VL sequence of the third antigen binding domain has at least 95% sequence identity to the amino acid sequence of SEQ ID NO: 41.

The first antigen binding domain of the anti-CD20/anti-CD3 bispecific antibody may be a cross-Fab molecule wherein the variable domains or the constant domains of the Fab heavy and light chain are exchanged, and the second and third, if present, antigen binding domain may be a conventional Fab molecule. For example, the antigen binding domain that binds to CD3 is a crossover Fab molecule wherein the variable domains or the constant domains of the Fab heavy and light chain are exchanged (i.e. replaced by each other). As another more particular example, the first antigen binding moiety is a crossover Fab molecule, and the second and the first antigen binding moiety are each a conventional Fab molecule.

A "Fab molecule" refers to a protein consisting of the VH and CH1 domain of the heavy chain (the "Fab heavy chain") and the VL and CL domain of the light chain (the "Fab light chain") of an immunoglobulin. By "fused" is meant that the components (e.g. a Fab molecule and an Fc domain subunit) are linked by peptide bonds, either directly or via one or more peptide linkers.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The third Fab molecule may be fused at the C-terminus of the Fab heavy chain to the N-terminus of the first or second subunit of the Fc domain. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

For example, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. More particularly, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain (see also EP3252078 A1, specifically FIGS. 1B, 1E, 1I and 1M in combination with paragraph [0338] which are incorporated herein by reference).

In other words, the anti-CD20/anti-CD3 bispecific antibody may comprise a third antigen binding domain, wherein the first antigen binding domain of the anti-CD20/anti-CD3 bispecific antibody is fused at the C-terminus of the Fab heavy chain to the N-terminus of the Fab heavy chain of the second antigen binding domain, the second antigen binding domain of the anti-CD20/anti-CD3 bispecific antibody is fused at the C-terminus of the Fab heavy chain to the N-terminus of the first subunit of the Fc domain, and the third antigen binding domain of the anti-CD20/anti-CD3 bispecific antibody is fused at the C terminus of the Fab heavy chain to the N-terminus of the second subunit of the Fc domain.

The second and the third Fab molecule may be fused to the Fc domain directly or through a peptide linker. For example, the second and the third Fab molecule are each fused to the Fc domain through an immunoglobulin hinge region. Particularly, the immunoglobulin hinge region is a human IgG1 hinge region, particularly where the Fc domain is an IgG1 Fc domain. Optionally, the Fab light chain of the first Fab molecule and the Fab light chain of the second Fab molecule may additionally be fused to each other.

Alternatively, the first and the third Fab molecule are each fused at the C-terminus of the Fab heavy chain to the N-terminus of one of the subunits of the Fc domain, and the second Fab molecule is fused at the C-terminus of the Fab heavy chain to the N-terminus of the Fab heavy chain of the first Fab molecule. More particularly, the antibody essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain (see also EP3252078 A1, specifically FIGS. 1C, 1F, 1J and 1N in combination with paragraph 103391 which are incorporated herein by reference).

In other words, the anti-CD20/anti-CD3 bispecific antibody may comprise a third antigen binding domain, wherein the second antigen binding domain of the anti-CD20/anti-CD3 bispecific antibody is fused at the C-terminus of the Fab heavy chain to the N-terminus of the Fab heavy chain of the first antigen binding domain, the first antigen binding domain of the anti-CD20/anti-CD3 bispecific antibody is fused at the C-terminus of the Fab heavy chain to the N-terminus of the first subunit of the Fc domain, and the third antigen binding domain of the anti-CD20/anti-CD3 bispecific antibody is fused at the C terminus of the Fab heavy chain to the N-terminus of the second subunit of the Fc domain.

The first and the third Fab molecule may be fused to the Fc domain directly or through a peptide linker. For example, the first and the third Fab molecule are each fused to the Fc domain through an immunoglobulin hinge region. Particularly, the immunoglobulin hinge region is a human IgG1 hinge region, particularly where the Fc domain is an IgG1 Fc domain. Optionally, the Fab light chain of the first Fab molecule and the Fab light chain of the second Fab molecule may additionally be fused to each other.

As a further alternative, the first and the second Fab molecule are each fused at the C-terminus of the Fab heavy chain to the N-terminus of one of the subunits of the Fc domain, and the third Fab molecule is fused at the C-terminus of the Fab heavy chain to the N-terminus of the Fab heavy chain of the first Fab molecule. More particularly, the antibody essentially consists of the first, the second and the third Fab molecule, the Fc domain composed of a first and a second subunit, and optionally one or more peptide linkers, wherein the third Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the second Fab molecule is fused at the C-terminus of the Fab heavy chain to the N-terminus of the second subunit of the Fc domain. In other words, the anti-CD20/anti-CD3 bispecific antibody may comprise a third antigen binding domain, wherein the third antigen binding domain of the anti-CD20/anti-CD3 bispecific antibody is fused at the C-terminus of the Fab heavy chain to the N-terminus of the Fab heavy chain of the first antigen binding domain, the first antigen binding domain of the anti-CD20/anti-CD3 bispecific antibody is fused at the C-terminus of the Fab heavy chain to the N-terminus of the first subunit of the Fc domain, and the second antigen binding domain of the anti-CD20/anti-CD3 bispecific antibody is fused at the C terminus of the Fab heavy chain to the N-terminus of the second subunit of the Fc domain.

The first and the second Fab molecule may be fused to the Fc domain directly or through a peptide linker. For example, the first and the second Fab molecule are each fused to the Fc domain through an immunoglobulin hinge region. Particularly, the immunoglobulin hinge region is a human IgG1 hinge region, particularly where the Fc domain is an IgG1 Fc domain. Optionally, the Fab light chain of the first Fab molecule and the Fab light chain of the third Fab molecule may additionally be fused to each other.

Further configurations of the anti-CD20/anti-CD3 bispecific antibody as used herein and in context of the invention can be found, e.g., in EP3252078 A1, particularly in FIG. 1 and in paragraphs [0335] to [0367] which are incorporated herein by reference.

Even more particularly, the anti-CD20/anti-CD3 bispecific antibody is an antibody, wherein the anti-CD20/anti-CD3 bispecific antibody may comprise
- (a) a first heavy chain having at least 99% sequence identity to the amino acid sequence of SEQ ID NO: 47 and a second heavy chain having at least 99% sequence identity to the amino acid sequence of SEQ ID NO: 45;
- (b) a first light chain having at least 99% sequence identity to the amino acid sequence of SEQ ID NO: 33, a second and a third light chain having at least 99% sequence identity to the amino acid sequence of SEQ ID NO: 44; or
- (c) the first heavy chain and the second heavy chain as defined in (a) and the first light chain, the second light chain and the third light chain as defined in (b).

Even more particularly, the anti-CD20/anti-CD3 bispecific antibody is an antibody, wherein the anti-CD20/anti-CD3 bispecific antibody comprises
- (a) a first heavy chain of SEQ ID NO: 47 and a second heavy chain of SEQ ID NO: 45;
- (b) a first light chain of SEQ ID NO: 33, a second light chain and a third light chain of SEQ ID NO: 44; or (c) the first heavy chain and the second heavy chain as defined in (a) and the first light chain, the second light chain and the third light chain as defined in (b).

In another aspect of the present invention, the recombinant protein having monogalactosylated (G1) or digalactosylated (G2) glycans is an anti α-synuclein antibody, wherein the anti α-synuclein antibody has 17.2-48.0% (w/w) of G1 and 3.1-15.0% (w/w) of G2 per total glycan; preferably 25.4-48.0% (w/w) of G1 and 3.5-15.0% (w/w) of G2 per total glycan; preferably 27.2-47.0% of G1 and 4.4 to 15.0% of G2 per total glycan; preferably 40.0-46.0% (w/w) of G1 and 8.4-15.0% (w/w) of G2 per total glycan; more preferably 41.0-45.0% (w/w) of G1 and 9.5-14.0% (w/w) of G2 per total glycan and most preferably 42.1-43.9% (w/w) of G1 and 10.6-13.3% (w/w) of G2 per total glycan.

In particular, the anti α-synuclein antibody having monogalactosylated (G1) and digalactosylated (G2) glycans comprises a heavy chain variable domain (VH) comprising (a) CDR-H1 comprising the amino acid sequence of SEQ ID NO: 10, (b) CDR-H2 comprising the amino acid sequence of SEQ ID NO: 11, and (c) CDR-H3 comprising the amino acid sequence of SEQ ID NO: 12; and a light chain variable domain (VL) comprising (d) CDR-L1 comprising the amino acid sequence of SEQ ID NO: 13, (e) CDR-L2 comprising the amino acid sequence of SEQ ID NO: 14, and (f) CDR-L3 comprising the amino acid sequence of SEQ ID NO: 15; and wherein the anti α-synuclein antibody has 17.2-48.0% (w/w) of G1 and 3.1-15.0% (w/w) of G2 per total glycan; preferably 25.4-48.0% (w/w) of G1 and 3.5-15.0% (w/w) of G2 per total glycan: preferably 27.2-47.0% of G1 and 4.4 to 15.0% of G2 per total glycan; preferably 40.0-46.0% (w/w) of G1 and 8.4-15.0% (w/w) of G2 per total glycan; more preferably 41.0-45.0% (w/w) of G1 and 9.5-14.0% (w/w) of G2 per total glycan and most preferably 42.1-43.9% (w/w) of G1 and 10.6-13.3% (w/w) of G2 per total glycan.

More particularly, the anti α-synuclein antibody comprises (a) a VH sequence of SEQ ID NO: 16;

(b) a VL sequence of SEQ ID NO: 17; or (c) the VH sequence as defined in (a) and the VL sequence as defined in (b).

Even more particularly, the anti α-synuclein antibody comprises (a) a VH sequence having at least 95% sequence identity to the amino acid sequence of SEQ ID NO: 16;

(b) a VL sequence having at least 95% sequence identity to the amino acid sequence of SEQ ID NO: 17; or (c) the VH sequence as defined in (a) and the VL sequence as defined in (b).

Even more particularly, the anti α-synuclein antibody comprises a heavy chain having at least 99% sequence identity to the amino acid sequence of SEQ ID NO: 20 and a light chain having at least 99% sequence identity to the amino acid sequence of SEQ ID NO: 21.

Even more particularly, the anti α-synuclein antibody comprises a heavy chain of SEQ ID NO: 20 and a light chain of SEQ ID NO: 21.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point-mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

Preferably, the monogalactosylated (G1) and digalactosylated (G2) glycans of the anti-CD20/anti-CD3 bispecific antibody or the anti α-synuclein antibody as disclosed in the context of the invention are associated with N-acetylglucosamine.

As used herein, the terms "cell culture medium" and "culture medium" are used interchangeably and refer to a nutrient solution used for growing mammalian cells that typically provides at least one component from one or more of the following categories: 1) an energy source, usually in the form of a carbohydrate such as glucose; 2) all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The necessary components, such as growth factors for a particular cell line, are readily determined empirically without undue experimentation, as described for example in Mammalian Cell Culture (Mather, J. P. ed., Plenum Press. N.Y. 119841), and Barnes and Sato. (1980) Cell. 22:649).

As disclosed herein and in the context of the invention, the cell culture medium for producing an antibody having monogalactosylated (G1) and digalactosylated (G2) glycans is a cell culture medium comprising a concentration of more than 4.0 mM and less than 10.0 mM of sulfhydryl group(s) from one or more sulfhydryl compound(s) and a concentration of at least more than 3.0 g/L glucose.

In a preferred aspect of the present invention, the cell culture medium as disclosed in the context of the invention comprises at least more than 4.0 mM and equal or less than 9.0 mM, preferably at least more than 4.0 mM and equal or less than 8.0 mM, more preferably at least more than 4.0 mM and equal or less than 7.0 mM and even more preferably at least more than 4.0 mM and equal or less than 6.0 mM of the sulfhydryl group(s) from the one or more sulfhydryl compound(s).

In another preferred aspect, the cell culture medium as disclosed in the context of the invention comprises a concentration of at least 5.0 mM and less than 10.0 mM, preferably at least 5.0 mM and equal or less than 9.0 mM, more preferably at least 5.0 mM and equal or less than 8.0 mM, even more preferably at least 5.0 mM and equal or less than 7.0 mM and most preferably at least 5.0 mM and equal or less than 6.0 mM of the sulfhydryl group(s) from the one or more sulfhydryl compound(s).

Alternatively (e.g. in the case of cysteine and/or cystine), the cell culture medium comprises between more than 0.7 g/L and equal or less than 1.2 g/L, preferably between more than 0.7 g/L and equal or less than 1.1 g/L, more preferably between more than 0.7 g/L and equal or less than 1.0 g/L, more preferably between more than 0.7 g/L and equal or less than 0.9 g/L, even more preferably between more than 0.7 g/L and 0.8 g/L of one or more sulfhydryl compound(s). The sulfhydryl group(s) from the one or more sulfhydryl compound(s) in the cell culture medium as disclosed in the context of the invention are contained in the reduced and/or oxidized form. For example, the reduced form of said sulfhydryl ranges between more than 4.0 mM and less than 10.0 mM and/or the concentration of the oxidized form of said sulfhydryl ranges between more than 2.0 mM and less than 5.0 mM.

As disclosed herein and in the context of the invention, the one or more sulfhydryl compound(s) may be selected from the group consisting of cysteine, cystine, succimer, methimazole, cysteamine, azathioprine, mercaptopurine, S-methylcysteine, selenocysteine, S-phosphocysteine, 4'-phosphopantetheine, butyrylthiocholine, carbocisteine, N-sulphocysteine, alethine, acetylcysteine, dimercaprol, coenzyme M, sodium aurothiomalate, pantethine, bucillamine, methylselenocysteine, dimercaptosuccinic acid, acetylcysteine amide, thioglycolic acid, 2,3-dimercaptopropanol, O-methylmercaptoethanol, mercaptoacetic acid, fl-mercaptopropionic acid, methylmercaptan, S-methylmercaptoethanol, glutathione, glutathione derivatives, and a combination thereof. Preferably, the one or more sulfhydryl compound(s) is selected from the group consisting of cysteine, cystine, and a combination thereof.

Particularly, the one or more sulfhydryl compound(s) may be selected from the group consisting of cysteine, cystine, and a combination thereof. For example, the one or more sulfhydryl compound(s) is cysteine, and the cysteine concentration in the cell culture medium is more than 4.0 mM and less than 10.0 mM, preferably the cysteine concentration is at least 5.0 mM and equal or less than 6.0 mM.

Alternatively (e.g. in the case of cysteine and/or cystine), the cell culture medium for producing a recombinant protein having monogalactosylated or digalactosylated glycans in a mammalian cell comprises 0.5 g/L to 1.2 g/L, preferably 0.6 g/L to 1.2 g/L of one or more sulfhydryl compound(s).

As described herein and in the context of the invention, the cell culture medium may comprise at least more than 3.0 g/L glucose and more preferably at least more than 4.0 g/L glucose. Alternatively, the cell culture medium may comprise at most 13.0 g/L glucose, preferably 8.0 g/L, more preferably at most 7.0 g/L, even more preferably at most 6.0 g/L and most preferably at most 5.0 g/L glucose. Particularly, the cell culture medium as described herein and in the context of the invention may comprise between more than 3.0 g/L and 13 g/L glucose, preferably between more than 3.0 g/L and at most 8.0 g/L glucose, more preferably between more than 3.0 g/L and at most 7.0 g/L glucose, even more preferably between more than 3.0 g/L and at most 6.0 g/L glucose and most preferably between more than 3.0 g/L and at most 5.0 g/L glucose.

As will be recognized by the person skilled in the art, the basal and the feed media used to culture cells for recombinant protein production, as well as other variables such as feeding schedule, growth rate, temperature, and oxygen levels, can affect the yield and quality of the expressed protein. Methods of optimizing these conditions are within the knowledge of the skilled person; exemplary conditions are set forth in the Examples herein. As described herein and in the context of the invention, the cell culture medium is a chemically defined medium, preferably a serum-free, protein-free and/or oligopeptide-free cell culture medium.

Chemically defined media have been extensively developed and published in recent history, including such media for culture of mammalian cells. All components of defined media are well characterized and such media do not contain complex additives such as serum and hydrolysates. Typically, these media include defined quantities of purified growth factors, proteins, lipoproteins and other substances which may otherwise be provided by serum or extract supplement. Such media have been produced with the sole purpose of supporting highly productive cell cultures. Certain defined media may be termed low protein media or may be protein free if the typical components of low protein media, insulin and transferrin, are not included. Serum free media may otherwise be used in the methods of the present invention. Such media normally do not contain serum or protein fractions, but may contain undefined components. Examples of commercially available culture media include Ham's F10 (Sigma). Minimal Essential Medium (MEM, Sigma). RPMI-1640 (Sigma) and Dulbecco's Modified Eagle's Medium (DMEM, Sigma) and chemically defined media and feed supplements sold by Life Technologies. Any such media may be supplemented as necessary with hormones and/or other growth factors (such as insulin, transferrin or epidermal growth factor); salts (such as sodium chloride, calcium, magnesium and phosphate), buffers (such as HEPES); nucleosides (such as adenosine and thymidine), antibiotics (such as GENTAMYCIN™), and glucose or an equivalent energy source. The necessary nutrients and growth factors for the medium including their concentrations, for a particular cell line, are determined empirically and without undue experimentation as described in, for example, Mammalian Cell Culture, Mather (Plenum Press: NY 1984); Barnes and Sato, Cell 22(1980) 649 or Mammalian Cell Biotechnology: A Practical Approach M. Butler (IRL Press, 1991). A suitable medium contains a basal medium component, such as DMEM/HA F12-based formulation with modified concentrations of some components, such as amino acids, salts, sugar and vitamins, and optionally containing glycine, hypoxanthine, thymidine, recombinant human insulin, hydrolyzed peptone, such as PRIMATONE HS" or PRIMATONE RL™ (Sheffield, England) or the equivalent, a cell protective agent, such as PLURONIC F68T or the equivalent pluronic polyol and GENTAMYCIN™.

In another aspect of the present invention, the cell culture medium is a chemically defined medium, preferably a serum-free, protein-free and/or oligopeptide-free cell culture medium; and the cell culture medium comprises 4.0 mM to 10.0 mM of sulfhydryl group(s) from one or more sulfhydryl compound(s). In another preferred aspect, the cell culture medium is a chemically defined medium, preferably a serum-free, protein-free and/or oligopeptide-free cell culture medium; and the cell culture medium comprises at least more than 4.0 mM and equal or less than 9.0 mM, preferably at least more than 4.0 mM and equal or less than 8.0 mM, more preferably at least more than 4.0 mM and equal or less than 7.0 mM and even more preferably at least more than 4.0 mM and equal or less than 6.0 mM of the sulfhydryl group(s) from the one or more sulfhydryl compound(s). In yet another preferred aspect of the present invention, the cell culture medium is a chemically defined medium, preferably a serum-free, protein-free and/or oligopeptide-free cell culture medium; and the cell culture medium comprises at least 5.0 mM and less than 10.0 mM, preferably at least 5.0 mM and equal or less than 9.0 mM, more preferably at least 5.0 mM and equal or less than 8.0 mM, even more preferably at least 5.0 mM and equal or less than 7.0 mM and most preferably at least 5.0 mM and equal or less than 6.0 mM of the sulfhydryl group(s) from the one or more sulfhydryl compound(s).

The concentration of one or more sulfhydryl compound(s) calculated to be in commercial media, as above, will change if those media are supplemented with complex ingredients, such as serum or peptones. When a method of the invention comprises adjusting the concentration of one or more sulfhydryl compound(s) in the culture medium by adding these sulfhydryl compound(s) to the medium, any sulfhydryl compound as provided herein and appropriate for inclusion in a culture medium for the production of a recombinant protein can be used.

FIG. 3 shows the modulating interconversion pathways for UDP-glucose and UDP-galactose in CHO K1 with sulfhydryl compound(s). As shown in FIG. 3, through adding sulfhydryl compound(s), such as L-cysteine, to stimulate UDP-Gal-T, more UDP-galactose may be converted to UDP-glucose, and consequently less UDP-galactose remains in the cytoplasm. As shown in FIG. 4, through adding L-cystine, instead of L-cysteine, to cell culture medium, the effect of stimulating UDP-Gal-T enzymatic activity with L-cysteine may be attenuated in the cytoplasm. On the other hand, the increased L-cystine uptake may provide a more effective redox system for regulating cell survival and improving UDP-galactose metabolic process.

Another aspect of the present invention is the use of simple sulfhydryl molecules, such as L-cysteine and/or cystine, to in vivo regulate intracellular UDP-glucose and UDP-galactose concentration in mammalian cells, such as CHO K1 and its derivative cell lines. For example, L-cystine may be added in culture medium to in vivo regulate intracellular UDP-glucose and UDP-galactose concentration in CHO K1. In this way, the final product quantity and quality can be controlled and improved for pre-defined clinical applications.

Modulating UDP-Glucose/UDP-Galactose Pathway to Control Product Glycosylation and Cell Culture Process As shown in FIG. 5, UDP-galactose acts as galactosyl donor in different galactosylation reactions catalyzed by glycosyltransferases. For example, UDP-α-D-galactose: N-acetyl-β-D-glucosaminylglycopeptide 4-β-galactosyl-transferase (EC 2.4.1.38) catalyzes the formation of Galβ1-4GlcNAc linkages by transferring galactosyl group from UDP-galactose to GlcNAc (Qasba et al., Curr. Drug. Targets. 9 (2008) 292-309).

Increased L-cysteine in cytoplasm may stimulate enzyme UDP-Gal-T to convert more UDP-galactose to UDP-glucose resulting in a reduced cytoplasmic pool of UDP-galactose for the subsequent galactosylation reaction. On the other hand, in the presence of L-cystine, instead of L-cysteine, in cell culture medium, L-cystine is transported through system xc into the cells. With increased L-cystine uptake, enzyme UDP-Gal-T stimulation may be attenuated, resulting in a balanced cytoplasmic pool of UDP-galactose for the subsequent galactosylation reaction. According to the present invention, the concentration of one or more sulfhydryl compound(s) is controlled to affect the galactosylation pattern of the recombinant protein produced by a mammalian cell. Concentrations of one or more sulfhydryl compound(s) with sulfhydryl group(s) ranging between about 4 mM to 10 mM, may be used and modified according to the particular host cell being cultured and the desired galactosylation pattern of the recombinant protein produced. In order to produce a protein with the desired galactosylation pattern a concentration of one or more sulfhydryl compound(s) is chosen which provides for a constant homogeneous galactosylation pattern of the recombinant protein. To increase the galactosylation content of the recombinant protein, generally, a lower concentration provides for enhanced galactosylation content while maintaining the viability of the mammalian host cell culture. Generally, concentrations of the one or more sulfhydryl compound(s), such as cysteine and/or cystine, with sulfhydryl group(s) ranging between about 4 mM to 10 mM, preferably between about 5 mM to 10 mM, are used. More preferably, concentrations between about least 5.0 mM and equal or less than 9.0 mM, more preferably between about at least 5.0 mM and equal or less than 8.0 mM, even more preferably between about at least 5.0 mM and equal or less than 7.0 mM and most preferably between about at least 5.0 mM and equal or less than 6.0 mM, are used. Alternatively (e.g. in the case of cysteine and/or cystine), concentrations between about at least 0.6 g/L and equal or less than 1.1 g/L, more preferably between about at least 0.6 g/L and equal or less than 1.0 g/L, more preferably between about at least 0.6 g/L and equal or less than 0.9 g/L, even more preferably between about at least 0.6 g/L and equal or less than 0.8 g/L, and most preferably between about at least 0.6 g/L and equal or less than 0.7 are used.

As used herein, the term "concentration" in relation to the one or more sulfhydryl compound(s) refers to the total concentration of all sulfhydryl compound(s) comprised within a culture medium. As used herein, the term "concentration" in relation to the sulfhydryl group refers to the total concentration of all sulfhydryl compound(s) comprised within a culture medium. In this context, a sulfhydryl group refers to —SH (herein also referred to as "[—SH]") and may also refer to a sulfhydryl group which has undergone a reaction, wherein the hydrogen dissociates from the sulfur atom of the sulfhydryl group and said sulfur atom forms a S—S bond with another sulfhydryl group which has undergone said reaction. In other words, the term "sulfhydryl group" also includes sulfhydryl group(s) which have been linked, e.g. by a disulfide bridge. The concentration may be measured or measurable or the calculated or calculable actual concentration of the sulfhydryl compound(s) in the medium surrounding the cells at a given point in time. Methods for measuring the concentration of these sulfhydryl compound(s) in the medium are known in the art. Examples of such methods include PCI-MS (Agilent, Boblingen, Germany). The concentration thus also refers to the amount of sulfhydryl compound(s) comprised in a culture medium surrounding the cells during culture, and is thus the actual concentration of the respective sulfhydryl compound(s) at a given point in time. This concentration can be determined analytically and results from e.g. the introduction of the sulfhydryl compound(s) into the culture (by weighing, by transferring cells and medium from a pre-culture, by introduction of impurities, by leaching etc.), from release by cells (e.g. by the death of cells or by active secretion), from uptake by cells and other factors.

As used in the context of the present invention, the cell culture medium comprises an elevated level of the one or more sulfhydryl compound(s) compared to a cell culture medium not comprising the elevated level of the one or more sulfhydryl compound(s).

Particularly, the invention relates to a method of producing a glycoprotein, such as a recombinant protein or an antibody, particularly anti-CD20/anti-CD3 bispecific antibody or anti α-synuclein antibody, wherein said method comprises (a) cultivating a mammalian cell as described herein in a cell culture medium as described herein, wherein a concentration of at least more than 4.0 and less than 10.0 mM of the sulfhydryl group(s) from one or more sulfhydryl compound(s) and at least more than 3.0 g/L glucose in the cell culture medium is maintained for at least 3, more preferably for at least 4 and even more preferably for at least 5 days, (b) isolating said antibody.

In the context of the method of the present invention, the recombinant protein has an increased level of monogalactosylated or digalactosylated glycans relative to a corresponding level of the recombinant protein produced using the medium not comprising the elevated level of one or more sulfhydryl compound(s). As used in the context of the method of the present invention, the recombinant protein has an increased level of monogalactosylated or digalactosylated glycans by at least 3%, more preferably by at least 5%, even more preferably by at least 10%. As used in the context of the method of the present invention, the titer of the produced recombinant protein is increased relative to the titer of a corresponding recombinant protein produced using the medium not comprising the elevated level of one or more sulfhydryl compound(s). Preferably, the titer of the produced recombinant protein is at least 2000 mg/L.

As used in the context of the method of the present invention, the viable cell density of the cell in the cell culture medium is increased relative to a corresponding viable cell density of a cell in the medium not comprising the elevated level of one or more sulfhydryl compound(s). Preferably, the maximal viable cell density of the cell in the cell culture medium is at least about $120 \times 10^5$ cells/mL.

For example, the recombinant protein may be an anti-CD20/anti-CD3 bispecific antibody having 19.0-29.0% (w/w) of G1 and 1.3-2.8% (w/w) of G2 per total glycan; preferably 20.0-28.0% (w/w) of G1 and 1.4-2.7% (w/w) of G2 per total glycan; more preferably 21.0-28.0% (w/w) of G1 and 1.5-2.7% (w/w) of G2 per total glycan and most preferably 21.0-27.4% (w/w) of G1 and 1.5-2.6% (w/w) of G2 per total glycan. Said cultivation of the mammalian cell may result in an increased titer of said antibody by at least 20%, preferably at least 30%, more preferably at least 40%, more preferably at least 50%, even more preferably at least 60%, and most preferably at least 80% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium.

As another example, the recombinant protein may be anti α-synuclein antibody having 17.2-48.0% (w/w) of G1 and 3.1-15.0% (w/w) of G2 per total glycan 25.4-48.0% (w/w) of G1 and 3.5-15.0% (w/w) of G2 per total glycan; preferably 27.2-47.0% of G1 and 4.4 to 15.0% of G2 per total glycan; preferably 40.0-46.0% of G1 and 8.4-15.0% (w/w) of G2 per total glycan; more preferably 41.0-45.0% (w/w) of G1 and 9.5-14.0% (w/w) of G2 per total glycan and most preferably 42.1-43.9% (w/w) of G1 and 10.6-13.3% (w/w) of G2 per total glycan. Said cultivation of the mammalian cell may result in an increased titer of said antibody by at least 10%, preferably at least 20%, more preferably at least 30%, more preferably at least 40%, more preferably at least 50%, more preferably at least 60%, more preferably at least 70%, even more preferably at least 80% and most preferably at least 100% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium. As another example, said cultivation of the mammalian cell may result in an increased titer of said antibody between 9.0 and 75% relative to the titer in a corresponding cultivation of the mammalian cell without maintaining the concentration of at least more than 4.0 and less than 10.0 mM of the sulfhydryl group(s) from the one or more sulfhydryl compound(s) in the cell culture medium.

Further, said cultivation of the mammalian cell results in the anti α-synuclein antibody having monogalactosylated (G1) and digalactosylated (G2) glycans characterized by (i) increased protein target binding by at least 10/c, preferably at least 20%, more preferably at least 35%, even more preferably at least 45% and most preferably at least 50%;

(ii) increased neonatal Fc receptor (FcRn) binding by at least 10%, preferably at least 20%, more preferably at least 33%, more preferably at least 40% and most preferably at least 45%; and/or;

(iii) increased FcγRIIa binding by at least 10%, preferably at least 20%, more preferably at least 36%, even more preferably 45% and most preferably 50%, relative to the non-monogalactosylated (G1) and non-diga-lactosylated (G2) forms of the anti α-synuclein antibody in a corresponding cultivation of the mammalian cell without maintaining the concentration of the at least more than 4.0 and less than 10.0 mM of sulfhydryl group(s) from the one or more sulfhydryl compound(s) in the cell culture medium.

"Recombinant protein" or "recombinantly expressed protein" as used herein refers to a protein expressed from a host cell manipulated for the purposes of such expression. Manipulation includes one or more genetic modifications such as introduction of one or more heterologous genes encoding the protein to be expressed. The heterologous gene may encode a protein either that is normally expressed in that cell or that is foreign to the host cell. Manipulation may alternatively be to up- or down-regulate one or more endogenous genes. As used in the context of the present invention, the recombinant protein has monogalactosylated or digalactosylated glycans. As used herein, the term "glycan" of a recombinant protein refers to a glycoprotein. As used herein, "glycoprotein" refers generally to peptides and proteins having more than about ten amino acids and at least one oligosaccharide side chain. The glycoproteins may be homologous to the host cell, or preferably, they are heterologous, i.e., foreign, to the host cell being utilized, such as a human protein produced by a Chinese hamster ovary (CHO) cell. Preferably, mammalian glycoproteins (glycoproteins that were originally derived from a mammalian organism) are used, more preferably, those which are directly secreted into the medium. Examples of mammalian glycoproteins include molecules such as cytokines and their receptors, as well as chimeric proteins comprising cytokines or their receptors, including, for instance tumor necrosis factor alpha and beta, their receptors and their derivatives; a growth hormone, including human growth hormone, and bovine growth hormone; growth hormone releasing factor; parathyroid hormone: thyroid stimulating hormone; lipoproteins; alpha-1-antitrypsin; insulin A-chain; insulin B-chain; proinsulin; follicle stimulating hormone: calcitonin; luteinizing hormone; glucagon; clotting factors such as factor VIIIC, factor IX tissue factor, and von Willebrands factor; anti-clotting factors such as Protein C: atrial natriuretic factor; lung surfactant; a plasminogen activator, such as urokinase or human urine or tissue-type plasminogen activator (t-PA); bombesin; thrombin; hemopoietic growth factor: enkephalinase: RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors: integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3. CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; chimeric proteins, such as immunoadhesins, and fragments of any of the above-listed polypeptides. "Galactosylated" as used herein in respect of glycoproteins, refers to glycoprotein comprising one or more galactose residues, resulting in G1 and G2 glycostructures. For example, galactosylated recombinant proteins having monogalactosylated or digalactosylated glycans that contain one or more sialic acid residues, such as $GlcNAc_3Man_3GlcNAc_2Gal$, $GlcNAc_3Man_3GlcNAc_2Gal_2$, $GlcNAc_3Man_3GlcNAc_2GalSiai$, $GlcNAc_3Man_3GlcNAc_2Gal_2Siai$ and $GlcNAc_3Man_3GlcNAc_2Gal_2Siai_2$.

In one aspect used in the context of the present invention, the recombinant protein is an antibody. As used herein, the term "antibody" (Ab) refers to an immunoglobulin molecule or an immunologically active portion of an immunoglobulin molecule, i.e. a molecule that contains an antigen binding site, such as a Fab or $F(ab')_2$ fragment, whether natural or partly or wholly synthetically produced. The term "antibody" is used in its broadest sense and covers various antibody structures, including but not limited to monoclonal antibodies (including full length antibodies which have an immunoglobulin Fc region or intact monoclonal antibodies), antibody compositions with polyepitopic specificity, polyclonal antibodies, multivalent antibodies (typically engineered to have three or more antigen binding sites), multispecific antibodies (e.g. bispecific antibodies) formed from at least two intact antibodies, diabodies and single chain molecules such as scFv molecules, as well as antibody fragments (e.g. Fab, F(ab')2 and Fv) so long as they exhibit the desired antigen-binding activity. "Multispecific antibodies" are monoclonal antibodies that have binding specificities for at least two different sites, i.e., different epitopes on different antigens or different epitopes on the same antigen. Multispecific antibodies may be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Multi-specific antibodies may also be made by engineering electrostatic steering effects for making antibody Fc-heterodimeric molecules (see, e.g., WO 2009/089004); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992) and WO 2011/034605); using the common light chain technology for circumventing the light chain mis-pairing problem (see, e.g., WO 98/50431); using "diabody" technology for making bispecific antibody fragments (see, e.g., Hollinger et al., *Proc. Natl. Acad. Sci. USA,* 90:6444-6448 (1993)); and using single-chain Fv (sFv)

dimers (see, e.g., Gruber et al., *J. Immunol.*, 152:5368 (1994)); and preparing trispecific antibodies as described, e.g., in Tutt et al. *J. Immunol.* 147: 60 (1991).

Included within the definition of antibody are antibody conjugates, such as antibody drug conjugates (ADCs) or antibodies conjugated to e.g. labeling elements. Further included within the definition of antibody are antibodies binding with sufficient affinity to a particular target protein such that the antibody is useful as a diagnostic and/or therapeutic agent in targeting a particular protein. For example, the antibody may be an anti-α synuclein antibody capable of binding a synuclein with sufficient affinity such that the antibody is useful as a diagnostic and/or therapeutic agent in targeting a synuclein.

As another example, the antibody may be an anti-CD20/anti-CD3 antibody capable for binding CD20-CD3 with sufficient affinity such that the antibody is useful as a diagnostic and/or therapeutic agent in targeting CD20-CD3. In one aspect, the extent of binding of an antibody to an unrelated, non-target protein is less than about 10% of the binding of the antibody to a target as measured, e.g., by surface plasmon resonance (SPR). In certain aspects, an antibody that binds to a target has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). An antibody is said to "specifically bind" to a target when the antibody has a $K_D$ of 1 μM or less. In certain aspects, an antibody binds to an epitope of a target that is conserved among targets from different species. In another aspect as used in the context of the present invention, the recombinant protein is a therapeutic protein. For example, when the recombinant protein is an antibody, the antibody could be a therapeutically effective antibody and may bind to any protein, including a member of the angiopoietin family, such as Ang1, Ang2, Ang3 and Ang4 and antibodies bi-specific for a member of the angiopoietin family and e.g. VEGF, such as Ang2/VEGF; a member of the HER receptor family, such as HER1 (EGFR), HER2, HER3 and HER4: CD proteins such as CD3, CD4, CD8, CD18, CD19. CD20, CD21, CD22, CD25, CD33, CD34, CD38, CD40, CD44 and CD52; cell adhesion molecules, such as LFA-1, VLA04, ICAM-1, VCAM and an integrin, including either α or β subunits thereof (e.g. anti CD11 α, anti CD 18 or anti CD11 β antibodies); growth factors such as vascular endothelial growth factor (VEGF); cytokine receptors such as thymic stromal lymphopoietin receptor (TSLP-R); IgE; blood group antigens; flk2/flt3 receptor; obesity (OB) receptor and protein C. Other exemplary proteins include growth hormone (GH), including human growth hormone (hGH) and bovine growth hormone (bGH); growth hormone releasing factor; parathyroid hormone, thyroid stimulating hormone; lipoproteins; insulin A chain; insulin B chain; proinsulin, follicle stimulating hormone; calcitonin; luteinizing hormone; glucagon; clotting factors such as factor VIIIC: tissue factor (TF); von Willebrands factor; atrial natriuretic factor: lung surfactant; a plasminogen activator such as urokinase or tissue-type plasminogen activator (t-PA), bombazine, thrombin, tumour necrosis factor-α and -β; enkephalinase; RANTES (regulated on activation normally T-cell expressed and secreted); human macrophage inflammatory protein (MIP-1-α): serum albumin such as human serum albumin (HSA); mullerianinhibiting substance; relaxin A-chain, relaxin B-chain; prorelaxin: mouse gonadotropin-associated peptide; DNase; inhibin; activin; receptors for hormones or growth factors; protein A or D; fibroblast activation protein (FAP); carcinoembryonic antigen (CEA): rheumatoid factors: a neurotrophic factor such as bone-derived neurotrophic factor (BDNF): neurotrophin-3, -4, -5 or -6 (NT-3, NT-4, NT-5 or NT-6) or a nerve growth factor such as NGF-β; platelet-derived growth factor (PDGF); fibroblast growth factor such as aFGF and bFGF; epidermal growth factor (EGF) and epidermal growth factor receptor (EGFR); transforming growth factor (TGF) such as TGF-α and TGF-β, including TGF-1, TGF-2, TGF-3, TGF-4 or TGF-βδ; insulinlike growth factor-I and -II (IGF-I and IGF-II); des(1-3)-IGF-1 (brain IGF-I): insulin-like growth factor binding proteins (IGFBPs); erythropoietin (EPO); thrombopoietin (TPO); osteoinductive factors, immunotoxins; a bone morphogenetic protein (BMP); an interferon (interferon-α, -β or -γ); colony stimulating factors (CSFs) e.g. M-CSF, GM-CSF and G-CSF; interleukins (ILs), e.g. IL-1 to IL-10 and IL-17; superoxide dismutase; T-cell receptors; BlyS (Br3) receptor; Br3-Fc immunoadhesin; Apo-2 receptor; Fc receptor; surface membrane proteins; decay accelerating factor (DAF); a viral antigen, such as for example a portion of the AIDS envelope; transport proteins; homing receptors: addressins: regulatory proteins: immunoadhesins; and biologically active fragments or variants of any of the above. Alternatively, the antibody could be an antibody directed against breast epithelial cells or binding to colon carcinoma cells, anti-EpCAM antibodies, anti-GpIIb/IIIa antibodies, anti-RSV antibodies, anti-CMV antibodies, anti-HIV antibodies, anti-hepatitis antibodies, anti-CA 125 antibodies, anti-human renal cell carcinoma antibodies, anti-human colorectal tumour antibodies, anti-human melanoma antibody R24 directed against GD3 ganglioside, anti-human squamous-cell carcinoma, anti-human leukocyte antigen (HLA) antibodies, anti-HLA DR antibodies.

As used herein, the terms "antigen" and "epitope" are used interchangeably and refer to a site (e.g. a contiguous stretch of amino acids or a conformational configuration made up of different regions of non-contiguous amino acids) on an antigen, either proteinaceous or non-proteinaceous, to which an antibody binding moiety binds, forming an antibody binding moiety-antigen complex. Thus, an epitope is a region of an antigen that is bound by an antibody. Epitopes can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

In certain embodiments, epitope determinant includes chemically active surface groupings of molecules such as amino acids, sugar side chains, phosphoryl, or sulfonyl, and, in certain embodiments, may have specific three-dimensional structural characteristics, and or specific charge characteristics. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form of proteins from any vertebrate source, including mammals such as primates (e.g. humans) and rodents (e.g. mice and rats), unless otherwise indicated. Screening for antibodies binding to a particular epitope (i.e., those binding to the same epitope) can be done using methods routine in the art such as, e.g., without limitation, alanine scanning, peptide blots (see Meth. Mol. Biol. 248 (2004) 443-463), peptide cleavage analysis, epitope excision, epitope extraction, chemical modification of antigens (see Prot. Sci. 9 (2000) 487-4%), and cross-blocking (see "Antibodies", Harlow and Lane (Cold Spring Harbor Press, Cold Spring Harb., NY).

In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. In other words, the term also encompasses an antibody having a structure substantially similar to a native antibody structure or having heavy chains that contain an Fc region as defined herein.

By "antigen-binding" it is meant that an antigen-binding site of the part of the antibody specifically binds to an antigen. In other words, the term "antigen-binding site" refers to the part of an antibody that comprises the area which specifically binds to and is complementary to part or all of an antigen. By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to the person skilled in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)).

The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. The "variable domain" (variable domain of a light chain (VL), variable domain of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). (See, e.g., Kindt et al. *Kuby Immunology*, 6*th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991). The term "hypervariable region" or "HVR" as used herein refers to each of the regions of an antibody variable domain which are hypervariable in sequence and which determine antigen binding specificity, for example "complementarity determining regions" ("CDRs"). Unless otherwise indicated, the CDRs are determined according to Kabat et al., supra. One of skill in the art will understand that the CDR designations can also be determined according to Chothia, supra, McCallum, supra, or any other scientifically accepted nomenclature system.

The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention. Unless otherwise specified herein, numbering of amino acid residues in the variable region or constant region is according to the EU numbering system, also called the EU index, as described in Kabat et al., Sequences of Proteins of Immunological Interest, 5*th* Ed. Public Health Service, National Institutes of Health, Bethesda, MD, 1991. "Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4. With the exception of CDR1 in VH, CDRs generally comprise the amino acid residues that form the hypervariable loops. CDRs also comprise "specificity determining residues," or "SDRs", which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of HI, 50-58 of H2, and 95-102 of H3. (See Almagro and Fransson, Front. Biosci. 13: 1619-1633 (2008).

As indicated above, the term antibody herein, unless otherwise stated or clearly contradicted by context, includes full-length antibody and fragments of an antibody that are antigen-binding fragments, i.e., retain the ability to specifically bind to the antigen. In other words, the term "fragment" as used herein refers to a molecule other than an intact antibody that comprises a portion of an intact antibody that binds the antigens to which the intact antibody binds. Examples of antibody fragments include but are not limited to (i) a Fab' or Fab fragment; diabodies, linear antibodies; single-chain antibody molecules (e.g., scFv, and scFab), multispecific antibodies formed from antibody fragments, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region: (iii) a Fd fragment consisting essentially of the $V_H$ and CH1 domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al: Trends Biotechnol. 2003 November; 21(11):484-90); (vi) camelid or nanobodies (Revets et al; Expert Opin Biol Ther. 2005 January; 5(1): 111-24) and (vii) an isolated complementarity determining region (CDR). Pepsin treatment yields an F(ab')$_2$ fragment that has two antigen-binding sites (two Fab fragments) and a part of the Fc region. For discussion of Fab and F(ab')$_2$ fragments comprising salvage receptor binding epitope residues and having increased in vivo half-life, see U.S. Pat. No. 5,869,046. "Diabodies" are antibody fragments with two antigen-binding sites that may be bivalent or bispecific. See, for example, EP 404,097: WO 1993/01161: Hudson et al., Nat. Med. 9:129-134 (2003); and Hollinger et al., Proc. Natl. Acad. Sci. USA 90: 6444-6448 (1993). Furthermore, although the two domains of the Fv fragment, $V_L$ and $V_H$, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Thus, a "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA: see, e.g., U.S. Pat. No. 6,248,516 B1). Antibody fragments can be made by various techniques, including but not limited to proteolytic digestion of an intact antibody as well as recombinant production by recombinant host cells (e.g., *E. coli*), as described herein.

Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. For a review of certain antibody fragments, see Holliger and Hudson, Nature Biotechnology 23:1126-1136 (2005).

The term "full-length antibody" denotes an antibody consisting of two "full-length antibody heavy chains" and two "full-length antibody light chains". A "full-length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full-length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. The "class" of an antibody refers to the type of constant domain or constant region possessed by its heavy chain. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. The heavy chain constant domains that correspond to the different classes of immunoglobulins are called α, δ, ε, γ, and μ, respectively. The light chain of an antibody may be assigned to one of two types, called kappa (κ) and lambda (λ), based on the amino acid sequence of its constant domain.

It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. The term "chimeric" antibody refers to an antibody in which a portion of the heavy and/or light chain is derived from a particular source or species, while the remainder of the heavy and/or light chain is derived from a different source or species.

For example, the antibody may be a monoclonal antibody. The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

As another example, the antibody may be a humanized antibody. The term "humanized antibody" refers to antibodies in which the framework or "complementarity determining regions" (CDR) have been modified to comprise the CDR of an immunoglobulin of different specificity as compared to that of the parent immunoglobulin. In other words, the term encompasses a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Methods for producing humanized antibodies involve conventional recombinant DNA and gene transfection techniques are well known in the art. See, e.g., Riechmann, L., et al., Nature 332 (1988) 323-327; and Neuberger, M. S., et al., Nature 314 (1985) 268-270.

As another example, the antibody may be a human antibody. The term "human antibody", as used herein, is intended to include antibodies having variable and constant regions derived from human germ line immunoglobulin sequences. In other words, the term encompasses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies are well-known in the state of the art (van Dijk, M. A., and van de Winkel, J. G., Curr. Opin. Chem. Biol. 5 (2001) 368-374). Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immuno-globulin loci, which replace the endogenous immunoglobu-lin loci, or which are present extrachromosomally or inte-grated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modi-fied, e.g., by combining with a different human constant region.

Human antibodies can also be made by hybridoma-based methods. Human myeloma and mouse-human heteromy-eloma cell lines for the production of human monoclonal antibodies have been described. (See, e.g., Kozbor J. Immu-nol., 133: 3001 (1984); Brodeur et al., Monoclonal Antibod Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclo-nal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating variable domain sequences selected from human-derived phage display libraries. Such variable domain sequences may then be combined with a desired human constant domain. Techniques for selecting human antibodies from antibody libraries are described below.

In one aspect used in the context of the present invention, the recombinant protein is anti α-synuclein antibody or bispecific antibody directed to CD3 and CD20, also denoted anti-CD20/anti-CD3 bispecific antibody. The term "bispe-cific antibody" in the context of the present invention refers to an antibody having two different antigen-binding regions defined by different antibody sequences. Examples of bis-pecific antibody formats that may be useful for this purpose include, but are not limited to, the so-called "BiTE" (bis-pecific T cell engager) molecules wherein two scFv mol-ecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-ter-minal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmu-nology 5(8) (2016) e1203498.

The terms "anti α-synuclein antibody". "anti-α-synuclein antibody" and "an antibody that binds to α-synuclein" refer to an antibody that is capable of binding human alpha-synuclein with sufficient affinity such that the antibody is useful as a diagnostic and/or therapeutic agent in targeting α-synuclein. α-synuclein is a protein which in the brain plays a central role in the control of dopaminergic neuronal functions and which is thought to be critically implicated in Parkinson's Disease (PD) pathophysiology. For example, Synucleinopathies also known as Lewy body diseases (LBDs), are characterized by degeneration of the dopamin-ergic system, motor alterations, cognitive impairment, and formation of Lewy bodies (LBs) and/or Lewy neurites. (McKeith et al., Neurology (1996) 47:1113-24) and may be treated with anti α-synuclein antibody. Such synucleinopa-thies include Parkinson's disease (including idiopathic Par-kinson's disease). Diffuse Lewy Body Disease (DLBD) also known as Dementia with Lewy Bodies (DLB), Lewy body variant of Alzheimer's disease (LBV), Combined Alzheim-er's and Parkinson disease, pure autonomic failure and multiple system atrophy (MSA; e.g., Olivopontocerebellar Atrophy, Striatonigral Degeneration and Shy-Drager Syn-drome). Alpha-synuclein is part of a large family of proteins including beta- and gamma-synuclein and synoretin. Natural human wildtype alpha-synuclein is a peptide of 140 amino acids having the following amino acid sequence:

MDVFMKGLSK AKEGVVAAAE KTKQGVAEAA
GKTKEGVLYV GSKTKEGVVH GVATVAEKTK
EQVTNVGGAV VTGVTAVAQK TVEGAGSIAA
ATGFVKKDQL GKNEEGAPQE GILEDMPVDP
DNEAYEMPSE EGYQDYEPEA (SEQ ID NO:9)

(Ueda et al., Proc. Natl. Acad. Sci. USA (1993) 90:11282-6); GenBank accession number: P37840). The protein has three recognized domains, a KTKE repeat domain covering amino acids 1-61, a NAC (Non-amyloid component)

domain running from about amino acids 60-95, and a C-terminal acidic domain running from about amino acid 98 to 140, reference to alpha-synuclein or its fragments includes the natural human wildtype amino acid sequences indicated above, and human allelic variants thereof, particularly those associated with Lewy body disease (e.g., E46K, A30P and A53T, with the first letter indicates the amino acid in SEQ ID NO:9, the number is the codon position in SEQ ID NO:9, and the second letter is the amino acid in the allelic variant).

Alpha-synuclein is expressed in the normal state associated with synapses and is believed to play a role in neural plasticity, learning and memory. Several studies have implicated alpha-synuclein with a central role in PD pathogenesis. The protein can aggregate to form insoluble fibrils in pathological conditions. For example, synuclein accumulates in LBs (Spillantini et al., Nature (1997) 388:83940; Takeda et al., J. Pathol. (1998) 152:367-72: Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polymeropoulos, et al., Science (1997) 276:2045-7). Over expression of alpha synuclein in transgenic mice (Masliah et al., Science (2000) 287:1265-9) and *Drosophila* (Feany et al., Nature (2000) 404:394-8) mimics several pathological aspects of Lewy body disease. In addition, it has been suggested that soluble oligomers of synuclein may be neurotoxic (Conway K A, et al., Proc Natl Acad Sci USA (2000) 97:571-576; Volles M J, Lansbury P T, Jr Biochemistry (2003) 42:7871-7878). The accumulation of alpha-synuclein with similar morphological and neurological alterations in species and animal models as diverse as humans, mice, and flies suggests that this molecule contributes to the development of Lewy body disease.

For example, the anti α-synuclein antibody may be an antibody denoted as 9E4 (prasinezumab), BIIB054, 1H7, 5C1, 6H7, 8A5, and NI-202.21D11 and related antibodies thereof. Prasinezumab or 9E4 is also known publicly as PRX002 and RG7935. As illustrated in the appended Examples, CHO L965 cells (Example 3), CHO L967 cells (Example 6) and CHO L971 cells (Examples 7 and 8) each produce Prasinezumab. References to such antibodies may be found in the art, for example 9E4 (prasinezumab) and related antibodies thereof may be found in U.S. Pat. Nos. 8,609,820; 9,556,259; 9,884,906; 8,697,082; 8,506,959; 9,034,337; 7,919,088; 8,092,801; 8,147,833; 8,673,593; 7,910,333 and 7,674,599. References to BIIB054, also known as NI-202.12F4, and related antibodies thereof may be found, for example, in U.S. Pat. Nos. 10,301,381; 9,975, 947; 8,896,504; 9,580,493 and 8,940,276. References to 1H7 and related antibodies thereof may be found, for example, in U.S. Pat. Nos. 7,910,333; 8,790,644; 9,234,031; 9,217,030; 9,670,273 and 10,118,960. References to 5C1 and related antibodies thereof may be found, for example, in U.S. Pat. Nos. 9,605,056; 10,081,674 and 10,301,382. References to 6H7 and related antibodies thereof may be found, for example, in U.S. Pat. Nos. 8,673,593 and 7,910,333. References to 8A5 and related antibodies thereof may be found, for example, in U.S. Pat. Nos. 8,673,593 and 7,910, 333. References to NI-202.21D11 and related antibodies thereof may be found, for example, in U.S. Pat. No. 9,580, 493.

Particularly, patients with Parkinson's disease and related disorders may be treated with anti α-synuclein antibody. Indeed, besides the fact that α-synuclein is the main protein component of Lewy bodies (LB), genetic studies showed that certain point mutations in and multiplications of the α-synuclein gene cause familial forms of PD. A large body of evidence indicates that α-synuclein pathology at dopaminergic synapses may underlie the onset of neuronal cell dysfunction and degeneration in the PD brain (Bellucci, A., et al., Brain Res. 1432 (2012) 95-113).

The term "CD20" refers to human CD20 (UniProtKB/Swiss-Prot No P11836) and includes any variants, isoforms and species homologs of CD20 which are naturally expressed by cells, including tumor cells, or are expressed on cells transfected with the CD20 gene or cDNA. The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) J. Biol. Chem. 264(19): 11282-11287; and Einfield et al., (1988) EMBO J. 7(3): 711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular. CD20 is expressed on greater than 90% of B cell non-Hodgkin's lymphomas (NHL) (Anderson et al. (1984) Blood 63(6): 1424-1433), but is not found on hematopoietic stem cells, pro-B cells, normal plasma cells, or other normal tissues (Tedder et al. (1985) J. Immunol. 135(2):973-979).

The term "CD3" as used herein, refers to the Cluster of Differentiation 3 protein which is part of the T-cell co-receptor protein complex and is composed of four distinct chains. CD3 is also found in human and also other species, and thus, the term "CD3" may be used herein and is not limited to human CD3 unless contradicted by context. In mammals, the complex contains a CD3y (gamma) chain (human CD3y chain UniProtKB/Swiss-Prot No P09693, or cynomolgus monkey CD3y UniProtKB/Swiss-Prot No Q95L17), a CD36 (delta) chain (human CD36 UniProtKB/Swiss-Prot No P04234, or cynomolgus monkey CD36 UniProtKB/Swiss-Prot No Q95LI8), two CD3s (epsilon) chains (human CD3s UniProtKB/Swiss-Prot No P07766; cynomolgus CD3s UniProtKB/Swiss-Prot No Q95LI5; or rhesus CD3s UniProtKB/Swiss-Prot No G7NCB9), and a zeta chain (human CD3ζ UniProtKB/Swiss-Prot No P20963, cynomolgus monkey CD3ζ UniProtKB/Swiss-Prot No Q09TK0). These chains associate with a molecule known as the T-cell receptor (TCR) and generate an activation signal in T lymphocytes. The TCR and CD3 molecules together comprise the TCR complex.

According to the present invention, mammalian cells are cultured to produce a recombinant protein having monogalactosylated or digalactosylated glycans. In choosing a host cell for the production of the recombinant protein within the context of the present invention, the person skilled in the art recognizes that different host cells have different properties and/or specific mechanisms for the translational and post-translational processing and modification of the expressed protein, such as but not limited to glycosylation and cleavage. In this context, the skilled person knows how to select an appropriate cell line within the context of the present invention. In other words, the skilled person knows which cell line should be chosen to ensure that the post translational modifications are possible. Alternatively, the host cell may be modified by means required for the specific post translational modification in order to express the recombinant protein having monogalactosylated or digalactosylated glycans. Recombinant methods for producing recombinant proteins, such as antibodies may be produced, e.g., as described in U.S. Pat. No. 4,816,567. For these methods one or more isolated nucleic acid(s) encoding an antibody are provided. In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g., Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to EU index numbering.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. Suitable host cells for cloning or expression of antibody-encoding vectors include prokaryotic or eukaryotic cells described herein. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*.) After expression, the antibody may be isolated from the bacterial cell paste in a soluble fraction and can be further purified.

The terms "mammalian host cell". "mammalian host cell line", and "mammalian host cell culture" are used interchangeably and refer to cell lines derived from mammals that are capable of growth and survival when placed in either monolayer culture or in suspension culture in a medium containing the appropriate nutrients and growth factors. The necessary growth factors for a particular cell line are readily determined empirically without undue experimentation, as described for example in Mammalian Cell Culture (Mather, J. P. ed., Plenum Press, N.Y. 119841), and Barnes and Sato. ((1980) Cell. 22:649). Typically, the cells are capable of expressing and secreting large quantities of a particular glycoprotein of interest into the culture medium. Examples of suitable mammalian host cells within the context of the present invention may include Chinese hamster ovary cells/-DHFR (CHO. Urlaub and Chasm. Proc. Natl. Acad. Sci. USA. 77:4216 [1980]); dp12. CHO cells (EP 307.247 published 15 Mar. 1989): monkey kidney CV1 line transformed by SV40 (COS-7, ATCC CRL 1651); human embryonic kidney line (293 or 293 cells subcloned for growth in suspension culture, Graham et al., J. Gen Virol., 36:59 [1977]); baby hamster kidney cells (BHK, ATCC CCL 10); mouse sertoli cells (TM4, Mather, Biol. Reprod., 23:243-251 [1980]); monkey kidney cells (CV1 ATCC CCL 70): African green monkey kidney cells (VERO-76, ATCC CRL-1587); human cervical carcinoma cells (HELA, ATCC CCL 2); canine kidney cells (MDCK. ATCC CCL 34): buffalo rat liver cells (BRL 3A, ATCC CRL 1442); human lung cells (W138. ATCC CCL 75); human liver cells (Hep G2, HB 8065): mouse mammary tumor (MMT 060562. ATCC CCL51); TRI cells (Mather et al., Annals N.Y. Acad. Sci., 383:44-68 [1982]): MRC 5 cells: FS4 cells; and a human hepatoma line (Hep G2). In a preferred aspect of the present invention, the mammalian cells are selected from the group consisting of CHO cells, Vero cells, BHK cells, COS cells and HEK293/293T cells, more preferably the mammalian cells are CHO cells. More preferably, the mammalian host cell is a CHO cell, even more preferably a CHO cell lacking dihydrofolate reductase (DHFR) activity. The mammalian cell used in the present invention may be selected or manipulated to produce a recombinant protein. Manipulation includes one or more genetic modifications such as introduction of one or more heterologous genes encoding the protein to be expressed. The heterologous gene may encode a protein either that is normally expressed in that cell or that is foreign to the host cell. Manipulation may additionally or alternatively be to up- or down-regulate one or more endogenous genes. Often, cells are manipulated to produce recombinant protein by, for example, introduction of a gene encoding the protein and/or by introduction of control elements that regulate expression of the gene encoding the protein of interest. Genes encoding recombinant proteins and/or control elements may be introduced into the host cell via vectors, such as a plasmid, phage or viral vector. The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Certain vectors are capable of autonomous replication in a host cell into which they are introduced whilst other vectors can be integrated into the genome of a host cell and are thereby replicated along with the host genome. Various vectors are publicly available and the precise nature of the vectors is not essential to the present invention. Typically vector components include one or more of a signal sequence, an origin of replication, one or more marker genes, a promoter and a transcription termination sequence. Such components are as described in WO 97/25428.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives. Further, culture conditions, such as temperature, pH, dissolved oxygen ($dO_2$) and the like, are those used with the particular host and will be apparent to the person skilled in the art. Generally, the pH is adjusted using either an acid (e.g. $CO_2$) or a base (e g. $Na_2CO$, or NaOH). A suitable temperature range for culturing mammalian ceils such as CHO cells is between about 30 to 38° C. and a suitable $dO_2$ is between 5-90% of air saturation, in a humidified, controlled atmosphere, such that optimal growth is achieved for the particular cell line. For example, fed batch cell culture conditions may be used because fed batch culture conditions are devised to enhance growth of the mammalian cells in the growth phase of the cell culture. "Fed-batch culture" as used herein refers to a method of culturing cells in which additional components are provided to the culture at a time or times subsequent to the beginning of the culture process. A fed-batch culture is typically stopped at some point and the cells and/or components in the medium are harvested and optionally purified. Further, at a particular stage the cells may be used to inoculate a production phase or step of the cell culture. Alternatively, the production phase or step may be continuous with the inoculation or growth phase or step.

"Transition phase" of the cell culture refers to the period of time during which culture conditions for the production phase are engaged. During the transition phase environmental factors such as temperature of the cell culture, medium osmolality and the like are shifted from growth conditions to production conditions.

"Production phase" of the cell culture refers to the period of time during which cell growth has plateaued. During the production phase, logarithmic cell growth has ended and protein production is primary. During this period of time, the medium is generally supplemented to support continued protein production and to achieve the desired glycoprotein product. For example, the cell culture environment during the production phase of the cell culture is controlled. According to the method of the present invention, one or more factors affecting viable cell density and/or product titer of the mammalian host cell culture are manipulated such that a specific galactosyl content of an expressed recombinant protein is achieved. "Titre" as used herein refers to the total amount of recombinantly expressed glycoprotein produced by a mammalian cell culture in a given amount of medium volume. Titre is typically expressed in units of milligrams of glycoprotein per millilitre of medium. In particular, factors which increase galactosyl content of a recombinant protein are controlled during the production phase of the cell culture process such that the resulting recombinant protein contains the specific galactosyl content. As used herein, the production phase of the cell culture process is preceded by a transition phase of the cell culture which parameters for the production phase of the cell culture are engaged.

In the method of the present invention, the concentration of one or more sulfhydryl compound(s) and/or the concentration of glucose are adjusted in any or all of the growth or production phases of the fermentation process. For example, the concentration of one or more sulfhydryl compound(s) and or glucose may be adjusted at the start of or during the growth phase and/or at the start of or during the production phase. In particular, the concentration of one or more sulfhydryl compound(s) and/or glucose may be adjusted at the start of the growth and at the start of the production phase or at any or all of the start of the growth phase, during the growth phase, at the start of the production phase and during the production phase. In a preferred aspect of the present invention, the one or more sulfhydryl compound(s) and/or glucose are added to the medium at the beginning of or during a production phase to create a concentration of the one or more sulfhydryl compound(s) with about 4 mM to 10 mM, sulfhydryl group(s) in the medium and/or at least more than 3.0 g/L glucose. In another preferred aspect of the present invention, the method further comprises an initial step of cultivating the mammalian cells in the same medium without said one or more sulfhydryl compound(s) containing about 4 mM to 10 mM, sulfhydryl group(s) and/or at least more than 3.0 g/L glucose. In still another aspect of the present invention, the method further comprises an initial step of cultivating the mammalian cells in the same medium without said one or more sulfhydryl compound(s) containing about 4 mM to 10 mM, sulfhydryl group(s) and/or at least more than 3.0 g/L glucose and the one or more sulfhydryl compound(s) and/or glucose are added to the medium at the beginning of or during a production phase to create a concentration of the one or more sulfhydryl compound(s) with about 4 mM to 10 mM, sulfhydryl group(s) in the medium and/or at least more than 3.0 g/L glucose.

Concentration of one or more sulfhydryl compound(s) may be adjusted by increasing or decreasing the concentration of those sulfhydryl compound(s) in the culture medium. In the present invention, when the concentration of those sulfhydryl compound(s) are increased or decreased, this increase or decrease in concentration is relative to the concentration of those sulfhydryl compound(s) in the medium in the culture phase immediately preceding the increase. Thus, if there is an increase in the concentration of, for example, cystine and/or cysteine, in the medium at the start of the production phase, this is an increase in the concentration of those sulfhydryl compound(s) over the concentration of those sulfhydryl compound(s) in the medium of the immediately preceding growth phase. Similarly, if there is to be an increase in the concentration of, for example, cystine and/or cysteine, in the medium during the production phase, this is an increase of the concentration of those sulfhydryl compound(s) over the concentration of those sulfhydryl compound(s) in the medium of the immediately preceding part of the production phase. Similarly, if there is to be a decrease in the concentration of, for example, cystine and/or cysteine, in the medium at the start of or during any of the growth or production phases, this is a decrease in the concentration of those sulfhydryl compound(s) in the medium of the immediately preceding culture phase.

It is generally preferred that when the concentrations of any of the one or more sulfhydryl compound(s) are adjusted in the cell culture medium, the concentrations of all of these one or more sulfhydryl compound(s) are adjusted at the same time. However, the method of the present invention also includes adjustment of one or more sulfhydryl compound(s) by adjusting the first sulfhydryl compound(s) at one time and then the second, or vice versa. In particular, if the concentration of one or more sulfhydryl compound(s) is to increase and the concentration of one or more sulfhydryl compound(s) is to decrease, the adjustment to increase and decrease may take place at the same time or at different times. It is preferred, in that case, that the adjustment to increase the concentration of one or more sulfhydryl compound(s) and to decrease the concentration of one or more sulfhydryl compound(s) takes place at the same point in time or in the same medium.

In the method of the present invention, adjustment of the concentration of one or more sulfhydryl compound(s) can be achieved by any technique appropriate to the fermentation conditions being used. The method by which the concentration of one or more sulfhydryl compound(s) is adjusted is not essential to the present invention and appropriate methods are known in the art. Adjustment of the concentration of one or more sulfhydryl compound(s) can thus take place either by supplementing the medium (in the case of an increase in concentration of one or more sulfhydryl compound(s)) in which the cells are being cultured, or by transferring all or a portion of the cells (e.g., by splitting) to a fresh medium containing the desired concentration of one or more sulfhydryl compound(s). A combination of these methods may be used if required.

Adjustment of the concentration of one or more sulfhydryl compound(s) can therefore be continuous, over the whole or a portion of the culture period, or may be intermittent, for example as a reaction to the assumed, calculated or measured concentration of one or more sulfhydryl compound(s) in the culture medium. The invention defines adjustment of the concentration of one or more sulfhydryl compound(s) within ranges. If actual measurement or calculation of the concentration of each or all of one or more sulfhydryl compound(s) during a defined culture period, for example, during the growth or production phase, indicates that the concentration of each or all of one or more sulfhydryl compound(s) falls within the ranges recited herein, adjustment of that concentration may nonetheless take place, so long as the resulting concentration of one or more sulfhydryl compound(s) remains within the range recited. If required, known techniques can be used to measure the actual concentrations of one or more sulfhydryl compound(s) in the culture medium before the adjustments are made.

Thus, if batch fermentation conditions are being used, achieving an increase in the concentrations of one or more sulfhydryl compound(s) may be by, for example, seeding into a fresh medium containing or supplemented with concentrations of the appropriate one or more sulfhydryl compound(s) that are increased over the existing culture medium, or by splitting the cells into a medium containing or supplemented with the increased concentrations of the appropriate one or more sulfhydryl compound(s) over the existing medium. If fed-batch fermentation conditions are being used, achieving an increase in the concentrations of one or more sulfhydryl compound(s) may be by, for example, seeding into a fresh medium containing or supplemented with the increased concentrations of the appropriate one or more sulfhydryl compound(s), giving one or more bolus or continuous feeds of the appropriate one or more sulfhydryl compound(s) to the culture medium; by determining a feed rate based on cell number or calculated according to known metabolic models, metabolic surrogate markers etc., or by splitting the culture into a medium which contains or has been supplemented with the increased concentrations of the appropriate one or more sulfhydryl compound(s). If bolus or continuous feed is being added, this may contain other nutrients/components required for the culture in addition to one or more sulfhydryl compound(s). If perfusion fermentation conditions are being used, achieving an increase in the concentrations of one or more sulfhydryl compound(s) may be achieved by, for example, a continual or intermittent addition of one or more sulfhydryl compound(s) to the reactor either at the same time or separately to other nutrients/components being added to the perfusion culture.

If a decrease in the concentrations of one or more sulfhydryl compound(s) is required, this may be achieved by seeding the cells into a fresh medium in which the concentrations of one or more sulfhydryl compound(s) is decreased in comparison to the concentration of those one or more sulfhydryl compound(s) in the medium of the immediately preceding culture phase.

The specific values of decreased or increased concentrations of one or more sulfhydryl compound(s) are based either on actual measurements of the one or more sulfhydryl compound(s) in the culture medium or on theoretical concentrations or calculations of the concentration of the one or more sulfhydryl compound(s) in the culture solution surrounding the cells. The practitioner will appreciate that some concentration of the one or more sulfhydryl compound(s), introduced for example via impurities and leaching may be present and will take these into account when calculating a decreased or increased concentration of the one or more sulfhydryl compound(s) in accordance with the invention.

In one aspect in the context of the present invention, the concentration of one or more sulfhydryl compound(s) may be adjusted in the culture medium to increase the galactosylation of glycans of a recombinant protein. In another aspect of the present invention, the concentration of one or more sulfhydryl compound(s) may be adjusted in the culture medium to enhance the viable cell density, to enhance the product titer of the recombinant protein and/or then again to increase the galactosylation of glycans of a recombinant protein. For example, the concentration of one or more sulfhydryl compound(s) may be adjusted in the culture medium first to enhance growth and then again to increase the galactosylation of glycans of a recombinant protein. As another example, the concentration of one or more sulfhydryl compound(s) may be adjusted in the culture medium to enhance the viable cell density and then again to increase the galactosylation of glycans of a recombinant protein. As another example, the concentration of one or more sulfhydryl compound(s) may be adjusted in the culture medium to enhance the product titer of the recombinant protein and then again to increase the galactosylation of glycans of a recombinant protein. In yet another aspect of the present invention, the concentration of one or more sulfhydryl compound(s) may be adjusted in the culture medium to enhance the viable cell density, to enhance the product titer of the recombinant protein and then again to increase the galactosylation of glycans of a recombinant protein.

As used herein, the term "bioreactor" refers to any vessel used for the growth of a prokaryotic or eukaryotic cell culture, e.g., an animal cell culture (such as a mammalian cell culture). The bioreactor can be of any size so long as it is useful for the culturing of cells, e.g., mammalian cells. Typically, the bioreactor will be at least 30 ml and may be 1, 10, 100, 250, 500, 1,000, 2,500, 5,000, 8,000, 10,000, 12,000 liters or more, or any intermediate volume. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of a large-scale cell culture production bioreactor is generally greater than about 100 ml, typically at least about 10 liters, and may be 500, 1,000, 2,500, 5,000, 8,000, 10,000, 12,000 liters or more or any intermediate volume. For example, cultivation of the mammalian cell is in a large-scale format bioreactor, preferably in a 10,000 L bioreactor. One of ordinary skill in the art will be aware of, and will be able to choose, suitable bioreactors for use in practicing the present invention.

As used in a preferred aspect in the context of the present invention, the method further comprises harvesting the recombinant protein produced by the mammalian cell. Harvesting the expressed protein either during or at the end of a culture period, preferably the production phase, can be achieved using methods known in the art. The protein may be harvested from the culture medium as a secreted protein, although it may be harvested from host cell lysates when directly produced without a secretory signal. If the protein is membrane-bound, it can be released from the membrane using a suitable detergent solution (e.g. Triton-X 100) or its extracellular region may be released by enzymatic cleavage. The expressed protein may be isolated and/or purified as necessary using techniques known in the art. An "isolated" protein such as an antibody is one which has been separated from a component of its natural environment. In some aspects, a protein, e.g. an antibody, is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

As used herein, the term "expression" or "expresses" are used interchangeably and refer to transcription and translation within a host cell. The level of expression of a recombinant protein in a host cell may be determined on the basis of either the amount of corresponding mRNA that is present in the cell or the amount of protein encoded by the corresponding gene. For example, mRNA transcribed from a product gene is desirably quantitated by northern hybridization (Sambrook et al. Molecular Cloning A Laboratory Manual (Cold Spring Harbor Laboratory Press. 1989)). Protein encoded by a product gene can be quantitated either by assaying for the biological activity of the protein or by employing assays that are independent of such activity such as western blotting or radioimmunoassay using antibodies that are capable of reacting with the protein (Sambrook et al. Molecular Cloning A Laboratory Manual, pp 18 1-18 88 (Cold Spring Harbor Laboratory Press. 1989)).

In particular, the mammalian cells which express a recombinant protein having monogalactosylated or digalactosylated glycans should express or be manipulated to express the particular enzymes such that under appropriate conditions, as described herein, the appropriate post translational modification occurs in vivo. The enzymes include those enzymes necessary for the addition and completion of N- and O-linked carbohydrates such as those described in Hubbard and Ivan supra for N-linked oligosaccharides. The enzymes optionally include oligosaccharyltransferase, alpha-glucosidase I, alpha-glucosidase II, ER alpha (1.2) mannosidase, Golgi alpha-mannodase I, N-acetylglucosaminyltransferase I, Golgi alpha-mannodase II, N-acetylglucosaminyltransferase II, alpha (1.6) fucosyltransferase and β (1.4) galactosyltranferase. Additionally, the host cell expresses the appropriate enzyme(s) that can be expected to attach the galactose in specific position and linkage as part of the host cell genome. Optionally, the host cell can be made to express the appropriate enzyme(s) by, for instance, transfection of the host cell with the DNA encoding the enzyme(s). The enzyme(s) such as those described above would be expected to add the galactose to the appropriate oligosaccharide structure such as GlcNAc. Appropriate enzyme(s) within the context of the present invention include but are not limited to those enzyme(s) which catalyze the galactosylation and branching of the N- and O-linked oligosaccharides.

For the culture of the mammalian cells expressing the desired protein and capable of adding the desired carbohydrates in specific position and linkage, numerous culture conditions can be used paying particular attention to the host cell being cultured. Suitable culture conditions for mammalian cells are well known in the art (J. Immunol. Methods (1983)56:221-234) or can be easily determined by the person skilled in the art (see, for example, Animal Cell Culture: A Practical Approach 2nd Ed., Rickwood. D. and Hames. B. D., eds. Oxford University Press. New York (1992)) and vary according to the particular host cell selected.

The mammalian cell culture of the present invention is prepared in a medium suitable for the particular cell being cultured. "Medium", "cell culture medium" and "culture medium" are used herein interchangeably and refer to a solution containing nutrients which sustain growth of mammalian cells. Typically, such solutions provide essential and non-essential amino acids, vitamins, energy sources, lipids and trace elements required by the cell for minimal growth and/or survival. Such a solution may also contain supplementary components that enhance growth and/or survival above the minimal rate including, but not limited to, hormones and/or other growth factors, particular ions, such as sodium, chloride, calcium, magnesium and phosphate, buffers, vitamins, nucleosides or nucleotides, trace elements, amino acids, lipids and/or glucose or other energy source. A medium is advantageously formulated to a pH and salt concentration optimal for cell survival and proliferation.

Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace (1979) Meth. Enz., 58:44; Barnes and Sato (1980) Anal. Biochem., 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, may be used as culture media. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art.

As used herein, the term "under conditions in which the cell expresses the recombinant protein" denotes conditions which are used for the cultivation of a cell expressing a polypeptide and which are known to or can be determined by a person skilled in the art. It is known to a person skilled in the art that these conditions may vary depending on the type of cell cultivated and type of recombinant protein expressed. In general, the cell is cultivated at a temperature, e.g. between 20° C. and 40° C., and for a period of time sufficient to allow effective production of the conjugate, e.g. for of from 4 to 28 days, in a volume of 0.01 to 10' liter.

Preferably, the mammalian host cell is a CHO cell, preferably a CHO cell lacking dihydrofolate reductase (DHFR) activity and a suitable medium contains a basal medium component such as a DMEM/HAMF-12 based formulation (for composition of DMEM and HAM F12 media, see culture media formulations in American Type Culture Collection Catalogue of Cell Lines and Hybridomas. Sixth Edition. 1988, pages 346-349) with modified concentrations of some components such as amino acids, salts, sugar, and vitamins, and optionally containing glycine, hypoxanthine, thymidine, recombinant human insulin, hydrolyzed peptone, a cell protective agent, such as Pluronic F68 or the equivalent pluronic polyol, Gentamycin™, and trace elements.

According to the present invention, a mammalian host cell us cultured to produce a recoverable recombinant protein having monogalactosylated or digalactosylated glycans. The overall content of galactose in the recombinant protein is controlled by controlling the cell culture parameters which affect viable cell density, product titer and/or the content of galactose in the mammalian cell. Factors which affect viable cell density and/or product titer are well known in the art and include but are not limited to factors which affect DNA RNA copy number, factors which affect RNA, such as factors which stabilize RNA, media nutrients and other supplements, the concentration of transcription enhancers, the osmolality of the culture environment, the temperature and pH of the cell culture, and the like. According to the present invention adjustment of these factors, alone or in combination, to increase viable cell density and/or product titer generates a recombinant protein having monogalactosylated or digalactosylated glycans. The adjustment of these factors, alone or in combination, to increase viable cell density and/or product titer, generates a recombinant protein with an increased galactose content.

The terms "cell density," "cell concentration," or the like, as used herein, refer to that number, weight, mass, etc. of cells present in a given volume of medium. "Peak cell density" or the like refers to the maximum number of cells that can be reached in a given volume of medium, and "desired peak cell density" or the like refers to the maximum number of cells that a practitioner desires to obtain (e.g., targets) in a given cell volume. Variations of such target value(s) will be clear to those of skill in the art, e.g., one of skill may express a target value(s) in terms of desired cell mass, and such target value(s) may be in one or more appropriate units of measure (e.g., desired peak units of cell mass).

The term "cell viability" as used herein refers to the ability of cells in culture to survive under a given set of culture conditions or experimental variations. The term as used herein also refers to that portion of cells that are alive at a particular time in relation to the total number of cells, living and dead, in the culture at that time.

The terms "culture" and "cell culture" as used herein refer to a cell population that is suspended in a cell culture medium under conditions suitable to survival and/or growth of the cell population. As used herein, these terms may refer to the combination comprising the cell population (e.g., the animal cell culture) and the medium in which the population is suspended. In one aspect, the method further comprises the step of pre-cultivating of the mammalian cells in a cell culture medium. As provided herein, the cells may be pre-cultivated to the exponential growth phase in a suitable cell culture medium with or without sulfhydryl group(s) from one or more sulfhydryl compound(s). As used herein, the term "pre-cultivation" or "pre-cultivating" is used interchangeably and refers to a culturing step prior to the cultivation of the cells in a second cultivation step. For example, the cells may be grown in a first cell culture as a precultivation step and subsequently inoculated in a second cell culture, e.g. in a bioreactor such as a production bioreactor. The person skilled in the art is aware of precultivation steps and knows how to perform such precultivation steps.

The term "integrated viable cell density" or "IVCD" as used herein refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

The recombinant protein of the present invention may be produced by culturing the cells which express the recombinant protein under a variety of cell culture conditions. In other words, biomass generation and protein expression from mammalian cells is achieved according to the method of the invention by culture of the cells under any fermentation cell culture method or system that is amenable to the growth of the cells for biomass generation and expression of proteins may be used with the present invention. For example, the cells may be grown in batch, fed-batch, perfusion or split-batch cultures, where the culture is terminated after sufficient expression of the proteins has occurred, after which the proteins is harvested and, if required, purified.

For example, in the cell culture of the present invention a fed batch culture procedure may be employed. In a fed batch culture, the mammalian cells may be supplied to a culturing vessel initially and additional cell nutrients are fed, continuously or in increments, to the culture during culturing, with or without periodic cell and/or product harvest before termination of culture. A fed-batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by. e.g., filtration, encapsulation, anchoring to microcarriers etc. and the culture medium is continuously or intermittently introduced and removed from the culturing vessel). In the alternative, the cells may be grown in perfusion cultures, where the culture is not terminated and new nutrients and components are added periodically or continuously to the culture and expressed glycoprotein is removed, either periodically or continuously.

Further, the cells of the culture may be propagated according to any scheme or routine that may be suitable for the particular host cell and the particular production plan contemplated. For example, reactors, temperatures and other conditions for fermentation culture of cells for biomass generation and the production of proteins, such as oxygen concentration and pH are known in the art. Any conditions appropriate for culture of the selected mammalian cell can be chosen using information available in the art. The culture conditions, such as temperature, pH and the like, are typically those previously used with the host cell selected for expression and will be apparent to the person skilled in the art. If desired, the temperature and/or the pH and/or $CO_2$ could be altered during cultivation in order to increase yield and/or increase the relative amount of the desired protein quality.

Further in this context, the present invention contemplates a single step or multiple step culture procedure. In a single step culture, the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. "Cell viability" as used herein refers to the ability of cells in culture to survive under a given set of culture conditions or experimental variations. The term as used herein also refers to that portion of cells which are alive at a particular time in relation to the total number of cells, living or dead, in culture at that time. The cells may be maintained in the growth phase for a suitable period of time by the addition of fresh medium to the host cell culture.

For instance, cell culture procedures for the large- or small-scale production of proteins are potentially useful within the context of the present invention. Procedures including, but not limited to, a fluidized bed bioreactor, hollow fiber bioreactor, roller bottle culture, or stirred tank bioreactor may be used and operated alternatively in a batch, fed-batch and/or perfusion mode. "Perfusion culture" as used herein refers to a method of culturing cells comprising growing cells on an inoculation base medium and, when cells achieve a desired cell density replacing the spent medium with a fresh medium. Perfusing may comprise either continuous or intermittent perfusion and may include delivery of at least one bolus feed to the cell culture. A perfusion culture may be followed by a fed-batch culture. As used herein, the term "bioreactor" refers to any vessel used for the growth of a mammalian cell culture. Typically, a bioreactor will be at least 1 litre and may be 10, 100, 250, 500, 1000, 2500, 5000, 8000, 10,000, 12,000 litres or more, or any volume in between. The internal conditions of the bioreactor, including but not limited to pH, dissolved oxygen and temperature, are typically controlled during the culture period. A bioreactor can be composed of any material that is suitable for holding mammalian cell cultures suspended in media under the culture conditions of the present invention, including glass, plastic or metal. In a preferred aspect of the present invention, culturing the mammalian cell is in a bioreactor, more preferably in a large-scale format bioreactor. In a more preferred aspect of the present invention, culturing the mammalian cell is at least in a 10.000 L bioreactor.

The Importance of Antibody Fc-Galactosylation

As shown in FIG. 5, the Asn297-linked carbohydrate chain consists of a common biantennary glycan structure of four N-acetylglucosamine (GlcNAc) and three mannose residues, with variable additions of fucose, galactose, and sialic acid residues. These glycans are often named according to the number of biantennary terminal galactose residues, i.e., G0 (no galactose), G1 (one galactose). G2 (two galactoses) and according to the presence of a core fucose residue, i.e., G0 (no galactose), G1 (one galactose), G2 (two galactoses).

In a preferred aspect as used in the context of the present invention, the recombinant protein is for use as a medicament. Change of IgG galactosylation was first reported in rheumatoid arthritis (Parekh et al., Nature. 316 (1985) 452-457) and later in other autoimmune diseases, such as psoriatic arthritis and ankylosing spondylitis (Martin et al., J Rheumatol 28 (2001) 1531-1536). Increased galactosylation has been seen during pregnancy, and in rheumatoid arthritis patients who experience pregnancy-induced remission (Bondt et al., J. Proteome. Res. 12 (2013) 4522-4531). This suggests that increased galactosylation of antibodies might be functionally more anti-inflammatory (Zauner et al., Mol. Cell Proteomics. 12 (2013) 856-865). Karsten et al. (Nature Medicine 18.9 (2012) 1401-1406) confirmed this anti-inflammatory property by showing in mice that high galactosylation of IgG immune complexes promotes the association of Fcγ RUB and dectin-1, which blocks the pro-inflammatory effector functions of C5aR and CXCR226. In another preferred aspect as used in the context of the present invention, the recombinant protein is for use in the treatment of patients with B-cell proliferative disorders such as non-Hodgkin's lymphoma and chronic lymphocytic leukemia or patients with Parkinson's disease and related disorders.

Another important aspect to consider when looking at the functional impact of terminal galactose is that it provides the basis for the addition of sialic acid, the most distal sugar moiety on the IgG-Fc glycan. Oligosaccharide analysis revealed that the lack of protein galactosylation was the potential cause for the reduction of sialic acid content.

Galactose terminating structures are known to have a substantial effect on the affinity towards the C1q complex and their removal results in decreased complement lysis activity (Hodoniczky, J. et al., Biotechnol. Progr. 21 (2005) 1644-1652). More specifically, Wright and Morrison (1998) (J Immunol. 1998; 160:3393-3402) and Hodoniczky et al. (2005) have found that absence of galactose on the mAb Fc oligosaccharides reduces the affinity between the Fc and the C1q component of the complement, thus reducing CDC activity.

Rituximab (Rituxan® anti-CD20), first approved in 1997, is a chimeric monoclonal antibody produced in CHO cells for treatment of non-Hodgkin lymphoma and other B-cell related diseases. Rituximab is glycosylated in the Fc, and the Fc glycans are highly heterogeneous, mainly due to the variable presence of terminal galactose residues. The effect of the terminal galactose residues of rituximab on CDC activity comes from the involvement of such residues in the binding of rituximab to complement C1q (Hodoniczky et al. 2005).

The presence or absence of galactose on IgG glycans correlates with modified Fc effector function in some but not all (Boyd et al., Mol Immunol. 32 (1995) 1311-1318; Wright and Morrison, J Immunol. 160 (1998) 3393-3402) monoclonal IgG antibodies, suggesting that the effects observed may be, in part, antibody specific. Tsuchiya et al. (1989) found that agalacto IgG had reduced C1q and Fc receptor binding, and Boyd et al. found that agalacto Campath1 (monoclonal anti-CD52) had reduced cell mediated lysis (CML) but intact capacity to trigger ADCC. Thus, as used herein, "effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation; see also e.g., Thomann et al, PLoS One. 2015 Aug. 12; 10(8):e0134949. doi: 10.1371/journal.pone.0134949. eCollection 2015.

The term "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

In certain aspects, if the recombinant protein is an antibody, the Fc domain of the antibody may comprise one or more alterations as compared to the wild-type Fc domain. These Fc domains would nonetheless retain substantially the same characteristics required for therapeutic utility as compared to their wild-type counterpart. For example, certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624, 821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Half-life of an antibody can be dependent on the structure of the Fc region of an antibody, which in turn affects binding efficacy of said Fc region to FcRn, the neonatal receptor.

Thereby, half-life is increased by maintaining the binding of the Fc region to FcRn. Particularly, at a pH of about 6.0, this binding leads to endosomal trafficking of the antibody bound to FcRn away from the lysosomal degradation pathway, recycling it instead to the plasma membrane where IgG is re-released into the blood stream at pH 7.4. Thereby, an increased IgG half-life in blood is achieved by this pathway, which is necessary for extended exposure of the antibody to its target and enhanced potential for therapeutic efficacy; see Saxena, Abhishek; Bai, Bingxin; Hou, Shin-Chen; Jiang, Lianlian; Ying, Tianlei; et al. Methods in molecular biology (Clifton, N.J.) 1827: 399-417. (2018); Spearman, Maureen; Dionne. Ben; Butler, Michael. Cell Engineering, Vol 7: Antibody Expression and Production 7: 251-292. SPRINGER. (2011) specifically incorporated herein by reference. These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551 and the International Publication WO99/51642. See, also, Idusogie et al. J. Immunol. 164: 4178-4184 (2000). The contents of these are specifically incorporated herein by reference.

Other reported effects of galactosylation on IgG molecules include modification of physicochemical properties such as conformation and surface accessibility (Krapp et al., J. Mol. Biol. 325 (2003) 979-89; Mimura et al., Mol. Immunol. 37 (2000) 697-706). Fortunato and Colina (J. Phys. Chem. 118 (2014) 9844-9851) used explicit water atomistic molecular dynamics simulations to study the effects of galactosylation in the Fc domain of immunoglobulin G1. They suggested glycosylation may be used as a route to improve the aggregation resistance of monoclonal antibodies for therapeutic treatments. As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, antibodies of the invention are used to delay development of a disease or to slow the progression of a disease.

From the data now available, it appears that galactose residues in antibodies influence certain IgGs functions and may be necessary to be effectively monitored and controlled during galactosylation of those molecules.

As stated before, antibody galactosylation has been known to depend on the concentration of UDP-galactose that are present in cells, as these sugar molecules act as substrates required for galactosylation. Increase in UDP-galactose content has been found to be associated to higher galactosylation and sialylation of the antibody expressed in CHO cells. Varying UDP-galactose levels in the cells may possibly also have significant implications on other types of glycosylation in other therapeutic proteins.

Modulating UDP-Galactose Concentration for O-Linked Glycosylation

In general, in recombinant proteins as used herein, sugars can be attached either to the amide nitrogen atom in the side chain of asparagine, an N-linkage, or to the oxygen atom in the side chain of serine or threonine, an O-linkage. O-linked glycosylation occurs through the addition of N-acetyl-galactosamine to serine or threonine residues by the enzyme UDP-N-acetyl-D-galactosamine:polypeptide N-acetylgalactosaminyltransferase (EC2.4.1.41), followed by other carbohydrates, such as UDP-galactose. Therefore, intracellular UDP-galactose concentration may influence O-linked glycosylation. Therefore, the new approach described in this invention may be useful to modulate intracellular UDP-galactose level and to further control the galactosylation level in final protein product.

Modulating UDP-Galactose Concentration for Antibody Fab Glycosylation

The existence of IgG Fab glycans has been known for quite some time. Fab glycans are presumably more accessible for glycosyltransferases, resulting in more processing compared with Fc glycans that are spatially localized at the inner face of the CH2 domains. Accordingly, the intracellular UDP-galactose concentration may also influence IgG Fab galactosylation process. Therefore, the new approach described in this invention may be used to modulate intracellular UDP-galactose level and to further control the galactosylation level in final protein product.

As used in the context of the present invention, the level of the N-linked galactosylated glycans of the recombinant protein is increased. Thus, the method of the present invention increases the production of N-linked galactosylated glycans of a recombinant protein. In one preferred aspect of the present invention, the recombinant protein comprises at least monogalactosylated, more preferably digalactosylated glycans, and wherein the galactosylated glycans are associated with N-acetylglucosamine. The linkages of galactose to their respective target within the recombinant protein and their effect on function of the recombinant protein are further outlined by example as follows.

The present invention also relates to a pharmaceutical composition comprising the recombinant protein. The terms "composition" and "pharmaceutical composition" are used interchangeably and are to be understood as defining pharmaceutical compositions of which the individual components or ingredients are themselves pharmaceutically acceptable, e.g. where oral administration is foreseen, acceptable for oral use and, where topical administration is foreseen, topically acceptable and also includes combinations thereof, i.e. where oral and topical administration is foreseen, acceptable for oral and topical use. The term also refers to a preparation which is in such form as to permit the biological activity of an active ingredient contained therein to be effective, and which contains no additional components which are unacceptably toxic to a subject to which the pharmaceutical composition would be administered. A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations. The skilled person knows that the effective amount of pharmaceutical composition administered to an individual will, inter alia, depend on the nature of the compound. In this context, an "effective amount" of an agent. e.g., a pharmaceutical composition, refers to an amount effective, at dosages and for periods of time necessary, to achieve the desired therapeutic or prophylactic result.

A therapeutic protein such as an antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the pharmaceutical composition, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician.

As used herein, the term "and/or" is to be taken as specific disclosure of each of the two specified features or components with or without the other. For example, "A and/or B" is to be taken as specific disclosure of each of (i) A, (ii) B and (iii) A and B, just as if each is set out individually herein.

Various aspects and features of the invention described herein are described further by way of example below. Although the foregoing invention has been described in some detail by way of illustration and example for purposes of clarity of understanding, the descriptions and examples should not be construed as limiting the scope of the invention.

All patent and non-patent references cited herein are hereby incorporated by reference in their entirety.

EXAMPLES

The cDNAs of uridine diphosphate (UDP) α-D-glucose epimerase (UDP_Glc-E, EC 5.1.3.2) and UDP-α-D-glucose: α-D-galactose-1-phosphate uridylyltransferase from CHO K1M cell line have been cloned and sequenced, respectively. These two enzymes are found to play a crucial role within the UDP-glucose and UDP-galactose conversion pathway in CHO cells.

Example 1: Uridine Diphosphate Glucose Epimerase (UDP-Glc-E) cDNA Amplification and Sequence Analysis in CHO K1M Cell-Line The enzyme uridine diphosphate (UDP)-glucose 4-epimerase (UDP_Glc-E, EC 5.1.3.2), also known as UDP-galactose 4-epimerase, is a homodimeric epimerase found in bacterial, fungal, plant, and mammalian cells. This enzyme catalyzes the reversible conversion of UDP-glucose to UDP-galactose.

Total cellular RNA extraction from CHO K1M cell-line (WO2009047007) was performed by using MagNA Pure LC RNA Isolation Kit-High Performance from Roche (Product No. 03542394001) running on Roche MagNA Pure LC 2.0 Instrument (Product No. 05197686001, Roche Diagnostics GmbH). The concentration of purified RNA was measured by NanoVue (GE Healthcare Bio-Science AB) and stored at −70° C.

This purified cellular RNA was used for UDP_Glc-E cDNA synthesis and targeted amplification. The cDNA synthesis and amplification was performed by using Roche Transcriptor One-Step RT-PCR Kit (Product No. 04655877001, Roche Diagnostics GmbH) with two UDP_Glc-E specific primers homologously designed according to the NCBI GenBank database.

The two primers used here are:

```
forward primer UDP_GlcE-F2-21
(SEQ ID NO.: 5):
5' ATGGCCGAGAAGGTGCTGGTC 3',
and reverse primer UDP_GlcE-R21
(SEQ ID NO.: 6):
5' TTAGGCCTGTGCTCCAAAGCC 3'.
```

RT-PCR Condition:
Reverse transcription: 50° C. 30 min
Initial denaturation: 94° C. 7 min
Amplification PCR:
Denaturation: 94° C. 10 sec
Annealing: 56° C. 30 sec
Elongation: 68° C. 60 sec (60 sec/kb)
Cycle: 10
Denaturation: 94° C. 10 sec
Annealing: 56° C. 30 sec
Elongation: 68° C. 1:30+5 sec (+5 sec/kb)
Cycle: 25
Final elongation: 68° C. 7 min The amplified PCR product was first purified with Roche High Pure PCR Product Purification Kit (Product No. 11732668001, Roche Diagnostics GmbH), and then subjected to direct sequencing analysis. The sequence of UDP_Glc-E cDNA is shown in SEQUENCE-1 (SEQ ID NO.: 1). This cDNA encodes a predicted 348-amino acid protein. The derived amino acid sequence of UDP-glucose 4-epimerase in CHO K1M is shown in SEQUENCE-2 (SEQ ID NO.: 2).

The protein sequence encoded by UDP-Glc-E CHO K1M is 94.5% identical and 96.6% similar to human UDP-glucose 4-epimerase and is closely related to other UDP-glucose 4-epimerases from bovine and mouse.

Example 2: UDP-α-D-Glucose:α-D-Galactose-1-Phosphate Uridylyltransferase (UDP-Gal-T) cDNA Amplification and Sequence Analysis in CHO K1M Cell-Line UDP-α-D-glucose:α-D-galactose-1-phosphate uridylyltransferase (UDP-Gal-T, EC2.7.7.12) catalyzes the nucleotide exchange between uridine 5'-diphosphate glucose (UDP-Glucose) and galactose-1-phosphate (Gal-1-P) to produce uridine 5'-diphosphate galactose (UDP-Galactose) and glucose-1-phosphate (Glc-1-P) through reversible mechanism.

Total cellular RNA extraction from CHO K1M cell-line was performed by using MagNA Pure LC RNA Isolation Kit-High Performance from Roche (Product No. 03542394001) running on Roche MagNA Pure LC 2.0 Instrument (Product No. 05197686001, Roche Diagnostics GmbH). The concentration of purified RNA was measured by NanoVue (GE Healthcare Bio-Science AB) and stored at −70° C.

This purified cellular RNA was used for UDP-Gal-T cDNA synthesis and targeted amplification. The cDNA synthesis and amplification was performed by using Roche Transcriptor One-Step RT-PCR Kit (Product No. 04655877001, Roche Diagnostics GmbH) with two UDP-Gal-T specific primers homologously designed according to the NCBI GenBank database.

The two primers used here are:

```
forward primer UDP-Gal-T-F2-21 (SEQ ID NO.: 7):
5' ATGTCGCAAAACGGAGATGAT 3',
and reverse primer UDP-Gal-T-R18 (SEQ ID NO.: 8):
5' TCAAGCAACAGCTGCTGT 3'.
```

RT-PCR Condition:
Reverse transcription: 50° C. 30 min
Initial denaturation: 94° C. 7 min
Amplification PCR:
Denaturation: 94° C. 10 sec
Annealing: 56° C. 30 sec
Elongation: 68° C. 60 sec (60 sec/kb)
Cycle: 10
Denaturation: 94° C. 10 sec
Annealing: 56° C. 30 sec
Elongation: 68° C. 1:30+5 sec (+5 sec/kb)
Cycle: 25
Final elongation: 68° C. 7 min The amplified PCR product was first purified with Roche High Pure PCR Product Purification Kit (Product No. 11732668001, Roche Diagnostics GmbH), and then subjected to direct sequencing analysis. The sequence of UDP-Gal-T cDNA is shown in SEQUENCE-3 (SEQ ID NO.: 3). This cDNA encodes a predicted 379-amino acid protein. The derived amino acid sequence of UDP-α-D-glucose:α-D-galactose-1-phosphate uridylyltransferase in CHO K1M is shown in SEQUENCE-4 (SEQ ID NO.: 4).

The protein sequence encoded by UDP-Gal-T CHO K1M is 89.4% identical and 94.7% similar to human UDP-α-D-glucose:α-D-galactose-1-phosphate uridylyltransferase and is closely related to other UDP-α-D-glucose:α-D-galactose-1-phosphate uridylyltransferase from mouse and bovine.

Example 3: Enzyme and Pathway Modulation with L-Cysteine in CHO Cell Line L965 for a Recombinant Anti-Human α-Synuclein Antibody Production In this example CHO K1M, a cell-line derived from Chinese Hamster Ovary (CHO) cells, was used as the host cell-line (WO2009047007).

The CHO K1M cells were engineered to express an anti-human α-synuclein monoclonal antibody (described in U.S. Pat. Nos. 9,670,274B2, and 9,890,209B9), which binds to monomeric or oligomeric human α-synuclein, here designated as CHO L965 cell-line.

Human α-synuclein can form fibrillar aggregates, and these aggregates are the main component of Lewy bodies and Lewy neurites. Recent scientific work suggests that prefibrillar oligomers of alpha-synuclein may be key contributors in the progression of Parkinson's disease (Luk et al., 2012).

The specific antibody L965 can bind extracellular α-synuclein specifically and may be used to prevent cell-to-cell aggregate transmission and the progression of Parkinson's disease.

For cell culture process, a custom-ordered version of serum-free, chemically-defined medium used as the basal medium to culture the L965 cells. After thawing, the cells were passaged in this medium in the presence of 3 μg/mL blasticidin (Blasticidin, InvivoGen S.A.S., France) and 10 μg/mL puromycin (Puromycin-Solution, InvivoGen S.A.S., France, Cat. No. ANT-PR) in shake flasks on a 3-4 day schedule. Passage conditions were 36.5° C., 7% C02, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined was used as the basal medium to propagate the L965 cells.

During this production medium preparation, additional glucose, glutamine, amino acids, trace elements (RTE1.2 Solution, Gibco, UK; Ref. No. 043-90585H), and salts were also included.

In this case, the final concentration of L-cysteine (Merck Chemicals GmbH, Cat. No.: 1.02735.1000) in medium was adjusted to 6 mM and 10 mM, respectively.

The pre-cultured cells were used to inoculate the N-2 step at about $3.0 \times 10^5$ cells/mL and the N-1 step at about $5.0 \times 10^5$ cells/mL parallel with the prepared production media containing 6 mM or 10 mM L-cysteine, respectively, all without blasticidin and puromycin. Production bioreactors were inoculated at about $10.0 \times 10^5$ cells/mL in the medium containing 6 mM or 10 mM L-cysteine, respectively. The cells were cultured in production bioreactors under fed-batch culture conditions with predefined pH, dissolved oxygen, temperature and nutrient feeding strategy. Usually 2 L bioreactors with an initial culture volume of 1.2 L were employed, unless otherwise noted.

The temperature in the bioreactors was controlled at 36.5° C., and the stirrer speed was set to be about 223 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of the in-house medium with glucose, glutamine, amino acids, and salts. This feed medium was prepared in solution and was added to the culture on Day-3, Day-6 and Day-9, each at an amount of about 10 volume % of the working culture volume.

An additional glucose feed solution was prepared and added to the culture during Day 4-14 to maintain glucose concentration at about ≥4 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz, Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

FIGS. 6A-6E illustrate the effects of different L-cysteine concentrations on G0 form of anti-α-synuclein antibody L965, G1 form of anti α-synuclein antibody L965, G2 form of anti α-synuclein antibody L965, product titer and cell growth (IVCD).

FIG. 6A shows that at the end of the 14-day production process, G0 form of anti-α-synuclein antibody L965 from the process with 6 mM L-cysteine in production medium was about 10.4% lower than for the process with 10 mM L-cysteine in production medium.

FIG. 6B shows that at the end of the 14-day production process, G1 form of anti α-synuclein antibody L965 from the process with 6 mM L-cysteine in production medium was about 13% higher than for the process with 10 mM L-cysteine in production medium.

FIG. 6C shows that at the end of the 14-day production process, G2 form of anti α-synuclein antibody L965 from the process with 6 mM L-cysteine in production medium was about 5% higher than for the process with 10 mM L-cysteine in production medium.

FIG. 6D shows that at the end of the 14-day production process, product titer in the process with 6 mM L-cysteine in production medium was about 73% higher than for the process with 10 mM L-cysteine in production medium.

FIG. 6E shows that at the end of the 14-day production process, cell growth in the process with 6 mM L-cysteine in production medium was higher than for the process with 10 mM L-cysteine in production medium.

Example-4: Enzyme and Pathway Modulation with L-Cysteine in CHO Cell-Line T104 for a Recombinant Anti-CD20/Anti-CD3 Bispecific Antibody Production In this example CHO K1M, a cell-line derived from Chinese Hamster Ovary (CHO) cells, was used as the host cell-line (WO2009047007). The CHO K1M cells were engineered to express a CD20-CD3 targeting T-cell bispecific monoclonal antibody, anti-CD20/anti-CD3 bsAB (described in EP3252078A1), here designated as CHO T104 cell-line.

Anti-CD20/anti-CD3 bsAB is a T cell bispecific (TCB) antibody targeting CD20 expressed on B cells and CD3 epsilon chain (CD3ε) present on T cells. The mechanism of action of anti-CD20/anti-CD3 bsAB comprises simultaneous binding to CD20+ B cells and CD3+ T cells, leading to T-cell activation and T-cell mediated killing of B cells. In the presence of CD20+ B cells, whether circulating or tissue resident, pharmacologically active doses will trigger T-cell activation and associated cytokine release. Anti-CD20/anti-CD3 bsAB may be used for treating a disease, particularly a B-cell proliferative disorder, and for reduction of adverse effects in response to the administration of a T-cell activating therapeutic agent. For example, patients with chronic lymphocytic leukemia may be treated with anti-CD20/anti-CD3 bispecific antibody.

For cell culture process, a custom-ordered version of serum-free, chemically-defined medium was used as basal medium to culture the T104 cells. After thawing, the cells were passaged in this medium in the presence of 250 nM methotrexate (MTX; Pfizer, Cat. No. 13999031) in shake flasks on a 3-4 day schedule. Passage conditions were 36.5 CC. 7% $CO_2$, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined medium was used as the basal medium to propagate the T104 cells. During this production medium preparation, additional glucose, glutamine, amino acids, trace elements (RTE1.0 Solution, SAFC, Ref. No. CR40054-1000M SLBR5143V), and salts were also included. In this case, the final concentration of L-cysteine (Merck Chemicals GmbH, Cat. No.: 1.02735.1000) in medium was adjusted to 5 mM and 10 mM, respectively.

The pre-cultured cells were used to inoculate the N-2 step at about $3.0 \times 10^5$ cells/mL and the N-1 step at about $5.0 \times 10^5$ cells/mL parallel with the prepared production media containing 5 mM or 10 mM L-cysteine, respectively, all without MTX. Production bioreactors were inoculated at about $10.0 \times 10^5$ cells/mL in the medium containing 5 mM or 10 mM L-cysteine, respectively. The cells were cultured in production bioreactors under fed-batch culture conditions with predefined pH, dissolved oxygen, temperature and nutrient feeding strategy. Usually 2 L bioreactors with an initial culture volume of 1.2 L were employed, unless otherwise noted. Ambr-250 bioreactors with an initial culture volume of 200 mL were employed.

The temperature in the bioreactors was controlled at 36.5° C., and the stirrer speed was set to be about 223 rpm. A gas mixture containing air, $CO_2$, and O2 was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of the in-house medium with glucose, glutamine, amino acids, and salts. This feed medium was prepared in solution and was added to the culture on Day-3, Day-6 and Day-9, each at an amount of about 10 volume % of the working culture volume.

An additional glucose feed solution was prepared and added to the culture during Day 4-14 to maintain glucose concentration at about ≥3 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz. Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

FIGS. 7A-7D illustrate the effects of different L-cysteine concentrations on G0 form of anti-CD20/anti-CD3 bsAB, G1 form of anti-CD20/anti-CD3 bsAB, cell growth (IVCD), and product titer.

FIG. 7A shows that at the end of the 14-day production process, G0 form of anti-CD20/anti-CD3 bsAB from the process with 5 mM L-cysteine in production medium was about 5.5% lower than for the process with 10 mM L-cysteine in production medium.

FIG. 7B shows that at the end of the 14-day production process, G1 form of anti-CD20/anti-CD3 bsAB from the process with 5 mM L-cysteine in production medium was about 3.4% higher than for the process with 10 mM L-cysteine in production medium.

FIG. 7C shows that at the end of the 14-day production process, product titer in the process with 5 mM L-cysteine in production medium was about 66% higher than for the process with 10 mM L-cysteine in production medium.

FIG. 7D shows that at the end of the 14-day production process, cell growth in the process with 5 mM L-cysteine in production medium was higher than for the process with 10 mM L-cysteine in production medium.

Example-5: Enzyme and Pathway Modulation with L-Cysteine in a Recombinant Anti-CD20/Anti-CD3 Bispecific Antibody Producing CHO Cell Line T104 for Improved Production Process In this example CHO K1M, a cell-line derived from Chinese Hamster Ovary (CHO) cells, was used as the host cell-line (WO2009047007). The CHO K1M cells were engineered to express an anti-CD20/anti-CD3 targeting T cell bispecific monoclonal antibody, anti-CD20/anti-CD3 bsAB (described in EP3252078A1), here designated as T104 cell-line.

Anti-CD20/anti-CD3 bsAB is a T cell bispecific (TCB) antibody targeting CD20 expressed on B cells and CD3 epsilon chain (CD3E) present on T cells. The mechanism of action of anti-CD20/anti-CD3 bsAB comprises simultaneous binding to CD20+ B cells and CD3+ T cells, leading to T-cell activation and T-cell mediated killing of B cells. In the presence of CD20+ B cells, whether circulating or tissue resident, pharmacologically active doses will trigger T-cell activation and associated cytokine release. Anti-CD20/anti-CD3 bsAB may be used for treating a disease, particularly a B-cell proliferative disorder, and for reduction of adverse effects in response to the administration of a T-cell activating therapeutic agent.

For cell culture process, a custom-ordered version of serum-free, chemically-defined in house medium was used as basal medium to culture the T104 cells. After thawing, the cells were passaged in this medium in the presence of 250 nM methotrexate (MTX; Pfizer, Cat. No. 13999031) in shake flasks on a 3-4 day schedule. Passage conditions were 36.5° C., 7% $CO_2$, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined medium was used as the basal medium to propagate the T104 cells. During this production medium preparation, additional glucose, glutamine, amino acids, trace elements (RTE1.2 Solution, Gibco, UK; Ref. No. 043-90585H), and salts were also included. In this case, the final concentration of L-cysteine (Merck Chemicals GmbH, Cat. No.: 1.02735.1000) in medium was adjusted to 5 mM and 10 mM, respectively.

The pre-cultured cells were used to inoculate the N-2 step at about $3.0 \times 10^5$ cells/mL and the N-1 step at about $5.0 \times 10^5$ cells/mL parallel with the prepared production media containing 5 mM or 10 mM L-cysteine, respectively, all without MTX. Production bioreactors were inoculated at about $10.0 \times 10^5$ cells/mL in the medium containing 5 mM or 10 mM L-cysteine, respectively. The cells were cultured in production bioreactors under fed-batch culture conditions with predefined pH, dissolved oxygen, temperature and nutrient feeding strategy. 2 L bioreactors with an initial culture volume of 1.2 L were employed, unless otherwise noted. Ambr-250 bioreactors with an initial culture volume of 200 mL were employed, unless otherwise noted.

The temperature in the bioreactors was controlled at 36.5° C., and the stirrer speed was set to be about 223 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of RF1.0 Powder (SAFC, Cat. No. CR60112), glucose, glutamine, amino acids, and salts. This feed medium was prepared in solution and was added to the culture on Day-3, and Day-6 and Day-9, each at an amount of about 10 volume % of the working culture volume.

An additional glucose feed solution was prepared and added to the culture during Day 4-14 to maintain glucose concentration at about ≥3 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz, Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

FIGS. 8A-8D illustrate the effects of different L-cysteine concentrations on G0 form of anti-CD20/anti-CD3 bsAB. G1 form of anti-CD20/anti-CD3 bsAB, cell growth (IVCD), and product titer.

FIG. 8A shows that at the end of the 14-day production process, G0 form of anti-CD20/anti-CD3 bsAB from the process with 5 mM L-cysteine in production medium was about 3.8% lower than for the process with 10 mM L-cysteine in production medium.

FIG. 8B shows that at the end of the 14-day production process. G1 form of anti-CD20/anti-CD3 bsAB from the process with 5 mM L-cysteine in production medium was about 2.5% higher than for the process with 10 mM L-cysteine in production medium.

FIG. 8C shows that at the end of the 14-day production process, product titer in the process with 5 mM L-cysteine in production medium was about 67% higher than for the process with 10 mM L-cysteine in production medium.

FIG. 8D shows that at the end of the 14-day production process, cell growth in the process with 5 mM L-cysteine in production medium was higher than for the process with 10 mM L-cysteine in production medium.

Example 6: Pathway Modulation with L-Cystine in CHO Cell Line L967 for a Recombinant Anti-Human α-Synuclein Antibody Production In this example CHO K1M, a cell-line derived from Chinese Hamster Ovary (CHO) cells, was used as the host cell-line (WO2009047007). The CHO K1M cells were engineered to express an anti-human α-synuclein monoclonal antibody (described in U.S. Pat. No. 9,670,274B2, and US9890209B9), which binds to monomeric or oligomeric human α-synuclein, here designated as L967 cell-line.

Human α-synuclein can form fibrillar aggregates, and these aggregates are the main component of Lewy bodies and Lewy neurites. Recent scientific work suggests that prefibrillar oligomers of alpha-synuclein may be key contributors in the progression of Parkinson's disease (Luk et al., 2012). The specific antibody L967 can bind extracellular α-synuclein by specific and may be used to prevent cell-to-cell aggregate transmission and the progression of Parkinson's disease.

For cell culture process, a custom-ordered version of serum-free, chemically-defined medium was used as the basal medium to culture the L967 cells. After thawing, the cells were passaged in this medium in the presence of 5 µg/mL puromycin (Puromycin-Solution, InvivoGen S.A.S., France, Cat. No. ANT-PR) in shake flasks on a 3-4 day schedule. Passage conditions were 36.5° C., 7% $CO_2$, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined medium was used as the basal medium to propagate the L967 cells. During this production medium preparation, additional glucose, glutamine, amino acids, trace elements (diluted RTE1.2 Solution, Gibco, UK; Ref. No. 043-90585H), and salts were also included. Prior to use, the final concentration of L-cystine (L-cystine disodium salt monohydrate; SAFC, Supplier Item No. RES1523C-A154X) in medium was adjusted to 2 mM and 4 mM, respectively.

The pre-cultured cells were used to inoculate the N-2 step at about $3.0 \times 10^5$ cells/mL and the N-1 step at about $5.0 \times 10^5$ cells/mL parallel with the prepared production media containing 2 mM or 4 mM L-cystine, respectively. Production bioreactors were inoculated at about $10.0 \times 10^5$ cells/mL in the medium containing 2 mM or 4 mM L-cystine, respectively. The cells were cultured in production bioreactors under fed-batch culture conditions with predefined pH, dissolved oxygen, temperature and nutrient feeding strategy. Usually 2 L bioreactors with an initial culture volume of 1.2 L were employed, unless otherwise noted. Ambr-250 bioreactors with an initial culture volume of 200 mL were employed.

The temperature in the bioreactors was controlled at 36.5° C., and the stirrer speed was set to be about 223 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of RF1.0 Powder (SAFC, Cat. No. CR60112), glucose, glutamine, amino acids, and salts. This feed medium was prepared in solution and was added to the culture on Day-3, Day-6 and Day-9, each at an amount of about 10 volume % of the working culture volume.

An additional glucose feed solution was prepared and added to the culture during Day 4-14 to maintain glucose concentration at about ≥4 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz. Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

FIGS. 9A-9E illustrate the effects of different L-cystine concentrations on G0 form of anti α-synuclein antibody L967, G1 form of anti α-synuclein antibody L967, G2 form of anti α-synuclein antibody L967, product titer, and cell growth (IVCD).

FIG. 9A shows that at the end of the 14-day production process, G0 form of anti α-synuclein antibody L967 from the process with 2 mM L-cystine in production medium was about 6.6% higher than for the process with 4 mM L-cystine in production medium.

FIG. 9B shows that at the end of the 14-day production process, G1 form of anti α-synuclein antibody L967 from the process with 2 mM L-cystine in production medium was about 5.9% lower than for the process with 4 mM L-cystine in production medium.

FIG. 9C shows that at the end of the 14-day production process, G2 form of anti α-synuclein antibody L967 from the process with 2 mM L-cystine in production medium was about 1.6% lower than for the process with 4 mM L-cystine in production medium.

FIG. 9D shows that at the end of the 14-day production process, product titer in the process with 2 mM L-cystine in production medium was about 9% lower than for the process with 4 mM L-cystine in production medium.

FIG. 9E shows that at the end of the 14-day production process, cell growth in the process with 2 mM L-cystine in production medium was about 3.7% lower than for the process with 4 mM L-cystine in production medium.

Example 7: Pathway Modulation with L-Cystine in CHO Cell Line L971 for a Recombinant Anti-Human α-Synuclein Antibody Production In this example CHO K1M, a cell-line derived from Chinese Hamster Ovary (CHO) cells, was used as the host cell-line (WO2009047007). The CHO K1M cells were engineered to express an anti-human α-synuclein monoclonal antibody (described in U.S. Pat. No. 9,670,274B2, and US9890209B9), which binds to monomeric or oligomeric human α-synuclein, here designated as CHO L971 cell-line.

Human α-synuclein can form fibrillar aggregates, and these aggregates are the main component of Lewy bodies and Lewy neurites. Recent scientific work suggests that prefibrillar oligomers of alpha-synuclein may be key contributors in the progression of Parkinson's disease (Luk et al., 2012). The specific antibody L971 can bind extracellular α-synuclein by specific and may be used to prevent cell-to-cell aggregate transmission and the progression of Parkinson's disease.

For cell culture process, a custom-ordered version of serum-free, chemically-medium was used as the basal medium to culture the L971 cells. After thawing, the cells were passaged in this medium in the presence of 5 µg/mL puromycin (Puromycin-Solution, InvivoGen S.A.S., France, Cat. No. ANT-PR) in shake flasks on a 3-4 day schedule. Passage conditions were 36.5° C., 7% $CO_2$, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined medium was used as the basal medium to propagate the L971 cells. During this production medium preparation, additional glucose, glutamine, amino acids, trace elements (RTE1.2 Solution, Gibco, UK; Ref. No. 043-90585H), and salts were also included. Prior to use, the final concentration of L-cystine (L-cystine disodium salt monohydrate: SAFC, Supplier Item No. RES1523C-A154X) in medium was adjusted to 2 mM and 4 mM, respectively.

The pre-cultured cells were used to inoculate the N-2 step at about $3.0 \times 10^5$ cells/mL and the N-1 step at about $5.0 \times 10^5$ cells/mL parallel with the prepared production media containing 2 mM or 4 mM L-cystine, respectively. Production bioreactors were inoculated at about $10.0 \times 10^5$ cells/mL in the medium containing 2 mM or 4 mM L-cystine, respectively. The cells were cultured in production bioreactors under fed-batch culture conditions with predefined pH, dissolved oxygen, temperature and nutrient feeding strategy. Usually 2 L bioreactors with an initial culture volume of 1.2 L were employed, unless otherwise noted. Ambr-250 bioreactors with an initial culture volume of 200 mL were employed.

The temperature in the bioreactors was controlled at 36.5° C., and the stirrer speed was set to be about 223 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of RF1.0 Powder (SAFC, Cat. No. CR60112), glucose, glutamine, amino acids, and salts. This feed medium was prepared in solution and was added to the culture on Day-3, Day-6 and Day-9, each at an amount of about 10 volume % of the working culture volume.

An additional glucose feed solution was prepared and added to the culture during Day 4-14 to maintain glucose concentration at about ≥4 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz, Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

FIGS. 10A-10E illustrate the effects of different L-cystine concentrations on G0 form of anti-α-synuclein antibody L971, G1 form of anti-α-synuclein antibody L971, G2 form of anti-α-synuclein antibody L971, product titer, and cell growth (IVCD).

FIG. 10A shows that at the end of the 14-day production process, G0 form of anti-α-synuclein antibody L971 from the process with 2 mM L-cystine in production medium was about 3% higher than for the process with 4 mM L-cystine in production medium.

FIG. 10B shows that at the end of the 14-day production process, G1 form of anti-α-synuclein antibody L971 from the process with 2 mM L-cystine in production medium was about 2% lower than for the process with 4 mM L-cystine in production medium.

FIG. 10C shows that at the end of the 14-day production process, G2 form of anti-α-synuclein antibody L971 from the process with 2 mM L-cystine in production medium was comparable to that from the process with 4 mM L-cystine in production medium.

FIG. 10D shows that at the end of the 14-day production process, product titer in the process with 2 mM L-cystine in production medium was about 30% lower than for the process with 4 mM L-cystine in production medium.

FIG. 10E shows that at the end of the 14-day production process, cell growth in the process with 2 mM L-cystine in production medium was marginally comparable to the process with 4 mM L-cystine in production medium.

Example 8: Functional Comparison of the Recombinant Anti-Human α-Synuclein Antibody L971 Produced from Processes with L-Cysteine or L-Cystine In this example CHO K1M, a cell-line derived from Chinese Hamster Ovary (CHO) cells, was used as the host cell-line (WO2009047007). The CHO K1M cells were engineered to express an anti-human α-synuclein monoclonal antibody (described in US %70274B2, and US9890209B9), which binds to monomeric or oligomeric human α-synuclein, here designated as CHO L971 cell-line.

Human α-synuclein can form fibrillar aggregates, and these aggregates are the main component of Lewy bodies and Lewy neurites. Recent scientific work suggests that prefibrillar oligomers of alpha-synuclein may be key contributors in the progression of Parkinson's disease (Luk et al., 2012). The specific antibody L971 can bind extracellular α-synuclein by specific and may be used to prevent cell-to-cell aggregate transmission and the progression of Parkinson's disease.

For cell culture process, a custom-ordered version of serum-free, chemically-medium was used as the basal medium to culture the L965 cells. After thawing, the cells were passaged in this medium in the presence of 5 μg/mL puromycin (Puromycin-Solution, InvivoGen S.A.S., France, Cat. No. ANT-PR) in shake flasks on a 3-4 day schedule. Passage conditions were 36.5° C., 7% $CO_2$, and 160 rpm for 125 mL and 500 mL flasks using Kuhner Shaker X platform (Adolf Kühner AG, Birsfelden, Basel, Switzerland).

For the inoculation train and production process, another custom-ordered version of serum-free, chemically-defined medium was used as the basal medium to propagate the L971 cells.

During this production medium preparation, additional glucose, glutamine, amino acids, trace elements (RTE1.2 Solution, Gibco, UK; Ref. No. 043-90585H), and salts were also included. Prior to use, the final concentration of L-cystine (L-cystine disodium salt monohydrate; SAFC, Supplier Item No. RES1523C-A154X) in medium was adjusted to 3 mM in one part of the medium. For direct comparison, the final concentration of L-cysteine (Merck Chemicals GmbH, Cat. No.: 1.02735.1000) in medium was adjusted to 6 mM in the other part of the medium.

The pre-cultured cells were used to inoculate the N-2 step at about $3.0×10^5$ cells/mL and the N-1 step at about $5.0×10^5$ cells/mL parallel with the prepared production media containing predefined amount of L-cystine or L-cysteine, respectively. Production bioreactors were inoculated at about $10.0×10^5$ cells/mL in the medium containing predefined amount of L-cystine (3 mM) or L-cysteine (6 mM), respectively. The cells were cultured in production bioreactors under fed-batch culture conditions with predefined pH, dissolved oxygen, temperature and nutrient feeding strategy. Usually 2 L bioreactors with an initial culture volume of 1.2 L were employed, unless otherwise noted. Ambr-250 bioreactors with an initial culture volume of 200 mL were employed.

The temperature in the bioreactors was controlled at 36.5° C., and the stirrer speed was set to be about 223 rpm. A gas mixture containing air, $CO_2$, and $O_2$ was provided. The dissolved carbon dioxide concentration ($dCO_2$) was measured off-line once a day. The dissolved oxygen concentration (DO) was controlled on-line and adjusted to 35% by varying the oxygen partial pressure in the gas mixture. The pH was maintained a pH set-point of 7.00 with a dead-band of ±0.03 pH units by the addition of $CO_2$ or 1.0 M $NaHCO_3$, unless otherwise noted.

The feed medium included a combination of in-house medium with glucose, glutamine, amino acids, and salts. This Feed medium was prepared in solution and was added to the culture on Day-3, Day-6 and Day-9, each at an amount of about 10 volume % of the working culture volume.

An additional glucose feed solution was prepared and added to the culture during Day 4-14 to maintain glucose concentration at about ≥4 g/l.

Samples of production cell culture were taken daily with a syringe for off-line analysis. Production duration typically lasted about 14 days. Cell concentration and viability was measured by the trypan blue exclusion method using a CEDEX instrument (Roche Diagnostics GmbH, Germany). Off-line measurements were performed with a COBAS INTEGRA® 400 plus (Roche Diagnostics GmbH, Germany) for glucose, glutamine, glutamate, lactate, ammonium, and product concentration. Dissolved carbon dioxide was analyzed with a Cobas b221 analyzer (Roche Diagnostics Ltd. CH-6343 Rotkreuz, Switzerland). Osmolality was measured by freezing point depression on an Osmomat Auto Osmometer (Gonotec GmbH, Berlin, Germany).

At the end of main culture production process, cell culture fluid was collected through centrifugation. The supernatants were further subjected to small-scale mAb purification with Protein-A. Glycosylation pattern of the purified mAb was analyzed with 2AB.

The neonatal Fe receptor (FcRn) influences the pharmacokinetic (PK) profile of IgG-type antibodies by its ability to salvage antibodies from the early endosome and recycle them back into circulation. The interaction with FcRn is considered to be the most critical factor in determining the PK of IgG-type therapeutic antibodies and is considered a surrogate for clearance (see review Nimmerjahn and Ravetch 2008).

Fcγ-receptors are mediators of effector functions on immune effector cells. Among the different human Fcγ-receptors, Fcγ-RIIa is considered to be a dominant factor in mediating antibody dependent phagocytosis (ADCP). Of the two most prevalent allotypes of Fcγ-RIIa, the form with a histidine at amino acid position 131 (H131) is often described as the higher affinity allotype. (Nimmerjahn and Ravetch 2008, Yamada et al. 2013)

Here, relative binding of the small-scale purified aSyn-L971-mAb samples to FcRn and FcγIIa (His131) by surface plasmon resonance (SPR) was determined. The relative binding of the small-scale purified aSyn-L971-mAb samples to the target was determined by ELISA.

FIGS. 11A-11E illustrate the direct comparison of aSyn-L971 antibody produced in the cell culture process with 3 mM L-cystine or 6 mM L-cysteine in cell culture medium, respectively. FIG. 11A shows that at the end of the 14-day production process, G1 form of anti-α-synuclein antibody L971 from the process with 6 mM L-cysteine in production medium was only marginally higher than that from the process with 3 mM L-cystine in production medium.

FIG. 11B shows that at the end of the 14-day production process, G2 form of anti-α-synuclein antibody L971 from the process with 6 mM L-cysteine in production medium was comparable to that from the process with 3 mM L-cystine in production medium.

FIG. 11C shows that at the end of the 14-day production process, about 33% higher FcRn relative binding level was observed for anti-α-synuclein antibody L971 from the process with 6 mM L-cysteine in production medium (relative level about 118%) than that of anti-α-synuclein antibody L971 from the process with 3 mM L-cystine in production medium (relative level about 85%)

FIG. 11D shows that at the end of the 14-day production process, about 36% higher Fcγ-RIIa (H131) relative binding level was observed for anti-α-synuclein antibody L971 from the process with 6 mM L-cysteine in production medium (relative level about 113%) than that of anti-α-synuclein antibody L971 from the process with 3 mM L-cystine in production medium (relative level about 77%)

FIG. 11E shows that at the end of the 14-day production process, about 35% higher target relative binding level was observed for anti-α-synuclein antibody L971 from the process with 6 mM L-cysteine in production medium (relative level about 118%) than that of anti-α-synuclein antibody L971 from the process with 3 mM L-cystine in production medium (relative level about 83%).

TABLE 1

EXPERIMENTAL RESULTS SUMMARY

| No. | Antibody | Description | Relative level of G0 (at Day-14) (%) | Relative level of G1 (at Day-14) (%) | Relative level of G2 (at Day-14) (%) | Relative Titer (at Day-14) (%) | Relative level of FcRn binding (at Day-14) (%) | Relative level of FcγRIIa binding (at Day-14) (%) | Relative level of Target binding (at Day-14) (%) | Relative level of IVCD (at Day-14) (%) |
|---|---|---|---|---|---|---|---|---|---|---|
| EXAMPLE-3 | anti-α-synuclein | anti-α-Synuclein L965 (6 mM Cys) | 55.3 | 31.2 | 8.4 | 173.2 | not measured | not measured | not measured | 377.1 |
| | | anti-α-Synuclein L965 (10 mM Cys) | 71.7 | 17.2 | 3.1 | 100.0 | not measured | not measured | not measured | 100.0 |
| EXAMPLE-4 | anti CD20- (T cell bispecific) CD3 TCB | anti CD20-CD3 TCB (5 mM cysteine) | 71.6 | 26.0 | not measured | 165.9 | not measured | not measured | not measured | 183.5 |
| | | anti CD20-CD3 TCB (10 mM cysteine) | 75.9 | 22.6 | not measured | 100.0 | not measured | not measured | not measured | 100.0 |
| EXAMPLE-5 | anti CD20-CD3 TCB | anti CD20-CD3 TCB (5 mM cysteine) | 70.1 | 28.0 | not measured | 167.0 | not measured | not measured | not measured | 179.1 |
| | | anti CD20-CD3 TCB (10 mM cysteine) | 73.2 | 25.5 | not measured | 100.0 | not measured | not measured | not measured | 100.0 |
| EXAMPLE-6 | anti-α-synuclein | anti-α s-synuclein L967 (2 mM Cystine) | 71.1 | 21.8 | 3.1 | 91.1 | not measured | not measured | not measured | 96.3 |
| | | anti-α-synuclein L967 (4 mM Cystine) | 64.0 | 27.8 | 4.7 | 100.0 | not measured | not measured | not measured | 100.0 |
| EXAMPLE-7 | anti-α-synuclein | anti-α-synuclein L971 (2 mM Cystine) | 65.6 | 25.5 | 4.2 | 69.5 | not measured | not measured | not measured | 101.4 |
| | | anti-α-synuclein L971 (4 mM Cystine) | 63.5 | 27.2 | 4.4 | 100.0 | not measured | not measured | not measured | 100.0 |
| EXAMPLE-8 | | anti-α-synuclein L971 (3 mM Cystine) | 68.5 | 25.4 | 3.5 | 101.3 | 85.0 | 77.0 | 83.0 | not measured |
| | anti-α-synuclein | anti-α-synuclein L971 (6 mM Cysteine) | 66.6 | 27.2 | 4.6 | 100.0 | 118.0 | 113.0 | 118.0 | not measured |

| Sequence dentification | Sequences and sequence identification number (SEQ ID NO.s) |
|---|---|
| cDNA sequence of UDP-glucose 4-epimerase in CHO KIM | atg gcc gag aag gtg ctg gtc aca ggc<br>gga gct ggc tac att ggc agc cac acg<br>gta ctg gag ctg ctg gag gca ggc tac<br>gcc cct gtg gtc atc gac aac ttc cat<br>aat gcc att cgt gga ggg gat tcc atg<br>cct gag agc ctg cgg cgg gtc cag gaa<br>ctg aca ggc cgc tct gtg gag ttt gag<br>gag atg gac atc ttg gac cag gca gcg<br>cta cag cac ctc ttt aag aag cac agc<br>ttt aag gct gtc atc cac ttt gct ggg<br>ctc aag gct gtg ggc gag tcg gtg cag<br>aag cct ctg gat tat tat aga gtt aac<br>cta aca ggg acc atc cag ctt ctg gag<br>atc atg agg gcc cac ggg gtg aag aat<br>ctc gtg ttc agc agc tca gcc acc gtg<br>tat ggg aat ccc cag tac ctg cct ctg<br>gat gag gcc cac ccc acc ggg ggt tgt<br>acc aac ccc tat gga aag tcc aag ttc<br>ttc atc gag gag atg gtc cgg gac ctg<br>tgc cgg gca gat tcg gcc tgg aac gca<br>gtg ctg cta cgc tac ttc aat ccc acg<br>ggt gcc cac gcc tct ggc cgc atc ggc<br>gag gat ccc cag ggc gtc ccc aac aac<br>ctc atg ccc tat gtc tcc cag gig gca<br>att ggg cga cga gag gcc ctg aat gtc<br>ttt ggt ggt gac tat gat aca gag gat<br>ggc aca ggt gta agg gat tac att cat<br>gtg gtg gat ctg gcg aag ggc cac atc<br>gca gcc ttg aag aag ctg aag gag caa<br>tgt ggt tgc cgg atc tac aac ctg ggc<br>aca ggc aca ggc tac tct gtc ctg cag<br>atg gtc caa gca atg gag aag gct tca<br>ggg aag aag atc cca tac aag gtg gtg<br>gca cgg cgg gaa ggt gac gtg gca gcc<br>tgt tat gcc aac ccc agc ctg gcc cat<br>gag gag ctg ggc tgg aca gca gcc ttg<br>ggg ctg gac agg atg tgt gaa gat cta<br>tgg cgc tgg cag aag cag aac cct tca<br>ggc ttt gga gca cag gcc taa (SEQ ID NO.: 1) |
| Amino acid sequence of UDP-glucose 4-epimerase in CHO KIM | MAEKVLVTGGAGYIGSHTVLELLEAGYAPVVIDNFHNAIR<br>GGDSMPESLRRVQELTGRSVEFEEMDILDQAALQHLFKK<br>HSFKAVIHFAGLKAVGESVQKPLDYYRVNLTGTIQLLEIM<br>RAHGVKNLVFSSSATVYGNPQYLPLDEAHPTGGCTNPYG<br>KSKFFIEEMVRDLCRADSAWNAVLLRYFNPTGAHASGRI<br>GEDPQGVPNNLMPYVSQVAIGRREALNVFGGDYDTEDGT<br>GVRDYIHVVDLAKGHIAALKKLKEQCGCRIYNLGTGTGY<br>SVLQMVQAMEKASGKKIPYKVVARREGDVAACYANPSL<br>AHEELGWTAALGLDRMCEDLWRWQKQNPSGFGAQA<br>(SEQ ID NO.: 2) |
| The cDNA sequence of UDP-α-D-glucose: α-D-galactose-1-phosphate uridylyltransferase in CHO K1M | atg tcg caa aac gga gat gat cct gag<br>cag cgc cag cag gcg tca gag gcg gac<br>gcc atg gca gcg acc ttc cgg gcg agc<br>gaa cac cag cat att cgc tac aat ccg<br>ctc cag gat gag tgg gtg tta gtg tcg<br>gcc cat cgc atg aag cgg ccc tgg caa<br>gga caa gtg gag ccc cag ctt ctg aag<br>aca gtg ccc cgc tat gac cca ctc aac<br>cct ctg tgt ccc ggg gcc aca cga gcc<br>aat ggg gag gtg aat cca cac tat gac<br>agc acc ttc ctg ttt gac aat gac ttc<br>cca gct ctg cag ccc gat gct ccg gat<br>cca gga ccc agt gac cat cct ctt ttt<br>cga gca gag gcg gcc aga gga gtt tgt<br>aag gtc atg tgc ttc atc ccc tgg tcg<br>gat gtg aca ctg cca ctc atg tca gtc<br>cct gag atc cga gct gtc atc gat gcc<br>tgg gct tca gtc acc gag gat ctg ggt<br>gcc cag tat cct tgg gtg cag atc ttt<br>gaa aac aaa gga gcc atg atg ggc tgt<br>tct aac ccc cac ccc cac tgc cag gtt<br>tgg gcc agc agt ttc ctg cca gat att<br>gcc cag cgt gaa gtg cga tcc cag cag<br>aac tat cac agc cag cat gga gaa cct<br>ctg tta ctg gaa tat ggc cgc caa gaa<br>ctc ctc agg aag gaa cgt ctg gtc tta |

-continued

| Sequence dentification | Sequences and sequence identification number (SEQ ID NO.s) |
|---|---|
| | tct agt gag cac tgg cta gtc ctg gtt<br>ccc ttc tgg gca gtg tgg gct ttc cag<br>aca cta ctg ctg ccc cgc cgg cat gta<br>cgt cgg cta cct gag ctg acc cct gct<br>gaa cgt gat gat cta gcc tcc atc atg<br>aag aag cta ttg acc aag tat gac aac<br>cta ttt gag aca tct ttt ccc tac tcc<br>atg ggc tgg cat ggg gct ccc acg gga<br>tta aag act gga gcc gcc tat gac cac<br>tcg cag cta cat gct cat tac tat ccc<br>cca ctc ctg cgc tct gct act gtc cgg<br>aaa ttc atg gtt ggc tat gaa atg ctt<br>gcc cat ggg cac cgg gac ctc act cct<br>gaa cag gct gca gag aga cta agg gcg<br>ctt cct gag gta cat tat tgc ctg gca<br>aag aaa gac aag gaa aca gca gct gtt<br>gct tga (SEQ ID NO.: 3) |
| Amino acid sequence of UDP-α-D-glucose: α-D-galactose-1-phosphate uridylyltransferase in CHO KIM | MSQNGDDPEQRQQASEADAMAATFRASEHQHIRYNPLQ<br>DEWVLVSAHRMKRPWQGQVEPQLLKTVPRYDPLNPLCP<br>GATRANGEVNPHYDSTFLFDNDFPALQPDAPDPGPSDHPL<br>FRAEAARGVCKVMCFHPWSDVTLPLMSVPEIRA VIDAWA<br>SVTEDLGAQYPWVQIFENKGAMMGCSNPHPHCQVWASS<br>FLPDIAQREVRSQQNYHSQHGEPLLLEYGRQELLRKERLV<br>LSSEHWLVLVPFWAVWAFQTLLLPRRHVRRLPELTPAER<br>DDLASIMKKLLTKYDNLFETSFPYSMGWHGAPTGLKTGA<br>AYDHWQLHAHYYPPLLRSATVRKFMVGYEMLAHGHRD<br>LTPEQAAERLRALPEVHYCLAKKDKETAAVA (SEQ ID NO.: 4) |
| forward primer UDP_GlcE-F2-21 | atggccgaga aggtgctggt c (SEQ ID NO.: 5) |
| reverse primer UDP_GlcE-R21 | ttaggcctgt gctccaaagc c (SEQ ID NO.: 6) |
| forward primer UDP-Gal-T-F2-21 | atgtcgcaaa acggagatga t (SEQ ID NO.: 7) |
| reverse primer UDP-Gal-T-R18 | tcaagcaaca gctgctgt (SEQ ID NO.: 8) |
| amino acid sequence of natural human wild-type alpha-synuclein | MDVFMKGLSKAKEGVVAAAEKTKQGVAEAAGKTKEGV<br>LYVGSKTKEGVVHGVATVAEKTKEQVTNVGGAVVTGVT<br>AVAQKTVEGAGSIAAATGFVKKDQLGKNEEGAPQEGILE<br>DMPVDPDNEA YEMPSEEGYQDYEPEA (SEQ ID NO.: 9) |
| α-synuclein; CDR1 of heavy chain (CDR-H1) | NYGMS (SEQ ID NO.: 10) |
| α-synuclein; CDR2 of heavy chain (CDR-H2) | SISSGGGSTYYPDNVKG (SEQ ID NO.: 11) |
| α-synuclein; CDR3 of heavy chain (CDR-H3) | GGAGIDY (SEQ ID NO.: 12) |
| α-synuclein; CDR1 of light chain (CDR-L1) | KSIQTLLYSSNQKNYLA (SEQ ID NO.: 13) |
| α-synuclein; CDR2 of light chain (CDR-L2) | WASIRKS (SEQ ID NO.: 14) |
| α-synuclein; CDR3 of light chain (CDR-L3) | QQYYSYPLT (SEQ ID NO.: 15) |
| α-synuclein; heavy chain variable domain (VH) | EVQLVESGGGLVQPGGSLRLSCAASGFTFSNYGMSWVRQ<br>APGKGLEWVASISSGGGSTYYPDNVKGRFTISRDDAKNSL<br>YLQMNSLRAEDTAVYYCARGGAGIDYWGQGTLVTVSS<br>(SEQ ID NO.: 16) |
| α-synuclein; light chain variable domain (VL) | DIQMTQSPSSLSASVGDRVTITCKSIQTLLYSSNQKNYLAW<br>FQQKPGKAPKLLIYWASIRKSGVPSRFSGSGSGTDFTLTISS<br>LQPEDLATYYCQQYYSYPLTFGGGTKLEIK (SEQ ID NO.: 17) |

-continued

| Sequence dentification | Sequences and sequence identification number (SEQ ID NO.s) |
| --- | --- |
| α-synuclein; heavy chain constant domain (CH) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKRVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTP PVLDSDGSFFLYSKLTVDKSRWQQGNVFSCSVMHEALHN HYTQKSLSLSP (SEQ ID NO.: 18) |
| α-synuclein; light chain constant domain (CL) | RTVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC (SEQ ID NO.: 19) |
| α-synuclein; heavy chain (H) | EVQLVESGGGLVQPGGSLRLSCAASGFTFSNYGMSWVRQ APGKGLEWVASISSGGGSTYYPDNVKGRFTISRDDAKNSL YLQMNSLRAEDTAVYYCARGGAGIDYWGQGTLVTVSSA STKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKRVEPKSCDKTHTCPPCPAPELLGGPS VFLFPPKPKDTLMISRTPEVTCVVVDVSHEDPEVKFNWYV DGVEVHNAKTKPREEQYNSTYRVVSVLTVLHQDWLNGK EYKCKVSNKALPAPIEKTISKAKGQPREPQVYTLPPSREEM TKNQVSLTCLVKGFYPSDIAVEWESNGQPENNYKTTPPVL DSDGSFFLYSKLTVDKSRWQQGNVFSCSVMHEALHNHYT QKSLSLSP (SEQ ID NO.: 20) |
| α-synuclein; light chain (L) | DIQMTQSPSSLSASVGDRVTITCKSIQTLLYSSNQKNYLAW FQQKPGKAPKLLIYWASIRKSGVPSRFSGSGSGTDFTLTISS LQPEDLATYYCQQYYSYPLTFGGGTKLEIKRTVAAPSVFIF PPSDEQLKSGTASVVCLLNNFYPREAKVQWKVDNALQSG NSQESVTEQDSKDSTYSLSSTLTLSKADYEKHKVYACEVT HQGLSSPVTKSENRGEC (SEQ ID NO.: 21) |
| CD3; CDR1 of heavy chain (CDR-H1) | TYAMN (SEQ ID NO.: 22) |
| CD3; CDR2 of heavy chain (CDR-H2) | RIRSKYNNYATYYADSVKG (SEQ ID NO.: 23) |
| CD3; CDR3 of heavy chain (CDR-H3) | HGNFGNSYVSWFAY (SEQ ID NO.: 24) |
| CD3; CDR1 of light chain (CDR-L1) | GSSTGAVTTSNYAN (SEQ ID NO.: 25) |
| CD3; CDR2 of light chain (CDR-L2) | GTNKRAP (SEQ ID NO.: 26) |
| CD3; CDR3 of light chain (CDR-L3) | ALWYSNLWV (SEQ ID NO.: 27) |
| CD3; heavy chain variable domain (VH) | EVQLLESGGGLVQPGGSLRLSCAASGFTFSTYAMNWVRQ APGKGLEWVSRIRSKYNNYATYYADSVKGRFTISRDDSK NTLYLQMNSLRAEDTAVYYCVRHGNFGNSYVSWFAYW GQGTLVTVSS (SEQ ID NO.: 28) |
| CD3; light chain variable domain (VL) | QAVVTQEPSLTVSPGGTVTLTCGSSTGAVTTSNYANWVQ EKPGQAFRGLIGGTNKRAPGTPARFSGSLLGGKAALTLS GAQPEDEAEYYCALWYSNLWVFGGGTKLTVL (SEQ ID NO.: 29) |
| CD3; heavy chain constant domain (CH) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPK (SEQ ID NO.: 30) |
| CD3; light chain constant domain (CL) | ASVAAPSVFIFPPSDEQLKSGTASVVCLLNNFYPREAKVQ WKVDNALQSGNSQESVTEQDSKDSTYSLSSTLTLSKADY EKHKVYACEVTHQGLSSPVTKSFNRGEC (SEQ ID NO.: 31) |

-continued

| Sequence dentification | Sequences and sequence identification number (SEQ ID NO.s) |
|---|---|
| CD3; heavy chain constant domain (CD3 CH) | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPK (SEQ ID NO.: 32) |
| CD3; light chain (CD3 VH-CL) | EVQLLESGGGLVQPGGSLRLSCAASGFTFSTYAMNWVRQ APGKGLEWVSRIRSKYNNYATYYADSVKGRFTISRDDSK NTLYLQMNSLRAEDTAVYYCVRHGNFGNSYVSWFAYWGQ GTLVTVSSASVAAPSVFIFPPSDEQLKSGTASVVCLLNN FYPREAKVQWKVDNALQSGNSQESVTEQDSKDSTYSLSS TLTLSKADYEKHKVYACEVTHQGLSSPVTKSFNRGEC (SEQ ID NO.: 33) |
| CD20; CDR1 of heavy chain (CDR-H1) | YSWIN (SEQ ID NO.: 34) |
| CD20; CDR2 of heavy chain (CDR-H2) | RIFPGDGDTDYNGKFKG (SEQ ID NO.: 35) |
| CD20; CDR3 of heavy chain (CDR-H3) | NVFDGYWLVY (SEQ ID NO.: 36) |
| CD20; CDR1 of light chain (CDR-L1) | RSSKSLLHSNGITYLY (SEQ ID NO.: 37) |
| CD20; CDR2 of light chain (CDR-L2) | QMSNLVS (SEQ ID NO.: 38) |
| CD20; CDR3 of light chain (CDR-L3) | AQNLELPYT (SEQ ID NO.: 39) |
| CD20; heavy chain variable domain (VH) | QVQLVQSGAEVKKPGSSVKVSCKASGYAFSYSWINWVR QAPGQGLEWMGRIFPGDGDTDYNGKFKGRVTITADKSTS TAYMELSSLRSEDTAVYYCARNVFDGYWLVYWGQGTLV TVSS (SEQ ID NO.: 40) |
| CD20; light chain variable domain (VL) | DIVMTQTPLSLPVTPGEPASISCRSSKSLLHSNGITYLYWY LQKPGQSPQLLIYQMSNLVSGVPDRFSGSGSGTDFTLKISR VEAEDVGVYYCAQNLELPYTFGGGTKVEIKRTV (SEQ ID NO.: 41) |
| CD20; heavy chain constant domain (CH) | ASTKGPSVFPLAPSSKSTSGGTAALGCLVEDYFPEPVTVS WNSGALTSGVHTFPAVLQSSGLYSLSSVVTVPSSSLGTQT YICNVNHKPSNTKVDEKVEPK (SEQ ID NO.: 42) |
| CD20; light chain constant domain (CL) | AAPSVFIFPPSDRKLKSGTASVVCLLNNFYPREAKVQWKV DNALQSGNSQESVTEQDSKDSTYSLSSTLTLSKADYEKHK VYACEVTHQGLSSPVTKSFNRGEC (SEQ ID NO.: 43) |
| CD20; light chain (VL-CL) | DIVMTQTPLSLPVTPGEPASISCRSSKSLLHSNGITYLYWY LQKPGQSPQLLIYQMSNLVSGVPDRFSGSGSGTDFTLKISR VEAEDVGVYYCAQNLELPYTFGGGTKVEIKRTVAAPSVFI FPPSDRKLKSGTASVVCLLNNFYPREAKVQWKVDNALQS GNSQESVTEQDSKDSTYSLSSTLTLSKADYEKHKVYACEV THQGLSSPVTKSFNRGEC (SEQ ID NO.: 44) |
| CD20; heavy chain [CD20 VH-CH1(EE)- Fc (hole, P329G LALA)] | QVQLVQSGAEVKKPGSSVKVSCKASGYAFSYSWINWVR QAPGQGLEWMGRIFPGDGDTDYNGKFKGRVTITADKSTS TAYMELSSLRSEDTAVYYCARNVFDGYWLVYWGQGTLV VSSASTKGPSVFPLAPSSKSTSGGTAALGCLVEDYFPEPV TVSWNSGALTSGVHTFPAVLQSSGLYSLSSVVTVPSSSLG TQTYICNVNHKPSNTKVDEKVEPKSCDKTHTCPPCPAPEA AGGPSVFLFPPKPKDTLMISRTPEVTCVVVDVSHEDPEVK FNWYVDGVEVHNAKTKPREEQYNSTYRVVSVLTVLHQD WLNGKEYKCKVSNKALGAPIEKTISKAKGQPREPQVCTLP PSRDELTKNQVSLSCAVKGFYPSDIAVEWESNGQPENNYK TTPPVLDSDGSFFLVSKLTVDKSRWQQGNVFSCSVMHEA LHNHYTQKSLSLSP (SEQ ID NO.: 45) |
| CD3; heavy chain [CD3 VL-CH1-Fc (knob, P329G LALA)] | QAVVTQEPSLTVSPGGTVTLTCGSSTGAVTTSNYANWVQ EKPGQAFRGLIGGTNKRAPGTPARFSGSLLGGKAALTLSG AQPEDEAEYYCALWYSNLWVFGGGTKLTVLSSASTKGPS VFPLAPSSKSTSGGTAALGCLVKDYFPEPVTVSWNSGALT SGVHTFPAVLQSSGLYSLSSVVTVPSSSLGTQTYICNVNHK PSNTKVDKKVEPKSCDKTHTCPPCPAPEAAGGPSVFLFPP |

-continued

| Sequence dentification | Sequences and sequence identification number (SEQ ID NO.s) |
|---|---|
| | KPKDTLMISRTPEVTCVVVDVSHEDPEVKFNWYVDGVEV HNAKTKPREEQYNSTYRVVSVLTVLHQDWLNGKEYKCK VSNKALGAPIEKTISKAKGQPREPQVYTLPPCRDELTKNQ VSLWCLVKGFYPSDIAVEWESNGQPENNYKTTPPVLDSD GSFFLYSKLTVDKSRWQQGNVFSCSVMHEALHNHYTQKS LSLSP (SEQ ID NO.: 46) |
| CD20-CD3; heavy chain [CD20 VH-CH1(EE)-CD3 VL-CH1-Fc (knob, P329G LALA)] | QVQLVQSGAEVKKPGSSVKVSCKASGYAFSYSWINWVR QAPGQGLEWMGRIFPGDGDTDYNGKFKGRVTITADKSTS TAYMELSSLRSEDTAVYYCARNVFDGYWLVYWGQGTLV TVSSASTKGPSVFPLAPSSKSTSGGTAALGCLVEDYFPEPV TVSWNSGALTSGVHTFPAVLQSSGLYSLSSVVTVPSSSLG TQTYICNVNHKPSNTKVDEKVEPKSCDGGGGSGGGGS QAVVTQEPSLTVSPGGTVTLTCGSSTGAVTTSNYANWVQ EKPGQAFRGLIGGTNKRAPGTPARFSGSLLGGKAALTLSG AQPEDEAEYYCALWYSNLWVFGGGTKLTVLSSASTKGPS VFPLAPSSKSTSGGTAALGCLVKDYFPEPVTVSWNSGALT SGVHTFPAVLQSSGLYSLSSVVTVPSSSLGTQTYICNVNHK PSNTKVDKKVEPKSCDKTHTCPPCPAPEAAGGPSVFLFPP KPKDTLMISRTPEVTCVVVDVSHEDPEVKFNWYVDGVEV HNAKTKPREEQYNSTYRVVSVLTVLHQDWLNGKEYKCK VSNKALGAPIEKTISKAKGQPREPQVYTLPPCRDELTKNQ VSLWCLVKGFYPSDIAVEWESNGQPENNYKTTPPVLDSD GSFFLYSKLTVDKSRWQQGNVFSCSVMHEALHNHYTQKS LSLSP (SEQ ID NO.: 47) |

The invention claimed is:

1. An anti α-synuclein antibody having monogalactosylated and digalactosylated glycans, wherein the anti α-synuclein antibody comprises a heavy chain variable domain comprising
    (a) CDR-H1 comprising the amino acid sequence of SEQ ID NO: 10,
    (b) CDR-H2 comprising the amino acid sequence of SEQ ID NO: 11, and
    (c) CDR-H3 comprising the amino acid sequence of SEQ ID NO: 12;
    and
a light chain variable domain comprising
    (d) CDR-L1 comprising the amino acid sequence of SEQ ID NO: 13,
    (e) CDR-L2 comprising the amino acid sequence of SEQ ID NO: 14, and
    (f) CDR-L3 comprising the amino acid sequence of SEQ ID NO: 15;
    and
        wherein the anti α-synuclein antibody has 17.2-48.0% (w/w) of monogalactosylated glycans and 3.1-15.0% (w/w) of digalactosylated glycans per total glycan.

2. The anti α-synuclein antibody of claim 1,
wherein the heavy chain variable domain comprises the amino acid sequence of SEQ ID NO: 16; and
wherein the light chain variable domain comprises the amino acid sequence of SEQ ID NO: 17.

3. The anti α-synuclein antibody of claim 1, wherein the anti α-synuclein antibody comprises a heavy chain of the amino acid sequence of SEQ ID NO: 20 and a light chain of the amino acid sequence of SEQ ID NO: 21.

4. A method of producing the anti α-synuclein antibody of claim 1 having monogalactosylated and digalactosylated glycans, said method comprising:
    (a) cultivating a mammalian cell in a cell culture medium, comprising at least one sulfhydryl compound,
        wherein the concentration of the sulfhydryl compound is at least 4.0 and less than 10.0 mM the glucose in the cell culture medium is maintained at least at 3.0 g/L for at least 3 days
    (b) isolating said antibody;
        wherein the sulfhydryl compound is selected from the group consisting of cysteine, cystine, and a combination thereof, and
        wherein the mammalian cell is a CHO cell.

5. The method of claim 4, wherein the concentrations of the sulfhydryl compound and glucose is maintained for at least 4, days, 5 day, 7 days, 10 days, 12 days, or 14 days.

6. The method of claim 4, wherein the cell culture medium comprises at least 5.0 mM and less than 10.0 mM of the sulfhydryl group(s) from the at least one sulfhydryl compound(s).

7. The method of claim 4, wherein the cell culture medium comprises between 3.0 g/L and 13 g/L glucose.

8. The method of claim 4, wherein the cell culture medium is a chemically defined medium, optionally a serum-free, protein-free and/or oligopeptide-free cell culture medium.

9. An anti α-synuclein antibody having monogalactosylated and digalactosylated glycans comprising
a heavy chain variable domain comprising the amino acid sequence of SEQ ID NO: 16 and a light chain variable domain comprising the amino acid sequence of SEQ ID NO: 17;

wherein the heavy chain variable domain comprises:
    (i) CDR-H1 comprising the amino acid sequence of SEQ ID NO: 10,
    (ii) CDR-H2 comprising the amino acid sequence of SEQ ID NO: 11, and
    (iii) CDR-H3 comprising the amino acid sequence of SEQ ID NO: 12; and,
wherein the light chain variable domain comprises:
    (i) CDR-L1 comprising the amino acid sequence of SEQ ID NO: 13,
    (ii) CDR-L2 comprising the amino acid sequence of SEQ ID NO: 14, and
    (iii) CDR-L3 comprising the amino acid sequence of SEQ ID NO: 15,
wherein the anti α-synuclein antibody has 17.2-48.0% (w/w) of monogalactosylated glycans and 3.1-15.0% (w/w) of digalactosylated glycans per total glycan.

10. An anti α-synuclein antibody having monogalactosylated and digalactosylated glycans comprising
a heavy chain comprising the amino acid sequence of SEQ ID NO: 20 and a light chain comprising the amino acid sequence of SEQ ID NO: 21;
wherein the heavy chain variable domain comprises:
    (i) CDR-H1 comprising the amino acid sequence of SEQ ID NO: 10,
    (ii) CDR-H2 comprising the amino acid sequence of SEQ ID NO: 11, and
    (iii) CDR-H3 comprising the amino acid sequence of SEQ ID NO: 12;
wherein the light chain variable domain comprises:
    (i) CDR-L1 comprising the amino acid sequence of SEQ ID NO: 13,
    (ii) CDR-L2 comprising the amino acid sequence of SEQ ID NO: 14, and
    (iii) CDR-L3 comprising the amino acid sequence of SEQ ID NO: 15,
wherein the anti α-synuclein antibody has 17.2-48.0% (w/w) of monogalactosylated glycans and 3.1-15.0% (w/w) of digalactosylated glycans per total glycan.

11. The anti α-synuclein antibody of claim 1, wherein the anti α-synuclein antibody has 25.4-48.0% (w/w) of monogalactosylated glycans and 3.5-15.0% (w/w) of digalactosylated glycans per total glycan; 27.2-47.0% of monogalactosylated glycans and 4.4 to 15.0% of digalactosylated glycans per total glycan; 40.0-46.0% (w/w) of monogalactosylated glycans and 8.4-15.0% (w/w) of digalactosylated glycans per total glycan; 41.0-45.0% (w/w) of monogalactosylated glycans and 9.5-14.0% (w/w) of digalactosylated glycans per total glycan or 42.1-43.9% (w/w) of monogalactosylated glycans and 10.6-13.3% (w/w) of digalactosylated glycans per total glycan.

12. The anti α-synuclein antibody of claim 9, wherein the anti α-synuclein antibody has 25.4-48.0% (w/w) of monogalactosylated glycans and 3.5-15.0% (w/w) of digalactosylated glycans per total glycan; 27.2-47.0% of monogalactosylated glycans and 4.4 to 15.0% of digalactosylated glycans per total glycan; 40.0-46.0% (w/w) of monogalactosylated glycans and 8.4-15.0% (w/w) of digalactosylated glycans per total glycan; 41.0-45.0% (w/w) of monogalactosylated glycans and 9.5-14.0% (w/w) of digalactosylated glycans per total glycan or 42.1-43.9% (w/w) of monogalactosylated glycans and 10.6-13.3% (w/w) of digalactosylated glycans per total glycan.

13. The anti α-synuclein antibody of claim 10, wherein the anti α-synuclein antibody has 25.4-48.0% (w/w) of monogalactosylated glycans and 3.5-15.0% (w/w) of digalactosylated glycans per total glycan; 27.2-47.0% of monogalactosylated glycans and 4.4 to 15.0% of digalactosylated glycans per total glycan; 40.0-46.0% (w/w) of monogalactosylated glycans and 8.4-15.0% (w/w) of digalactosylated glycans per total glycan; 41.0-45.0% (w/w) of monogalactosylated glycans and 9.5-14.0% (w/w) of digalactosylated glycans per total glycan or 42.1-43.9% (w/w) of monogalactosylated glycans and 10.6-13.3% (w/w) of digalactosylated glycans per total glycan.

* * * * *

132